US009005575B2

(12) United States Patent
Miao et al.

(10) Patent No.: US 9,005,575 B2
(45) Date of Patent: Apr. 14, 2015

(54) ARG-GLY-ASP-CONJUGATED ALPHA-MELANOCYTE STIMULATING HORMONE HYBRID PEPTIDE FOR USE IN DIAGNOSING AND TREATING MELANOMA, INCLUDING METASTATIC MELANOMA AND METHODS RELATED TO SAME

(75) Inventors: Yubin Miao, Albuquerque, NM (US); Jianquan Yang, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 615 days.

(21) Appl. No.: 13/321,942

(22) PCT Filed: May 28, 2010

(86) PCT No.: PCT/US2010/036686
§ 371 (c)(1),
(2), (4) Date: Dec. 27, 2011

(87) PCT Pub. No.: WO2011/005380
PCT Pub. Date: Jan. 13, 2011

(65) Prior Publication Data
US 2012/0107237 A1 May 3, 2012

Related U.S. Application Data

(60) Provisional application No. 61/268,409, filed on Jun. 12, 2009.

(51) Int. Cl.
| | | |
|---|---|---|
| *A61K 51/00* | (2006.01) | |
| *A61M 36/14* | (2006.01) | |
| *C07K 14/68* | (2006.01) | |
| *A61K 51/08* | (2006.01) | |
| *C12N 9/88* | (2006.01) | |
| *A61K 38/00* | (2006.01) | |

(52) U.S. Cl.
CPC ............. *C07K 14/68* (2013.01); *A61K 38/00* (2013.01); *A61K 51/088* (2013.01); *C12N 9/88* (2013.01); *A61K 51/086* (2013.01); *A61K 51/082* (2013.01)

(58) Field of Classification Search
CPC ....... A61K 38/00; A61K 38/04; A61K 38/08; A61K 38/10; A61K 38/12; A61K 39/00; A61K 51/08; A61K 51/088; A61K 51/00; A61K 51/02; A61K 51/04; A61K 51/06; A61K 51/065; A61K 2121/00; A61K 2123/00; A61K 49/00; A61K 49/0002; A61K 49/0004; A61K 49/001; A61K 49/0013; A61K 49/0015; A61K 49/0017; A61K 49/0019; A61K 49/0021; A61K 49/04; A61K 49/06; A61K 49/10; A61K 49/101; A61K 49/12; A61K 49/14; A61K 51/082; A61K 51/086; A61K 38/20; A61K 38/21; C07K 14/68; C07K 7/00; C07K 7/02; C07K 7/06; C07K 7/08; C07K 7/04; C07K 7/50; C07K 7/54; C07K 7/64; C07K 4/00; C07K 5/12; C07K 1/00; C07K 17/00; C07K 17/02; C12N 9/88

USPC ........... 424/1.11, 1.49, 1.65, 1.69, 1.81, 1.85, 424/1.89, 9.1, 9.2, 9.3, 9.4, 9.5, 9.6, 85.2, 424/85.7; 514/1, 1.1, 10.7, 19.2, 19.3; 530/300, 317, 323, 326, 327, 330, 332, 530/333, 338, 312

See application file for complete search history.

(56) References Cited

U.S. PATENT DOCUMENTS

| 5,932,189 A | 8/1999 | Dean et al. |
| 2005/0069494 A1 | 3/2005 | Li et al. |

FOREIGN PATENT DOCUMENTS

| WO | 9837097 A1 | 8/1998 |
| WO | 2009045536 A2 | 4/2009 |

OTHER PUBLICATIONS

Yang, Jianquan et al.. A novel RGD-conjugated alpha-MSH hybrid peptide for melanoma therapy. J Nucl Med. 2009; 50, Supplement 2:438-.

Jemal A, Siegel R, Ward E, et al. Cancer statistics, 2008. CA Cancer J Clin. 2008;58:71-96.

Marghoob AA, Slade J, Salopek TG, Kopf AW, Bart RS, Rigel DS. Basal cell and squamous cell carcinomas are important risk factors for cutaneous malignant melanoma. Cancer. 1995;75:707-714.

Balch CM, Soong SJ, Gershenwald JE, et al. Prognostic factors analysis of 17,600 melanoma patients: validation of the American joint committee on cancer melanoma staging system. J Clin Oncol. 2001;19:3622-3634.

Anderson CM, Buzaid AC. Systematic treatments for advanced cutaneous melanoma. Oncology. 1995;9:1149-1158, 1163-1164, 1167-1168.

(Continued)

*Primary Examiner* — D L Jones
(74) *Attorney, Agent, or Firm* — Henry D. Coleman; R. Neil Sudol

(57) ABSTRACT

The present invention is directed to novel non-invasive diagnostic and therapeutic tools/compounds comprising a hybride cyclic peptide which utilizes a cyclic peptide chelating group wherein the compound binds to a MSH receptor to image and treat cancers, especially, melanoma, including metastatic melanoma in vivo. The present invention represents a clear advance in the art which presently relies on tissue biopsy for diagnoses of these cancers. The novel imaging probes are capable of detecting cancerous melanoma cells, as well as their metastatic spread in tissues. This represents a quantum step forward in the diagnosis and treatment of melanoma, including metastatic melanoma using non-invasive molecular imaging techniques. The novel probes of the present invention will also be useful to initiate therapy for melanoma as well as monitor patients response to chemotherapy treatments and other interventions or therapies used in the treatment of melanoma/metastatic melanoma. Compound according to the present invention may be used as diagnostic tools for a number of conditions and diseases states as well as therapeutic agents for treating such conditions and disease states.

52 Claims, 16 Drawing Sheets

(56) References Cited

OTHER PUBLICATIONS

Tatro JB, Reichlin S. Specific receptors for alpha-melanocyte-stimulating hormone are widely distributed in tissues of rodents. Endocrinology. 1987;121:1900-1907.

Siegrist W, Solca F, Stutz S, Giuffre L, Carrel S, Girard J, Eberle AN. Characterization of receptors for alpha-melanocyte-stimulating hormone on human melanoma cells. Cancer Res. 1989;49:6352-6358.

Chen J, Cheng Z, Hoffman TJ, Jurisson SS, Quinn TP. Melanoma-targeting properties of 99mTechnetium-labeled cyclic a-melanocyte-stimulating hormone peptide analogues. Cancer Res. 2000;60:5649-5658.

Miao Y, Owen NK, Whitener D, Gallazzi F, Hoffman TJ, Quinn TP. In vivo evaluation of 188Re-labeled alpha-melanocyte stimulating hormone peptide analogs for melanoma therapy. Int J Cancer. 2002;101:480-487.

Miao Y, Whitener D, Feng W, Owen NK, Chen J, Quinn TP. Evaluation of the human melanoma targeting properties of radiolabeled alpha-Melanocyte stimulating hormone peptide analogues. Bioconjug Chem. 2003;14:1177-1184.

Giblin MF, Wang NN, Hoffman TJ, Jurisson SS, Quinn TP. Design and characterization of a-melanotropin peptide analogs cyclized through rhenium and technetium metal coordination. Proc Natl Acad Sci USA. 1998;95:12814-12818.

Froidevaux S, Calame-Christe M, Tanner H, Sumanovski L, Eberle AN. A novel DOTA-a-melanocyte-stimulating hormone analog for metastatic melanoma diagnosis. J Nucl Med. 2002;43:1699-1706.

Froidevaux S, Calame-Christe M, Schuhmacher J, et al. A Gallium-labeled DOTA-a-melanocyte-stimulating hormone analog for Pet imaging of melanoma metastases. J Nucl Med. 2004;45:116-123.

Miao Y, Benwell K, Quinn TP. 99mTc and 111In labeled alpha-melanocyte stimulating hormone peptides as imaging probes for primary and pulmonary metastatic melanoma detection. J Nucl Med. 2007;48:73-80.

Miao Y, Figueroa SD, Fisher DR, et al. 203Pb-labeled alpha-melanocyte stimulating hormone peptide as an imaging probe for melanoma detection. J Nucl Med. 2008;49:823-829.

Miao Y, Owen NK, Fisher DR, Hoffman TJ, Quinn TP. Therapeutic efficacy of a 188Re labeled a-melanocyte stimulating hormone peptide analog in murine and human melanoma-bearing mouse models. J Nucl Med. 2005;46:121-129.

Miao Y, Hylarides M, Fisher DR, et al. Melanoma therapy via peptide-targeted a-radiation. Clin Cancer Res. 2005;11:5616-5621.

Miao Y, Shelton T, Quinn TP. Therapeutic efficacy of a 177Lu labeled DOTA conjugated α-melanocyte stimulating hormone peptide in a murine melanoma-bearing mouse model. Cancer Biother Radiopharm. 2007;22:333-341.

Brooks PC, Clark RA, Cheresh DA. Requirement of vascular integrin avβ3 for angiogenesis. Science. 1994;264:569-571.

Hood JD, Cheresh DA. Role of integrins in cell invasion and migration. Nat Rev Cancer. 2002;2:91-100.

Brooks PC, Montgomery AM, Rosenfeld M, et al. Integrin avβ3 antagonists promote tumor regression by inducing apoptosis of angiogenic blood vessels. Cell. 1994;79:1157-1164.

Mitjans F, Meyer T, Fittschen C, et al. In vivo therapy of malignant melanoma by means of antagonists of av integrins. Int J Cancer. 2000;87:716-723.

Buckley CD, Pilling D, Henriquez NV, et al. RGD peptides induce apoptosis by direct caspase-3 activation. Nature. 1999;397:534-539.

Capello A, Krenning EP, Bernard BF, Breeman WAP, Van Hagen MP, De Jong M. Increased cell death after therapy with an Arg-Gly-Asp-linked somatostatin analog. J Nucl Med. 2004;45:1716-1720.

Bernard BF, Capello A, Van Hagen MP, et al. Radiolabeled RGD-DTPA-Tyr3-Octreotate for receptor-targeted radionuclide therapy. Cancer Biother Radiopharm. 2004;19:173-180.

Hofland LJ, Capello A, Krenning EP, De Jong M, Van Hagen MP. Induction of apoptosis with hybrids of Arg-Gly-Asp molecules and peptides and antimitotic effects of hybrids of cytostatic drugs and peptides. J Nucl Med. 2005;46:191S-198S.

Capello A, Krenning EP, Bernard BF, Breeman WAP, Erion JL, De Jong M. Anticancer activity of targeted proapoptotic peptides. J Nucl Med. 2006;47:122-129.

Miao Y, Gallazzi F, Guo H, Quinn TP. 111In-labeled lactam bridge-cyclized alpha-melanocyte stimulating hormone peptide analogues for melanoma imaging. Bioconjug Chem. 2008;19:539-547.

Heppeler A, Froidevaux S, Eberle AN, Maecke HR. Receptor targeting for tumor localization and therapy with radiopeptides. Curr Med Chem. 2000;7:971-994.

Fung S, Hruby VJ. Design of cyclic and other templates for potent and selective peptide a-MSH analogues. Curr Opinion in Chem Biol. 2005;9:352-358.

Schraa AJ, Kok RJ, Moorlag HE, et al. Targeting of RGD-modified proteins to tumor vasculature: a pharmacokinetic and cellular distribution study. Int J Cancer. 2002;102:469-475.

Miao Y, Owen NK, Whitener D, Gallazzi F, Hoffman TJ, Quinn TP. Optimizing the tumor to kidney uptake ratio of 188Re labeled alpha-melanocyte stimulating hormone peptide analogs through chemical modification. Technetium, Rhenium and Other Metals in Chemistry and Nuclear Medicine 6, Nicolini M., Mazzi U. Eds., Servizi Grafici Editoriali: Padova, Italy. 2002:567-570pp.

Miao Y, Hoffman TJ, Quinn TP. Tumor targeting properties of 90Y and 177Lu labeled alpha-melanocyte stimulating hormone peptide analogues in a murine melanoma model. Nucl Med Biol. 2005;32:485-493.

Miao Y, Fisher DR, Quinn TP. Reducing renal uptake of 90Y and 177Lu labeled alpha-melanocyte stimulating hormone peptide analogues. Nucl Med Biol. 2006;33:723-733.

Burke PA, DeNardo AJ, Miers LA, Lambom KR, Matzku S, DeNardo GL. Cilengitide targeting of αvb3 integrin receptor synergizes with radioimmunotherapy to increase efficacy and apoptosis in breast cancer xenografts. Cancer Res. 2002;62:4263-4272.

Marghoob A. A., Slade J., Salopek T. G., Kopf A. W., Bart R. S., and Rigel D. S. (1995) Basal cell and squamous cell carcinomas are important risk factors for cutaneous malignant melanoma. Cancer. 75, 707-714.

Balch C. M., Soong S. J., Gershenwald J. E., Thompson J. F., Reintgen D. S., Cascinelli N., Urist M., McMasters K. M., Ross M. I., Kirkwood J. M., Atkins M. B., Thompson J. A., Coit D. G., Byrd D., Desmond R., Zhang Y., Liu P. Y., Lyman G. H., and Morabito A. (2001) Prognostic factors analysis of 17,600 melanoma patients: validation of the American joint committee on cancer melanoma staging system. J Clin Oncol. 2001; 19:3622-3634.

Anderson C. M., Buzaid A. C., and Legha S. S. (1955) Systematic treatments for advanced cutaneous melanoma Oncology. 9, 1149-1158.

Giblin, M. F., Wang, N. N., Hoffman, T. J., Jurisson, S. S., Quinn, T. P. (1998) Design and charaterization of a-melanotropin peptide analogs cyclized through rhenium and technetium metal coordination. Proc. Natl. Acad. Sci. U.S.A. 95, 12814-12818.

Froidevaux, S., Calame-Christe, M., Tanner, H., Sumanovski, L., Eberle, A. N. (2002) A novel DOTA-a-melanocyte-stimulating hormone analog for metastatic melanoma diagnosis. J. Nucl. Med. 43, 1699-1706.

Froidevaux, S., Calame-Christe, M., Schuhmacher, J., Tanner, H., Saffrich, R., Henze, M., Eberle, A. N. (2004) A Gallium-labeled DOTA-a-melanocyte-stimulating hormone analog for PET imaging of melanoma metastases. J. Nucl. Med. 45, 116-123.

Miao, Y., Benwell, K., Quinn, T. P. (2007) 99mTc and 111In labeled alpha-melanocyte stimulating hormone peptides as imaging probes for primary and pulmonary metastatic melanoma detection. J. Nucl. Med. 48, 73-80.

Miao, Y., Figueroa S. D., Fisher D. R., Moore H. A., Testa R. F., Hoffman T. J., and Quinn T. P. (2008) 203Pb-labeled alpha-melanocyte stimulating hormone peptide as an imaging probe for melanoma detection. J. Nucl. Med. 49, 823-829.

Miao, Y., Owen, N. K., Fisher, D. R., Hoffman, T. J., Quinn, T. P. (2005) Therapeutic efficacy of a 188Re labeled a-melanocyte stimulating hormone peptide analogue in murine and human melanoma-bearing mouse models. J. Nucl. Med. 46, 121-129

(56) References Cited

OTHER PUBLICATIONS

Miao, Y., Hylarides, M., Fisher, D. R., Shelton, T., Moore, H., Wester, D. W., Fritzberg, A. R., Winkelmann, C. T., Hoffman, T. J., Quinn, T. P. (2005) Melanoma therapy via peptide-targeted a-radiation. Clin. Cancer Res. 11, 5616-5621.

Miao Y., Shelton T., and Quinn T. P. (2007) Therapeutic efficacy of a 177Lu labeled DOTA conjugated α-melanocyte stimulating hormone peptide in a murine melanoma-bearing mouse model. Cancer Biother. Radiopharm. 22, 333-341.

Tatro J. B., and Reichlin S. (1987) Specific receptors for alpha-melanocyte-stimulating hormone are widely distributed in tissues of rodents. Endocrinology. 121, 1900-1907.

Siegrist W., Solca F., Stutz S., Giuffre L., Carrel S., Girard J., and Eberle A. N. (1989) Characterization of receptors for alpha-melanocyte-stimulating hormone on human melanoma cells. Cancer Res. 49, 6352-6358.

Chen J., Cheng Z., Hoffman T. J., Jurisson S. S., and Quinn T. P. (2000) Melanoma-targeting properties of 99mTechnetium-labeled cyclic a-melanocyte-stimulating hormone peptide analogues. Cancer Res. 60, 5649-5658.

Miao Y., Owen N. K., Whitener D., Gallazzi F., Hoffman T. J., and Quinn T.P. (2002) In vivo evaluation of 188Re-labeled alpha-melanocyte stimulating hormone peptide analogs for melanoma therapy. Int. J. Cancer. 101, 480-487.

Miao Y., Whitener D., Feng W., Owen N. K., Chen J., and Quinn T. P. (2003) Evaluation of the human melanoma targeting properties of radiolabeled alpha-Melanocyte stimulating hormone peptide analogues. Bioconjug. Chem. 14, 1177-1184.

Yang J., Guo H., Gallazzi F., Padilla R. S., Berwick M., and Miao Y. (2009) Evaluation of a novel RGD-conjugated alpha-melanocyte stimulating hormone hybrid peptide for potential melanoma therapy. Bioconjug. Chem. 20, 1634-1642.

Jemal A., Siegel R., Ward E., Hao Y., Xu J., and Thun M. J. (2009) Cancer statistics, 2009. CA. Cancer J. Clin. 59, 225-249.

Wei L., Butcher C., Miao Y., Gallazzi F., Quinn T. P., Welch M. J., and Lewis J. S. (2007) Synthesis and Biological Evaluation of Cu-64 labeled Rhenium-Cyclized α-MSH Peptide Analog Using a Cross-Bridged Cyclam Chelator. J. Nucl. Med. 48, 64-72.

Miao Y., Fisher D. R., and Quinn T. P. (2006) Reducing renal uptake of 90Y and 177Lu labeled alpha-melanocyte stimulating hormone peptide analogues. Nucl. Med. Biol. 33, 723-733.

Structural Design

Figure 8. Schematic structures of novel RGD-conjugated α-MSH hybrid peptides.

$^{99m}$Tc-RGD-Lys-(Arg$^{11}$)CCMSH

Figure 9. Schematic structure of $^{99m}$Tc-RGD-Lys-(Arg$^{11}$)CCMSH

ARG-GLY-ASP-CONJUGATED ALPHA-MELANOCYTE STIMULATING HORMONE HYBRID PEPTIDE FOR USE IN DIAGNOSING AND TREATING MELANOMA, INCLUDING METASTATIC MELANOMA AND METHODS RELATED TO SAME

RELATED APPLICATIONS

This application claims priority from provisional application Ser. No. US61/268,409 entitled "Asp-Gly-Asp-conjugated Alpha-Melanocyte Stimulating Hormone Hybrid Peptide for Use in Diagnosing and Treating Melanoma, Including Metastatic Melanoma and Methods Related to Same", filed Jun. 12, 2009, the entire contents of which application is incorporated by reference herein.

This invention was made with support from grant no. DOD W81XWH-09-1-0105 and NIH-INBRE P20RR-16480. Consequently, the government retains certain rights in the invention.

FIELD OF THE INVENTION

The present invention is directed to novel non-invasive diagnostic tools/compounds to image and treat cancers, especially, melanoma, including metastatic melanoma in vivo. The present invention represents a clear advance in the art which presently relies on tissue biopsy for diagnoses of these cancers. The novel imaging probes are capable of detecting cancerous melanoma cells, as well as their metastatic spread in tissues. This represents a quantum step forward in the diagnosis and treatment of melanoma, including metastatic melanoma using non-invasive molecular imaging techniques. The novel probes of the present invention will also be useful to initiate therapy for melanoma, including metastatic melanoma, as well as monitor patients response to chemotherapy treatments and other interventions or therapies used in the treatment of melanoma/metastatic melanoma. Compounds according to the present invention may be used as diagnostic tools for a number of conditions and diseases states as well as therapeutic agents for treating such conditions and disease states.

BACKGROUND OF THE INVENTION

Skin cancer is the most commonly diagnosed cancer in the United States. Malignant melanoma is the most lethal form of skin cancer and the most commonly diagnosed malignancy among young adults with an increasing incidence. It was predicted that there would be 62,940 cases of malignant melanoma newly reported and 8,420 fatalities in 2008 (1). Melanoma metastases are highly aggressive and the survival time for patients with metastatic melanoma averages 3-15 months (2). Unfortunately, no curative treatment exists for metastatic melanoma. Early diagnosis and prompt surgical removal are a patient's best opportunity for a cure. Single photon emission tomography (SPECT) and positron emission tomography (PET) techniques are attractive noninvasive imaging modalities due to their high sensitivity ($10^{-10}$ to $10^{-11}$ M for SPECT and $10^{-11}$ to $10^{-12}$ M for PET) and spatial resolution (1-2 mm) (3, 4). Currently, 2-[$^{18}$F]fluoro-2-deoxy-D-glucose ([$^{18}$F] FDG) PET imaging is commonly used for the diagnosis and staging of melanoma. However, [$^{18}$F]FDG is not a melanoma-specific imaging probe since the elevated uptake of [$^{18}$F]FDG in tumor is due to the higher metabolism and energy consumption in tumor cells than that in normal cells. [$^{18}$F]FDG PET imaging only detects 23% melanoma metastases smaller than 5 mm (5). Meanwhile, some melanoma cells are not detected by [$^{18}$F]FDG PET imaging since they use substrates other than glucose as energy sources (6, 7). Therefore, it is highly desirable to develop novel effective imaging probes to detect primary, metastatic and recurrent melanomas.

Malignant melanoma is the most lethal form of skin cancer and the most commonly diagnosed malignancy among young adults with an increasing incidence. It was predicted that 62,480 cases would be diagnosed and 8,420 fatalities would occur in the year 2008 (1). Melanoma metastases are very aggressive and the survival time for patients with metastatic melanoma averages 3-15 months (2, 3). Unfortunately, no curative treatment exists for metastatic melanoma due to its resistance to current chemotherapy and immunotherapy regimens (4). Novel and effective treatment approaches are urgently needed to improve the effectiveness of melanoma treatment. The over-expression of melanocortin-1 (MC1) receptor on human and mouse melanoma cells (5-9) makes the MC1 receptor a distinct molecular target for developing novel diagnostic and therapeutic radiopharmaceuticals for melanoma (10-17). Radiolabeled α-melanocyte stimulating hormone (α-MSH) peptides can specifically bind the MC1 receptors with nanomolar binding affinities, can be rapidly internalized upon binding the MC1 receptors, can selectively deliver the diagnostic and therapeutic radionuclides to melanoma tumor cells for imaging and therapy (10-17). The very promising preclinical therapeutic efficacies of $^{177}$Lu-, $^{188}$Re- and $^{212}$Pb-labeled metal-cyclized α-MSH peptides in melanoma-bearing mice demonstrated their potential as effective therapeutic agents for melanoma treatment (15-17).

Integrins are a family of adhesion cell surface receptors composed of two non-covalently bound transmembrane glycoprotein subunits (α and β). The integrin receptors are involved in tumor metastasis and angiogenesis and mediate a variety of cell adhesion activities. Arg-Gly-Asp (RGD) peptide is recognized by many of the integrin receptors and is an important structural component of extracellular matrices that control physiological cell functions (18-21). Antagonists of $\alpha_v\beta_3$ integrin receptors promote tumor regression by inducing apoptosis of newly spouting blood vessels in the tumor (20). Besides the $\alpha_v\beta_3$ integrin receptors, several cytoplasmic members of the procaspase family of apoptosis genes, such as procaspase-1 and procaspase-3, contain RGD binding motif as well (22). It was reported that the RGD-containing peptide could induce cell apoptosis through activating cytoplasmic procaspase-3 directly after the RGD-containing peptide entering the cells without any requirement for integrin-mediated cell clustering or signals (22), highlighting the novel concept of using the RGD motif as an intracellular apoptosis inducer. Recently, the ROD motif has been used as an intracellular apoptosis inducer and been coupled to a somatostatin peptide (targeting somatostatin receptor-2) to examine the cytotoxic effect of the hybrid somatostatin peptide {RGD-Lys($^{111}$In-DTPA)-Tyr$^3$-Octreotate} (23-26). RGD-Lys ($^{111}$In-DTPA)-Tyr$^3$-Octreotate exhibited enhanced tumoricidal effects than $^{111}$In-DTPA-Tyr$^3$-octreotate and $^{111}$In-DTPA-RGD due to elevated tumor cell apoptosis (23), demonstrating the feasibility of employing the receptor-targeting peptides to target the RGD motif (as an intracellular apoptosis inducer) to cancer cells to enhance the synergistic therapeutic effectiveness of the radiolabeled hybrid peptides.

Favorable properties of radiolabeled α-MSH peptides, such as nanomolar MC1 receptor binding affinities, rapid internalization and extended retention, underscore the potential of employing the α-MSH peptides as effective delivery vehicles. We hypothesized that the unique metal-cyclized α-MSH peptide could serve as an effective delivery vehicle to specifically transport the RGD motif into melanoma cells to induce apoptosis. In this study, we synthesized and evaluated two novel RGD-conjugated α-MSH hybrid peptide {RGD-Lys-(Arg$^{11}$)CCMSH and RGD-Arg-(Arg$^{11}$)CCMSH} to examine our hypothesis. The RGD motif {cyclic(Arg-Gly-Asp-DTyr-Asp)} was coupled to [Cys$^{3,4,10}$, D-Phe$^7$, Arg$^{11}$] α-MSH$_{3-13}$ {(Arg$^{11}$)CCMSH} through Lys or Arg linker to generate RGD-Lys-(Arg$^{11}$)CCMSH. We determined the internalization and efflux, melanoma targeting and pharmacokinetic properties, SPECT/CT imaging of $^{99m}$Tc-labeled RGD-Lys-(Arg$^{11}$)CCMSH and RGD-Arg-(Arg$^{11}$)CCMSH in B16/F1 melanoma cells and B16/F1 melanoma-bearing mice to evaluate their potential for melanoma imaging and treatment.

BRIEF DESCRIPTION OF THE FIGURES

Figure Legends

BRIEF DESCRIPTION OF THE INVENTION

Introduction

Figure 8:
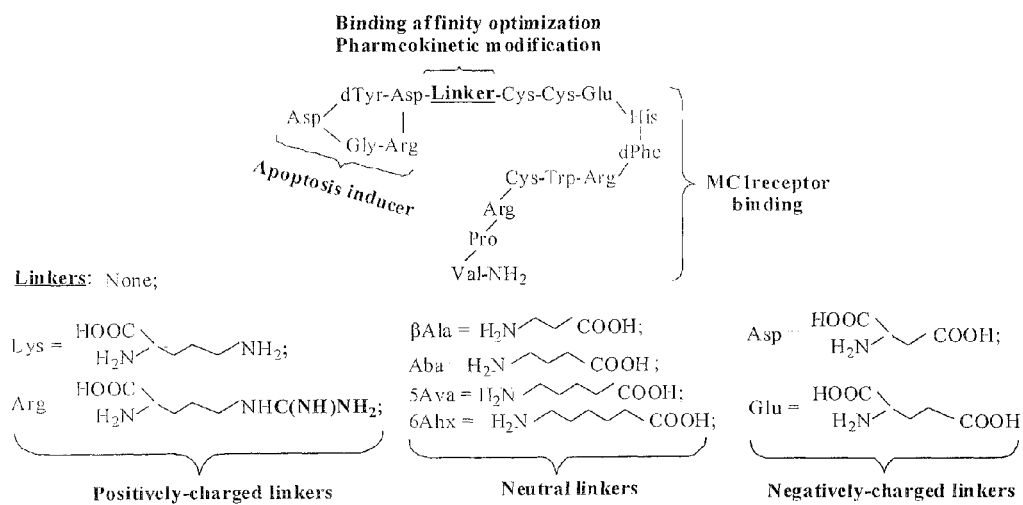
FIG. 8. Shows schematic structures of RGD-conjugated α-MSH compounds of the present invention.
Figure 9:
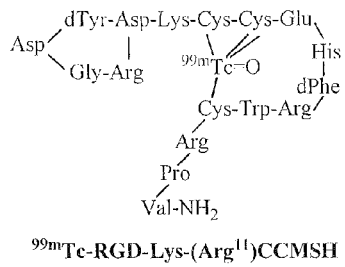
FIG. 9. Shows a schematic structure of a preferred embodiment of the present invention which chelates 99mTc.
Figure 10:
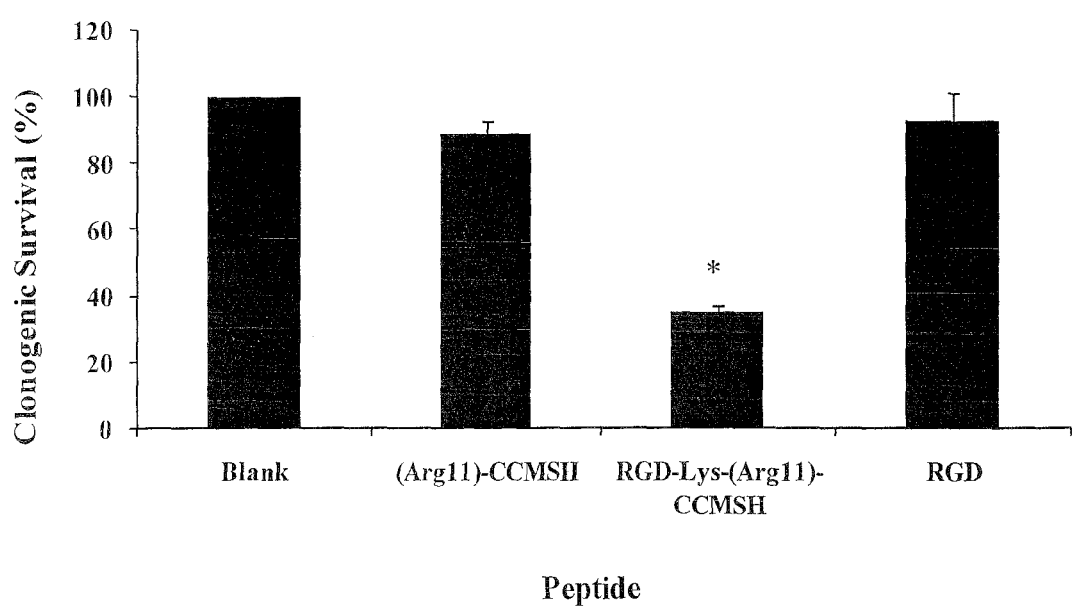
FIG. 10. Shows the clonogenic cytotoxic effect of RGD-Lys-(Arg11) CCMSH in B16/F1 melanoma cells. The cells were visually examined under microscope for survival. Colonies contained more than 50 cells were scored as survivors. *p<0.05, significance comparison between RGD-Lys-(Arg11)CCMSH treated cells and untreated cells (blank).

The present invention relates to compounds according to the general structure:

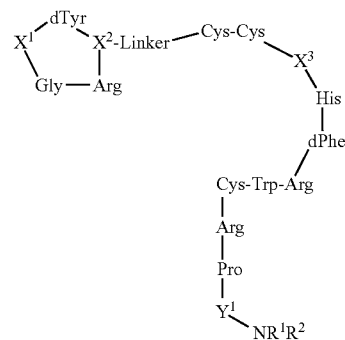

Where each of $X^1$, $X^2$ and $X^3$ is independently aspartic acid or glutamic acid, preferably aspartic acid (preferably all three of $X^1$, $X^2$ and $X^3$ are aspartic acid);

Linker is absent or is a positively-charged linker (preferably containing a pendant amino group), a neutral linker or a negatively charged linker (preferably containing a pendant carboxyl group) preferably obtained from an amino acid, preferably as depicted in FIG. 8 hereof, (e.g., lysine, arginine, beta-alanine, amino-butyric acid (Aba), 5-aminovaleric acid (5Ava), 6-aminohexanoic acid), aspartic acid or glutamic acid) or an oligopeptide containing from 2-5 amino acid residues in length wherein the oligopeptide comprises amino acid units which are obtained from lysine, arginine, beta-alanine, amino-butyric acid, 5-aminovaleric acid, 6-aminohexanoic acid, aspartic acid, glutamic acid or mixtures thereof) or a polyethylene glycol containing linker comprising from 1 to 20 ethylene glycol units, from 1 to 10 ethylene glycol units or from 1 to 4 ethylene glycol units;

$Y^1$ is valine, leucine or isoleucine, preferably valine; and $R^1$ and $R^2$ are each independently H, a $C_1$-$C_3$ alkyl group or a $C_1$ to $C_{20}$ acyl group, or a pharmaceutically acceptable salt thereof, optionally complexed or labeled with at least one radioisotope, preferably a polyvalent cationic radioisotope, even more preferably selected from the group consisting of $^{86}Y$, $^{90}Y$, $^{111}In$, $^{177}Lu$, $^{225}Ac$, $^{212}Bi$, $^{213}Bi$, $^{66}Ga$, $^{67}Ga$, $^{68}Ga$, $^{64}Cu$, $^{67}Cu$, $^{71}As$, $^{72}As$, $^{76}As$, $^{77}As$, $^{65}Zn$, $^{48}V$, $^{203}Pb$, $^{209}Pb$, $^{212}Pb$, $^{166}Ho$, $^{149}Pm$, $^{153}Sm$, $^{201}Tl$, $^{188}Re$, $^{186}Re$ and $^{99m}Tc$. Preferably, the compound is complexed with $^{99m}Tc$ or $^{99m}Tc=O$ as depicted in FIG. 9 hereof.

In preferred aspects of the invention, the polypeptide compound incorporates or is complexed with a radioisotope as otherwise described herein. In alternative preferred aspects, the linker is lysine or arginine (positive amino acid linkers), aspartic acid or glutamic acid (negatively charged amino acid linkers) or a neutral amino acid, preferably according to the chemical structure:

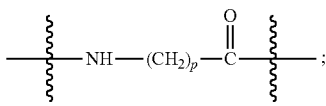

Where p is an integer from 0 to 20, preferably 1 to 12, more preferably 1 to 8. In still other embodiments, the linker is a polyethylene glycol containing linker comprising 1 to twenty ethylene glycol units, 1 to 10 ethylene glycol units, preferably 1 to 4 ethylene glycol units.

In still other preferred embodiments, compounds according to the present invention have the following chemical structure (lysine or arginine is the linker):

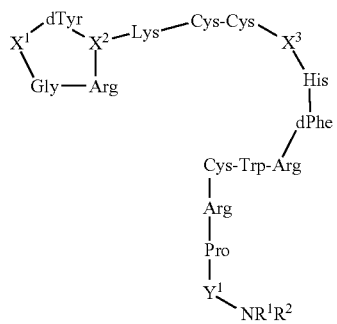

-continued

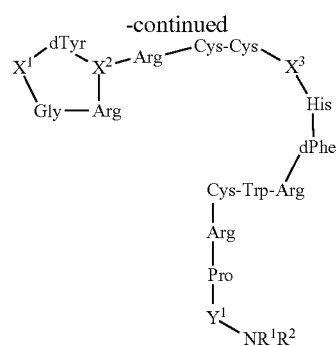

Where $X^1, X^2, X^3, Y^1, R^1$ and $R^2$ are the same as are presented above.

In alternative preferred embodiments, the present invention relates to the above compounds, including pharmaceutically acceptable salts, wherein the compound, especially the cyclic pentapeptide group, is complexed with a radioisotope (which may be a neutral species or a cationic species, and is preferably a polyvalent cationic species) selected from the group consisting of $^{86}Y$, $^{90}Y$, $^{111}In$, $^{177}Lu$, $^{225}Ac$, $^{212}Bi$, $^{213}Bi$, $^{66}Ga$, $^{67}Ga$, $^{68}Ga$, $^{64}Cu$, $^{67}Cu$, $^{71}As$, $^{72}As$, $^{76}As$, $^{77}As$, $^{65}Zn$, $^{48}V$, $^{203}Pb$, $^{212}Pb$, $^{166}Ho$, $^{149}Pm$, $^{153}Sm$, $^{201}Tl$, $^{188}Re$, $^{186}Re$, $^{99m}Tc$ and $^{99m}Tc=O$.

Radioisotopes to be complexed with the hybrid cyclic peptide of the present invention are selected based on the physical half life, the decay mode (alpha, beta, auger, gamma, X-ray) and the energy of the radioisotope. In diagnostic aspects of the present invention, preferred radioisotopes include, for example, $^{111}In$, $^{86}Y$, $^{66}Ga$, $^{67}Ga$, $^{68}Ga$, $^{203}Pb$, $^{64}Cu$, $^{99m}Tc$ and $^{99m}Tc=O$.

Where compounds are to be analyzed using positron emission tomography or PET imaging they are labeled with a positron emitting radioisotopes such as: $^{66}Ga$, $^{68}Ga$, $^{64}Cu$, $^{86}Y$, or other polyvalent, cationic radiometals that decay by positron emission. In alternative embodiments, the compounds may be analyzed using single photon emission computed tomography or SPECT imaging when labeled with a gamma radiation emitting radioisotope which preferably includes $^{111}In$, $^{67}Ga$, $^{99m}Tc$ and $^{203}Pb$ or other gamma emitting radioisotope as disclosed herein.

The present invention relates to compounds and/or compositions which may be used to prepare imaging/therapeutic agents or as imaging/therapeutic agents (when complexed with a radioisotope) for diagnosing and treating melanoma, including metastatic melanoma as otherwise described herein. Compounds according to the present invention which are complexed with an appropriate radioisotope may be used to diagnose the existence and/or extent of melanoma, including metastatic melanoma, monitor therapy as a therapeutic aid of melanoma, including metastatic melanoma, and in certain instances, function as a therapeutic agent (peptide targeted radiation) for the treatment of melanoma, including metastatic melanoma.

The present invention also relates to pharmaceutical compositions comprising an effective amount of a compound according to the present invention which has been complexed with a radioisotope and combined with a carrier, additive or excipient in pharmaceutical dosage form as a diagnostic imaging agent or as a therapeutic agent. Compositions according to the present invention are formulated in pharmaceutical dosage form for administration preferably by a parenteral, preferably an intravenous route. Compositions according to the present invention may also be formulated for administration via a topical route, directly to the skin. Oral compositions may also be formulated for use in the present invention.

In the diagnostic method according to the present invention, a compound according to the present invention which is complexed with a radioisotope as otherwise described, is administered to a patient, and evidence of elevated expression of MSH receptors in tissue of said patient through standard well-known nuclear imaging techniques, especially radiation (radionuclide) imaging, including scintigraphic imaging, and especially single photon emission computed tomography (SPECT) and positron emission tomography (PET) in comparison to a normal standard, is indicative of a disease state (melanoma) and extent of disease state (metastasis) in the tissue of the patient. The nuclear imaging techniques useful in the present diagnostic methods are well known in the art. In general, elevated levels of radiation emanating from a diagnosed tissue is evidence of elevated MSH receptor activity and indicative of a disease state or condition (melanoma and/or metastatic melanoma) wherein these receptors are found at elevated levels. Methods of diagnosing the existence and/or extent (stage) of melanoma, including metastatic melanoma are therefore additional aspects of the present invention. Thus, a diagnostic method of diagnosing the existence or absence of melanoma in a patient at risk for melanoma comprises administering to said patient a compound according to the present invention; imaging said patient to determine if tissue in said patient exhibits elevated expression of MSH receptors; and diagnosing said patient as having melanoma, including metastatic melanoma if said tissue evidences elevated expression of MSH receptors in comparison to a standard.

Methods of monitoring the treatment of melanoma, including metastatic melanoma in conjunction with traditional or experimental melanoma therapy is an additional aspect of the invention. In this aspect, a patient's response to therapy is monitored using the methods according to the present invention. In this method, a patient is monitored before and after therapy by administering compound according to the present invention and determining (through imaging diagnostics as otherwise described herein) the extent of expression of melanocyte stimulating hormone receptors in tissues of a patient before therapy and after therapy and comparing the expression levels with each other and/or with a standard (predetermined value) to determine the extent of reduction of cancer tissue which occurred pursuant to the therapeutic intervention.

Methods of treating melanoma represent a further aspect of the invention. In this aspect, compounds according to the present invention as described above are administered to a patient known to have melanoma and/or metastatic melanoma in effective amounts in order to reduce cancer tissue and otherwise treat the patient's cancer through targeted radiation therapy. The present therapeutic methods may be used alone or in combination with other treatment methods (surgery, chemotherapy, radiation therapy and/or immunotherapy (IL-2 and α-interferon) for melanoma/metastatic melanoma as otherwise disclosed herein. In preferred therapeutic method aspects of the present invention, compounds according to the present invention are labeled with $^{90}$Y, $^{177}$Lu, $^{186}$Re, $^{88}$Re, $^{212}$Bi/$^{212}$Pb, $^{213}$Bi, $^{149}$Pm, $^{166}$Ho and $^{153}$Sm and are administered to the patient (preferably intravenously or topically—i.e, directly onto the melanoma tissue in the skin of the patient) in order to target the malignant melanoma tumor, including metastatic melanoma tissue with radiation therapy.

In certain preferred methods according to the present invention, compounds which are described herein are coadministered with L-lysine, which has been shown to decrease the renal uptake of compounds according to the present invention, resulting in more favorable pharmacokinetics.

DETAILED DESCRIPTION OF THE INVENTION

The following terms are used to describe the present invention. In the event that a term is not specifically defined herein, that term is accorded its commonly understood meaning within the context of its use by those of ordinary skill in the art. It is understood that the definitions of the terms which are used to describe the present invention are interpreted in a manner consistent with the present invention and within the context of a particular term's use in describing the present invention in one or more embodiments.

As used herein and in the appended claims, the singular forms "a," "an," and "the" include plural reference unless the context clearly dictates otherwise. Thus, for example, a reference to "a compound", within context, includes a plurality (for example, two or more compounds) of such elements, and so forth. Under no circumstances is the patent be interpreted to be limited to the specific examples or embodiments or methods specifically disclosed herein.

The term "patient" or "subject" is used throughout the specification to describe an animal, preferably a human, to whom treatment, including prophylactic treatment, with the compounds according to the present invention is provided. For treatment of those infections, conditions or disease states which are specific for a specific animal such as a human patient, the term patient refers to that specific animal.

The term "compound" is used herein to refer to any specific chemical compound disclosed herein. Within its use in context, the term generally refers to a single oligopeptide, or an oligopeptide bonded to a DOTA group optionally complexed with a radioisotope, but in certain instances may also refer to components/portions of such compounds, intermediates used to synthesize such compounds, stereoisomers and/or optical isomers (including racemic mixtures) of disclosed compounds. The term compound shall include, where applicable, any and all relevant pharmaceutically acceptable salts thereof.

The term "neutral linker" refers to a linker which is uncharged. The linker may be an amino acid (neutral), an oligopeptide comprising neutral amino acids or a polyethylene glycol containing linker, as otherwise described herein.

The term "positively charged linker" refers to a linker which has at least one positive charge. Linkers which contain lysine and/or arginine generally are positively charged for purposes of the present invention.

The term "negatively charged linker" refers to a linker which has at least one negative charge. Linkers which contain aspartic acid and/or glutamic acid are negatively charged for purposes of the present invention.

The term "neutral amino acid" is an amino acid which has an uncharged sidechain at physiological pH. Neutral amino acids for use in the present invention include, for example, glycine, alanine, valine, leucine, isoleucine, norleucine, methionine, phenylalanine, serine, threonine and tyrosine. Preferred neutral amino acids include glycine, alanine, valine, leucine, isoleucine and norleucine, as well as amino acids according to the chemical structure:

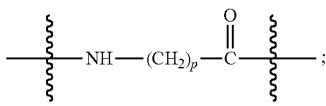

Where p is an integer from 0 to 20, preferably 1 to 12, more preferably 1 to 8. Exemplary amino acids according to this chemical structure include beta-alanine, amino-butyric acid (Aba), 5-aminovaleric acid (5Ava) and 6-aminohexanoic acid), amino others.

The term "negatively charged amino acid" is an amino acid which has a negatively charged sidechain at physiological pH. Preferred negatively charged amino acids for use in the present invention include glutamic acid and aspartic acid, both of which contain a plurality of carboxylate anions (in contrast to free/protonated carboxylic acids) at physiological pH.

The term "positively charged amino acid is an amino acid which has a positively charged sidechain at physiological pH. Preferred positively charged amino acids for use in the present invention include lysine and arginine, both of which contain amino groups in the side chain which are protonated at physiological pH (see FIG. 8).

The term "polyethylene glycol containing linker" is used to refer to a linker as otherwise described herein which contains from 1 to 20 ethylene glycol units. The linker is synthesized preferably to enable the formation of an amide group at either end of the linker with the polypeptide to which it is attached. A preferred polyethylene glycol containing linker is according to the chemical structure:

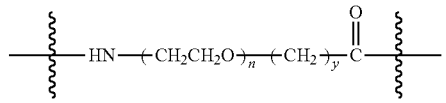

Where n is 1 to 20, 1 to 10, 1 to 4; and
y is 1 to 4

The term "hybrid peptide", "HYBpeptide". "hybrid MSH peptide", or "HYBMSH" refers to cyclic peptides compounds which contain a cyclic peptide which optionally binds a radioisotope according to the present invention. Cyclic peptides according to the present invention may be represented by the chemical structure

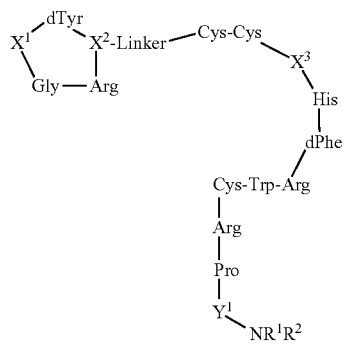

Where each of $X^1$, $X^2$ and $X^3$ is independently aspartic acid or glutamic acid, preferably aspartic acid (preferably all three of $X^1$, $X^2$ and $X^3$ are aspartic acid);
Linker is a positive, negative or neutral amino acid;
$Y^1$ is valine, leucine or isoleucine, preferably valine; and
$R^1$ and $R^2$ are each independently H, a $C_1$-$C_3$ alkyl group or a $C_1$ to $C_{20}$ acyl group,
or a pharmaceutically acceptable salt thereof, optionally complexed or labeled with at least one radioisotope, preferably a polyvalent cationic radioisotope, even more preferably selected from the group consisting of $^{86}$Y, $^{90}$Y, $^{111}$In, $^{177}$Lu, $^{225}$Ac, $^{212}$Bi, $^{213}$Bi, $^{66}$Ga, $^{67}$Ga, $^{68}$Ga, $^{64}$Cu, $^{67}$Cu, $^{71}$As, $^{72}$As, $^{76}$As, $^{77}$As, $^{65}$Zn, $^{48}$V, $^{203}$Pb, $^{209}$Pb, $^{212}$Pb, $^{166}$Ho, $^{149}$Pm, $^{153}$Sm, $^{201}$Tl, $^{188}$Re, $^{186}$Re, $^{99m}$Tc and $^{99m}$mTc=O.

Cyclic peptides according to the present invention are preferably represented by the following chemical structure (the linker is preferably lysine):

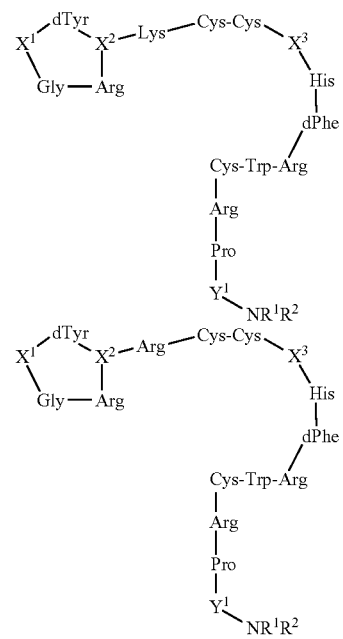

Where each of $X^1$, $X^2$ and $X^3$ is independently aspartic acid or glutamic acid, preferably aspartic acid (preferably all three of $X^1$, $X^2$ and $X^3$ are aspartic acid); and
$Y^1$ is valine, leucine or isoleucine, preferably valine;
$R^1$ and $R^2$ are each independently H, a $C_1$-$C_3$ alkyl group or a $C_1$ to $C_{20}$ acyl group,
or a pharmaceutically acceptable salt thereof, wherein said compound is optionally complexed to or labeled with a radioisotope as otherwise described herein. These compounds (i.e., those complexed with a radioisotope as otherwise described herein) are useful in the diagnosis and therapy of melanoma, especially including metastatic melanoma.

In preferred aspects of the present invention, $X^1$, $X^2$ and $X^3$ are each aspartic acid, $Y^1$ is valine and $R^1$ and $R^2$ are each H, or a pharmaceutically acceptable salt thereof.

The term "radical" is used to describe a group which is covalently bonded to another group in compounds according to the present invention.

The term "acylated" is used to describe an acyl group which may be used, where appropriate, at a terminal amine group of compounds of the present invention. The term "acyl" is used throughout the specification to describe a group at a terminal amine position of an amino acid which contains a $C_0$ to $C_{20}$ (preferably a $C_1$ to $C_{20}$) linear, branched or cyclic alkyl chain (a $C_0$ group is substituted with H). The acyl group at a terminal amine position, results in an amide linkage, which, after administration, may be cleaved. Acyl groups according to the present invention are represented by the structure:

where $R_4$ is a $C_0$ to $C_{20}$ (preferably, a $C_1$ to $C_{20}$) linear, branched or cyclic alkyl group, phenoxymethyl, aryl, alkoxy, alkoxyalkyl, aryloxyalkyl, alkoxycarbonyloxy groups (e.g., [(isopropoxycarbonyl)oxy]-methoxy), aryloxyalkyl, among others, all of which groups may be optionally substituted. Preferred acyl groups are those where $R_4$ is a $C_1$ to $C_{10}$ alkyl group. Acyl groups according to the present invention also include, for example, those acyl groups derived from benzoic acid and related acids, 3-chlorobenzoic acid, succinic, capric and caproic, lauric, myristic, palmitic, stearic and oleic groups, among numerous others. One of ordinary skill in the art will recognize the acyl groups which will have utility in the present invention, either to synthesize the target pharmaceutical compounds or as prodrug forms of the nucleosides according to the present invention.

The term "melanoma" is used to describe a malignant tumor of melanocytes which are found predominantly in skin but also in the bowel and the eye (see uveal melanoma), even though melanoma can be found in any part of the body. Melanoma is a form of cancer that begins in melanocytes, the cells that make skin pigment, or melanin. It may begin in a mole (skin melanoma), but can also begin in other pigmented tissues. There are several types of melanoma, defined by where they first appear, including skin and eye melanoma and in rare instances in the GI tract or lymph nodes Melanoma is one of the rarer types of skin cancer but causes the majority of skin cancer related deaths. Malignant melanoma is a serious type of skin cancer. It is due to uncontrolled growth of pigment cells, called melanocytes. Despite many years of intensive laboratory and clinical research, the sole effective cure is surgical resection of the primary tumor before it achieves a Breslow thickness greater than 1 mm.

Around 160,000 new cases of melanoma are diagnosed worldwide each year. About 48,000 melanoma related deaths occur worldwide per year. Malignant melanoma accounts for 75 percent of all deaths associated with skin cancer. The treatment includes surgical removal of the tumor; adjuvant treatment; chemo- and immunotherapy, or radiation therapy. The severity of melanoma is often characterized by the Clark level, which are for thin tumors and describe how deeply the cancer has spread into the skin, and the Breslow depth, which refers to the microscopic depth of tumor invasion.

The following stages are identified in the progression of the melanoma disease state. Melanoma progresses from an early stage (in situ) through an invasive stage, a high risk melanoma stage, a regional metastatic stage and a distant metastatic stage with varying degrees of survivability, as set forth below.

Melanoma Stages:
Stage 0: Melanoma in Situ (Clark Level I), 99.9% Survival
Stage I/II: Invasive Melanoma, 85-95% Survival
   T1a: Less than 1.00 mm primary, w/o Ulceration, Clark Level II-III
   T1b: Less than 1.00 mm primary, w/Ulceration or Clark Level IV-V
   T2a: 1.00-2.00 mm primary, w/o Ulceration
Stage II: High Risk Melanoma, 40-85% Survival
   T2b: 1.00-2.00 mm primary, w/Ulceration
   T3a: 2.00-4.00 mm primary, w/o Ulceration
   T3b: 2.00-4.00 mm primary, w/Ulceration
   T4a: 4.00 mm or greater primary w/o Ulceration
   T4b: 4.00 mm or greater primary w/Ulceration
Stage III: Regional Metastasis, 25-60% Survival
   N1: Single Positive Lymph Node
   N2: 2-3 Positive Lymph Nodes OR Regional Skin/In-Transit Metastasis
   N3: 4 Positive Lymph Nodes OR Lymph Node and Regional Skin/In Transit Metastases
Stage IV: Distant Metastasis, 9-15% Survival
   M1a: Distant Skin Metastasis, Normal LDH
   M1b: Lung Metastasis, Normal LDH
   M1c: Other Distant Metastasis OR Any Distant Metastasis with Elevated LDH
Based Upon AJCC 5-Year Survival With Proper Treatment Tradition therapy of melanoma involves a number of treatment options. These generally include surgery, chemotherapy, radiation therapy and immunotherapy (IL-2, other). In the case of surgery, treatment can vary and can include local excision, wide local excision, lymphadenectomy, sentinel lymph node biopsy and skin grafting. In the case of chemotherapy, a standard chemotherapeutic agent dacarbazine (DTIC) is administered to the patient in order to treat the cancer, generally through cancer cell death. In the case of radiation therapy, radiation is used as a palliative rather than a cure for melanoma. Radiation relieves bone pain and other symptoms caused by metastases to the bones, brain, and organs such as the liver. Although not curative, radiation treatment is being investigated for more widespread use in controlling other symptoms of skin cancer. In the case of immunotherapy (biologic treatment), a patient's natural immune system is raised or other immune compositions (IL-2) are administered to the patient against the cancer.

"Metastatic melanoma" refers to a progressed form of melanoma wherein the original cancer has metastasized to another area of the skin (regional or distant) or to other non-skin tissue (e.g., lungs, liver, brain, lymph system). Metastatic melanoma describes when melanoma has spread into surrounding healthy tissue and through the bloodstream, or lymphatic system, to other parts of the body. If melanoma spreads to these other areas, the cancer cells in the new tumor are still melanoma cells but the disease is called metastatic melanoma.

Unlike early stages of melanoma, which can be treated successfully with early diagnosis, the prognosis for patients diagnosed with metastatic melanoma is poor, with survival rates of six to nine months. In the past 35 years, the FDA has only approved two types of therapies for metastatic melanoma—interleukin 2 (IL-2) and DTIC. The methods of treatment for metastatic melanoma include radiation, immunotherapy, chemotherapy and palliative surgery. Currently, there are no approved therapies that significantly improve survival for patients with metastatic melanoma.

The term "imaging", "molecular imaging" or "radioimaging is used to describe methods that use the nuclear properties of matter in diagnosis and therapy, pursuant to the present invention. More specifically, the present invention relies on molecular imaging because it produces images that reflect biological processes that take place at the cellular and subcellular level.

Molecular imaging is a discipline that unites molecular biology and in vivo imaging. It enables the visualisation of the cellular function and the follow-up of the molecular process in living organisms without perturbing them. The multiple and numerous potentialities of this field are applicable to the diagnosis and treatment of diseases such as cancer, in the present invention, in particular, melanoma, including metastatic melanoma. This technique also contributes to improving the treatment of these disorders by optimizing the preclinical and clinical tests of new medication. This approach also has a major economic impact due to earlier and more precise diagnosis.

Molecular imaging differs from traditional imaging in that probes labeled biomarkers are used to help image particular targets or pathways. Biomarkers interact chemically with their surroundings and in turn alter the image according to molecular changes occurring within the area of interest. This process is markedly different from previous methods of imaging which primarily imaged differences in qualities such as density or water content. This ability to image fine molecular changes opens up an incredible number of exciting possibilities for medical application, including early detection and treatment of disease, in particular, melanoma and metastatic melanoma according to the present invention.

There are a number of different imaging modalities that can be used for noninvasive molecular imaging, using compounds according to the present invention. Each have different strengths and weaknesses and some are more adept at imaging multiple targets or sites than others. This is important in instances where metastatic melanoma is suspected. The modalities which can be used in the present invention are varied and in the present invention principally include single photon emission computed tomography (SPECT) and positron emission tomography (PET), discussed below.

The main purpose of SPECT when used in melanoma imaging pursuant to the present invention is to measure the distribution of radioisotope in skin tissue, in particular, those skin regions and other tissues where melanoma, including metastatic melanoma, is suspected. The development of computed tomography in the 1970s allowed mapping of the distribution of the radioisotopes in tissue, and led to the technique now called SPECT.

The imaging agent used in SPECT emits gamma rays, as opposed to the positron emitters used in PET. There are a number of radioisotopes (such as $^{99m}$Tc, $^{111}$In, $^{123}$I, $^{201}$Tl, $^{67}$Ga, $^{99m}$Tc and $^{203}$Pb, among other gamma ray emitters) that can be used in the present invention and imaged with SPECT technology. In SPECT, where possible, by rotating the gamma camera around the area to be analysed, a three dimensional image of the distribution of the radiotracer may be obtained by employing filtered back projection or other tomographic techniques. The radioisotopes used in SPECT have relatively long half lives (a few hours to a few days) making them easy to produce and relatively cheap in comparison to other radioisotopes. This represents the major advantage of SPECT as an imaging technique, since it is significantly cheaper than PET or other imaging methods such as magnetic resonance imaging (MRI). However, SPECT sometimes lacks exceptional spatial (i.e., where exactly the particle is) or temporal (i.e., did the contrast agent signal happen at a particular millisecond or not) resolution.

Another imaging technique which finds particular use in the present invention is positron emission tomography (PET). In PET, a molecule is tagged with a positron emitting isotope. These positrons (β particles) interact with nearby electrons, emitting two 511,000 eV photons, directed 180 degrees apart in opposite directions. These photons are then detected by the scanner which can estimate the density of positron annihilations in a specific area. When enough interactions and annihilations have occurred, the density of the original molecule may be measured in that area. Typical isotopes include $^{11}$C, $^{13}$N, $^{15}$O, $^{18}$F, $^{64}$Cu, $^{62}$Cu, $^{124}$I, $^{76}$Br, $^{82}$Rb and $^{68}$Ga, among others, including the preferred $^{66}$Ga, $^{68}$Ga, $^{64}$Cu, $^{86}$Y. One of the major disadvantages of PET is that most of the radioisotopes must be made with a cyclotron, thus making the use of PET, in certain instances prohibitively expensive. Most of these probes also have a half life measured in minutes and hours, thus forcing the cyclotron, in many instances, to be on site. These factors can make PET sometimes prohibitively expensive, except in certain cases, which the present invention addresses in certain aspects. PET imaging does have many advantages though. First and foremost is its sensitivity: a typical PET scanner can detect between $10^{-11}$ mol/L to $10^{-12}$ mol/L concentrations.

The term "effective" is used, to describe an amount of a compound, component or composition, which produces an intended effect when used within the context of its use, which may be a diagnostic method, a therapeutic method, a method to monitor the progression of therapy or other method (chemical synthesis) pursuant to the present invention. In the case of therapeutic methods, an effective amount for treating melanoma, including metastatic melanoma, is that amount which shrinks cancerous tissue (e.g., tumor), produces a remission, prevents further growth of the tumor and/or reduces the likelihood that the cancer in its early stages (in situ or invasive) does not progress further to metastatic melanoma.

Noted here is that within the context of the use of the present invention, the patient will be receiving a radiation dose, which provides guidance to the amount of compound which is considered effective when used within the context of its use. A patient undergoing a nuclear medicine procedure will receive a radiation dose. Under present international guidelines it is assumed that any radiation dose, however small, presents a risk. The radiation doses delivered to a patient in a nuclear medicine investigation present a very small risk of side effects, including inducing cancer in the patient. In this respect it is similar to the risk from X-ray investigations except that the dose is delivered internally rather than from an external source such as an X-ray machine.

The radiation dose from a diagnostic nuclear medicine procedure is expressed as an effective dose with units of sieverts (usually given in millisieverts, mSv). The effective dose resulting from an investigation is influenced by the amount of radioactivity administered in megabecquerels (MBq), the physical properties of the radiopharmaceutical used, its distribution in the body and its rate of clearance from the body.

Effective doses can range from 6 μSv (0.006 mSv) for a 3 MBq chromium-51 EDTA measurement of glomerular filtration rate to 37 mSv or more for a 150 MBq thallium-201 non-specific tumour imaging procedure. The common bone scan with 600 MBq of technetium-99m-MDP has an effective dose of 3 mSv. Formerly, units of measurement were the Curie (Ci), being 3.7E10 Bq, and also 1.0 grams of radium (Ra-226); the rad (radiation absorbed dose), now replaced by the Gray; and the rem (röntgen equivalent man), now replaced with the Sievert. The rad and rem are essentially equivalent for almost all nuclear medicine procedures, and only alpha radiation will produce a higher Rem or Sv value, due to its much higher relative biological effectiveness (RBE).

The term "coadministration" or "combination therapy" is used to describe a therapy in which at least two active compounds (one of which is a compound according to the present invention) in effective amounts are used to treat melanoma, including metastatic melanoma as otherwise described herein at the same time. Although the term coadministration preferably includes the administration of two active compounds to the patient at the same time, it is not necessary that the compounds be administered to the patient at the same time, although effective amounts of the individual compounds will be present in the patient at the same time. Compounds according to the present invention may be administered with one or more compound including a chemotherapeutic agent such as dacarbazine (DTIC) and/or and immunotherapeutic agent such as IL-2 and/or α-interferon, among other compounds.

The term "treating" or "successfully treating" when used in the context of treating melanoma, including metastatic melanoma, shall include shrinking a tumor, curing melanoma, including melanoma which has metastasized (by causing a remission of the cancer in the patient) or reducing the likelihood or preventing the spread of the melanoma into other organs. Melanoma, including metastatic melanoma, may be treated using compounds according to the present invention alone, or in combination with other methods and/or compounds including surgery, chemotherapy (especially the use of the chemotherapeutic agent dacarbazine or DTIC), radiation therapy (i.e., with agents other than the present therapeutic compositions) and immunotherapy (IL-2 and/or α-interferon).

In preferred aspects of the present invention, the radioisotope which is complexed or labeled to the hybrid peptide (HYPpeptide) of the present invention is selected from the group consisting of $^{111}$In, $^{86}$Y, $^{66}$Ga, $^{67}$Ga, $^{68}$Ga, $^{203}$Pb, $^{64}$Cu and $^{99m}$Tc when the compounds are to be used diagnostically or to monitor therapeutic intervention and the radioisotope is selected from the group consisting of $^{90}$Y, $^{177}$Lu, $^{186}$Re, $^{188}$Re, $^{212}$Bi/$^{212}$Pb, $^{213}$Bi, $^{149}$Pm, $^{166}$Ho and $^{153}$Sm when compounds according to the present invention are used in radiation therapy to treat melanoma, including metastatic melanoma.

The present invention also relates to pharmaceutical compositions comprising an effective amount of a compound for diagnostic and/or therapeutic purposes in combination with a pharmaceutically acceptable carrier, additive or excipient in pharmaceutical dosage form. For diagnostic purposes pharmaceutical compositions are formulated generally in parenteral dosage form, especially for intravenous administration, although oral or topical formulations may be useful in certain instances. In the case of the use of compounds according to the present invention for therapeutic purposes, the compositions are formulated preferably in parenteral or topical dosage forms, although orally administered dosage forms are also useful.

The compounds of the present invention, may, in accordance with the invention, be administered in single or divided doses by the oral, parenteral or topical routes. Administration of the active compound may range from a single intravenous injection to continuous (intravenous drip) to several oral administrations per day (for example, Q.I.D.) and may include oral, topical, parenteral, intramuscular, intravenous, sub-cutaneous, transdermal (which may include a penetration enhancement agent), buccal, sublingual and suppository administration, among other routes of administration. Enteric coated oral tablets may also be used to enhance bioavailability of the compounds from an oral route of administration. The most effective dosage form will depend upon the pharmacokinetics of the particular agent chosen as well as the severity of disease in the patient. Administration of compounds according to the present invention as sprays, mists, or aerosols for intra-nasal, intra-tracheal or pulmonary administration may also be used. The present invention therefore also is directed to pharmaceutical compositions comprising an effective amount of compound according to the present invention, optionally in combination with a pharmaceutically acceptable carrier, additive or excipient.

The amount of compound used is that amount effective within the context of the administration, whether that administration is for diagnostic purposes or therapeutic purposes. A suitable oral dosage for a compound according to the present invention would be in the range of about 0.01 mg to 10 g or more per day, preferably about 0.1 mg to about 1 g per day. In parenteral formulations, a suitable dosage unit may contain from 0.1 to 250 mg of said compounds, which may be administered from one to four times per day (for diagnostic purpose, preferably once in a bolus dose), whereas for topical administration, formulations containing 0.01 to 1% active ingredient are preferred. It should be understood, however, that the dosage administration from patient to patient will vary and the dosage for any particular patient will depend upon the clinician's judgment, who will use as criteria for fixing a proper dosage the size and condition of the patient as well as the patient's response to the drug.

When the compounds of the present invention are to be administered by the oral route, they may be administered as medicaments in the form of pharmaceutical preparations which contain them in association with a compatible pharmaceutical carrier, additive or excipient material. Such carrier material can be an inert organic or inorganic carrier material suitable for oral administration. Examples of such carrier materials are water, gelatin, talc, starch, magnesium stearate, gum arabic, vegetable oils, polyalkylene-glycols, petroleum jelly and the like.

The pharmaceutical preparations can be prepared in a conventional manner and finished dosage forms can be solid dosage forms, for example, tablets, dragees, capsules, and the like, or liquid dosage forms, for example solutions, suspensions, emulsions and the like.

The pharmaceutical preparations may be subjected to conventional pharmaceutical operations such as sterilization. Further, the pharmaceutical preparations may contain conventional adjuvants such as preservatives, stabilizers, emulsifiers, flavor-improvers, wetting agents, buffers, salts for varying the osmotic pressure and the like. Solid carrier material which can be used include, for example, starch, lactose, mannitol, methyl cellulose, microcrystalline cellulose, talc, silica, dibasic calcium phosphate, and high molecular weight polymers (such as polyethylene glycol).

For parenteral use, a compound according to the present invention can be administered in an aqueous or non-aqueous solution, suspension or emulsion in a pharmaceutically acceptable oil or a mixture of liquids, which may contain bacteriostatic agents, antioxidants, preservatives, buffers or other solutes to render the solution isotonic with the blood, thickening agents, suspending agents or other pharmaceutically acceptable additives. Additives of this type include, for example, tartrate, citrate and acetate buffers, ethanol, propylene glycol, polyethylene glycol, complex formers (such as EDTA), antioxidants (such as sodium bisulfate, sodium metabisulfite, and ascorbic acid), high molecular weight polymers (such as liquid polyethylene oxides) for viscosity regulation and polyethylene derivatives of sorbitol anhydrides. Preservatives may also be added if necessary, such as benzoic acid, methyl or propyl paraben, benzalkonium chloride and other quaternary ammonium compounds. In certain preferred diagnostic and/or therapeutic embodiments, compounds according to the present invention are administered intravenously in sterile saline solution.

The compounds of this invention may also be administered as solutions for nasal application and may contain in addition to the compounds of this invention suitable buffers, tonicity adjusters, microbial preservatives, antioxidants and viscosity-increasing agents in an aqueous vehicle. Examples of agents used to increase viscosity are polyvinyl alcohol, cellulose derivatives, polyvinylpyrrolidone, polysorbates or glycerin. Preservatives added may include benzalkonium chloride, chloro-butanol or phenylethyl alcohol, among numerous others.

Additionally, the compounds provided by the invention can be administered by suppository.

In certain aspects according to the present invention, where various cancers are to be treated, the compounds may be co-administered with at least one other anti-cancer agent such as dacarbazine (DTIC) or an immunotherapeutic agent such as IL-2 and/or α-interferon. In addition, compounds according to the present invention may be administered prior to, during or after surgery to remove melanoma tissue.

Preparation of compounds according to the present invention proceeds using standard synthetic chemical techniques which are readily available in the art. Synthetic methods for obtaining compounds related to the present invention may be found in the examples section of the present specification. These methods can serve as guides for obtaining compounds according to the present invention. The hybride peptide may be synthesized using common and well known peptide synthetic methods in the art. In general, the present compounds may be made by first synthesizing the hybrid peptide and thereafter the radionuclide may be complexed or labeled to the peptide (in particular, the cyclic pentapeptide).

Henry: radionuclide is attached to the CCMSH motif rather than RGD motif. Please see FIG. 9.

The radionuclide is generally complexed to the cyclic CCMSH motif group preferably after synthesis of the entire hybrid peptide. See FIG. 9. The hybrid peptide is synthesized using conventional peptide synthesis (as otherwise described in the examples section or using methods readily available in the art using protecting group chemistry). The lactam coupling between the lysine amino acid and the amino acid (aspartic acid or glutamic acid) within the cyclic peptide group of the HYPpeptide is readily performed using methods described herein or as otherwise as readily known in the art.

Once the compounds are synthesized, they may be formulated in pharmaceutical dosage form using convention pharmaceutical formulation methods readily available in the art by simply admixing compounds with chosen carriers, additives and/or excipients, depending upon the dosage form to be used and depending upon the use (diagnostic or therapeutic) of the compositions.

It is highly desirable to develop novel and effective therapeutic agents for melanoma treatment. The purpose of the following study was to determine whether Arg-Gly-Asp (RGD)-conjugated alpha-melanocyte stimulating hormone (α-MSH) hybrid peptide could be employed to target melanocortin-1 (MC1) receptor for potential melanoma therapy. In the following two examples, the RGD motif {cyclic(Arg-Gly-Asp-DTyr-Asp)} was coupled to [Cys$^{3,4,10}$, D-Phe$^7$, Arg$^{11}$]α-MSH$_{3-13}$ {(Arg$^{11}$)CCMSH} through Lys or Arg linker to generate RGD-Lys-(Arg$^{11}$)CCMSH and RGD-Arg-(Arg$^{11}$)CCMSH hybrid peptides. The MC1 receptor binding affinities of RGD-Lys-(Arg$^{11}$)CCMSH and RGD-Arg-(Arg$^{11}$)CCMSH were determined in B16/F1 melanoma cells. The internalization and efflux, melanoma targeting and pharmacokinetic properties and SPECT/CT imaging of $^{99m}$Tc-RGD-Lys-(Arg$^{11}$)CCMSH and $^{99m}$Tc-RGD-Arg-(Arg$^{11}$) CCMSH were determined in B16/F1 melanoma cells and melanoma-bearing C57 mice.

The results showed that RGD-Lys-(Arg$^{11}$)CCMSH displayed 2.1 nM MC1 receptor binding affinity in B16/F1 cells. $^{99m}$Tc-RGD-Lys-(Arg$^{11}$)CCMSH was readily prepared with greater than 95% radiolabeling yield. $^{99m}$Tc-RGD-Lys-(Arg$^{11}$)CCMSH showed rapid internalization and extended retention in B16/F1 cells. The cellular uptake of $^{99m}$Tc-RGD-Lys-(Arg$^{11}$)CCMSH was MC1 receptor-mediated. $^{99m}$Tc-RGD-Lys-(Arg$^{11}$)CCMSH exhibited high tumor uptake (14.83±2.94% ID/g 2 h post-injection) and prolonged tumor retention (7.59±2.04% ID/g 24 h post-injection) in B16/F1 melanoma-bearing mice. Non-target organ uptakes were generally low except for the kidneys. Flank melanoma tumors were clearly imaged by small animal SPECT/CT using $^{99m}$Tc-RGD-Lys-(Arg$^{11}$)CCMSH as an imaging probe 2 h post-injection.

The results showed that RGD-Arg-(Arg$^{11}$)CCMSH displayed 0.7 nM MC1 receptor binding affinity in B16/F1 cells. $^{99m}$Tc-RGD-Arg-(Arg$^{11}$)CCMSH was readily prepared with greater than 95% radiolabeling yield. $^{99m}$Tc-RGD-Arg-(Arg$^{11}$)CCMSH showed rapid internalization and extended retention in B16/F1 cells. The cellular uptake of $^{99m}$Tc-RGD-Arg-(Arg$^{11}$)CCMSH was MC1 receptor-mediated. Replacement of the Lys linker with Arg linker exhibited a profound effect in reducing the non-specific renal uptake of $^{99m}$Tc-RGD-Arg-(Arg$^{11}$)CCMSH, as well as increasing the tumor uptake of $^{99m}$Tc-RGD-Arg-(Arg$^{11}$)CCMSH compared to $^{99m}$Tc-RGD-Lys-(Arg$^{11}$)CCMSH. $^{99m}$Tc-RGD-Arg-(Arg$^{11}$) CCMSH exhibited high tumor uptake (21.41±3.74% ID/g at 2 h post-injection) and prolonged tumor retention (6.81±3.71% ID/g at 24 h post-injection) in B16/F1 melanoma-bearing mice. The renal uptake values of $^{99m}$Tc-RGD-Arg-(Arg$^{11}$)CCMSH were 40.14-64.08% of those of $^{99m}$Tc-RGD-Lys-(Arg$^{11}$)CCMSH (p<0.05) at 0.5, 2, 4 and 24 h post-injection. Co-injection of L-lysine was effective in decreasing the renal uptakes of $^{99m}$Tc-RGD-Arg-(Arg$^{11}$)CCMSH by 27.7% and $^{99m}$Tc-RGD-Lys-(Arg$^{11}$)CCMSH by 52.1% at 2 h post-injection. Flank melanoma tumors were clearly imaged by small animal SPECT/CT using $^{99m}$Tc-RGD-Arg-(Arg$^{11}$)CCMSH as an imaging probe 2 h post-injection.

Favorable melanoma targeting property of $^{99m}$Tc-RGD-Lys-(Arg$^{11}$)CCMSH and $^{99m}$Tc-RGD-Arg-(Arg$^{11}$)CCMSH warranted the further evaluation of $^{188}$Re-labeled α-MSH hybrid peptides as novel diagnostic and therapeutic peptides for melanoma treatment.

The following examples are provided to assist in describing the present invention. The details of these examples and the general description of the examples are for description purposes only and should be seen or taken to limit the scope of the invention in any way.

EXAMPLES $^{99m}$Tc-RGD-Lys-(Arg$^{11}$)CCMSH

Materials and Methods
Chemicals and Reagents

Amino acid and resin were purchased from Advanced ChemTech Inc. (Louisville, Ky.) and Novabiochem (San Diego, Calif.). $^{99m}$TcO$_4^-$ was purchased from Cardinal Health (Albuquerque, N. Mex.). $^{125}$I-Tyr$^2$-[Nle$^4$, D-Phe$^7$]-α-MSH {$^{125}$I-(Tyr$^2$)-NDP-MSH} was obtained from PerkinElmer, Inc. (Shelton, Conn.). All other chemicals used in this study were purchased from Thermo Fischer Scientific (Waltham, Mass.) and used without further purification. B16/F1 murine melanoma cells were obtained from American Type Culture Collection (Manassas, Va.).

Example 1a

Peptide Synthesis

Intermediate scaffold of H$_2$N-Arg(Pbf)-Gly-Asp(OtBu)-dTyr(tBu)-Asp(O-2-phenylisopropyl)-Lys(Boc)-Cys(Trt)-

Cys(Trt)-Glu(OtBu)-His(Trt)-DPhe-Arg(Pbf)-Trp(Boc)-Cys(Trt)-Arg(Pbf)-Pro-Val was synthesized on Sieber amide resin using standard 9-fluorenylmethyloxycarbonyl (Fmoc) chemistry by an Advanced ChemTech multiple-peptide synthesizer (Louisville, Ky.). A small aliquot of the scaffold material was cleaved and characterized by liquid chromatography-mass spectroscopy (LC-MS). The protecting group of 2-phenylisopropyl was removed and the peptide was cleaved from the resin treating with a mixture of 2.5% of trifluoroacetic acid (TFA) and 5% of triisopropylsilane. After the precipitation with ice-cold ether and characterization by LC-MS, the protected peptide was dissolved in $H_2O/AcCN$ (50:50) and lyophilized to remove the reagents such as TFA and triisopropylsilane. The protected peptide was further cyclized by coupling the carboxylic group from the Asp with the alpha amino group from the Arg at the N-terminus. The cyclization reaction was achieved by overnight reaction in DMF using benzotriazole-1-yl-oxy-tris-pyrrolidino-phosphonium-hexafluorophosphate (PyBOP) as a coupling agent in the presence of N,N-diisopropylethylamine (DIEA). After characterization by LC-MS, the cyclized protected peptide was dissolved in $H_2O/AcCN$ (50:50) and lyophilized to remove the reagents such as PyBOP and DIEA. The protecting groups were totally removed by treating with a mixture of trifluoroacetic acid (TFA), thioanisole, phenol, water, ethanedithiol and triisopropylsilane (87.5:2.5:2.5:2.5:2.5:2.5) for 2 h at room temperature (25° C.). The peptides were precipitated and washed with ice-cold ether for four times. The final products were purified by reverse phase-high performance liquid chromatography (RP-HPLC) and characterized by LC-MS.

Example 2A

In Vitro Competitive Binding Assay

The $IC_{50}$ value of RGD-Lys-$(Arg^{11})$CCMSH was determined according to our previously published procedure (27). B16/F1 cells were harvested and seeded into a 24-well cell culture plate ($5 \times 10^5$/well) and incubated at 37° C. overnight. After being washed with binding media (MEM with 25 mM HEPES, pH 7.4, 0.2% BSA, 0.3 mM 1,10-phenathroline), the cells were incubated at room temperature (25° C.) for 2 h with approximately 40,000 counts per minute (cpm) of $^{125}I$-$(Tyr^2)$-NDP-MSH in the presence of increasing concentrations ($10^{-12}$ to $10^{-5}$ M) of RGD-Lys-$(Arg^{11})$CCMSH in 0.3 ml of binding media. The reaction media were aspirated after the incubation. The cells were rinsed twice with 0.5 ml of ice-cold pH 7.4, 0.2% bovine serum albumin (BSA)/0.01 M phosphate buffered saline (PBS) and lysed in 0.5 ml of 1 N NaOH for 5 minutes. The activities associated with cells were measured in a Wallac 1480 automated gamma counter (PerkinElmer, NJ). The $IC_{50}$ value for the peptide was calculated by fitting the data with nonlinear regression using Prism software (GraphPad Software, La Jolla, Calif.).

Example 3A

Peptide Radiolabelling

RGD-Lys-$(Arg^{11})$CCMSH was radiolabeled with $^{99m}Tc$ via a glucoheptonate transchelation reaction using methods described previously (7). Briefly, 100 µl of 2 mg/ml $SnCl_2$ in 0.2 M glucoheptonate aqueous solution and 200 µl of fresh $^{99m}TcO_4^-$ solution (1-4 mCi) were added into a reaction vial and incubated at room temperature (25° C.) for 20 mM to form $^{99m}Tc$-glucoheptonate. Then, 10 µl of 1 mg/ml RGD-Lys-$(Arg^{11})$CCMSH aqueous solution was added into the reaction vial and the pH of the reaction mixture was adjusted to 8.5 with 0.1 M NaOH. The reaction mixture was incubated at 75° C. for 40 min. The radiolabeled peptide was purified to single species by Waters RP-HPLC (Milford, Mass.) on a Grace Vydac C-18 reverse phase analytic column (Deerfield, Ill.) using a 20 min gradient of 16-26% acetonitrile in 20 mM HCl aqueous solution at a flow rate of 1 mL/min. The purified peptide sample was purged with $N_2$ gas for 20 min to remove the acetonitrile. The pH of the final solution was adjusted to 5 with 0.1 N NaOH and normal saline for animal studies. The stability of $^{99m}Tc$-RGD-Lys-$(Arg^{11})$CCMSH was determined by incubation in mouse serum at 37° C. according to the published procedure (27) for various time periods, and monitored for degradation by RP-HPLC.

Example 4A

Cellular Internalization and Efflux of $^{99m}Tc$-RGD-Lys-$(Arg^{11})$CCMSH

Cellular internalization and efflux of $^{99m}Tc$-RGD-Lys-$(Arg^{11})$CCMSH was evaluated in B16/F1 cells as previously described by Miao et al (27). After being washed once with binding media, B16/F1 cells in 24-well cell culture plates were incubated at 25° C. for 20, 40, 60, 90 and 120 min (n=4) in the presence of approximately 200,000 cpm of HPLC purified $^{99m}Tc$-RGD-Lys-$(Arg^{11})$CCMSH. After incubation, the reaction media were aspirated and the cells were rinsed twice with 0.5 ml of ice-cold pH 7.4, 0.2% BSA/0.01 M PBS. Cellular internalization of $^{99m}Tc$-RGD-Lys-$(Arg^{11})$CCMSH was assessed by washing the cells with acidic buffer [40 mM sodium acetate (pH 4.5) containing 0.9% NaCl and 0.2% BSA] to remove the membrane-bound radioactivity. The remaining internalized radioactivity was obtained by lysing the cells with 0.5 ml of 1 N NaOH for 5 min. Membrane-bound and internalized $^{99m}Tc$ activities were counted in a gamma counter. Cellular efflux of $^{99m}Tc$-RGD-Lys-$(Arg^{11})$CCMSH was determined by incubating B16/F1 cells with $^{99m}Tc$-RGD-Lys-$(Arg^{11})$CCMSH for 2 h at 25° C., removing non-specific-bound radioactivity with $2 \times 0.5$ ml of ice-cold pH 7.4, 0.2% BSA/0.01 M PBS rinse, and monitoring radioactivity released into cell culture media. At time points of 20, 40, 60, 90 and 120 mM, the radioactivities in media, on cell surface and in cells were separately collected and counted in a gamma counter.

Example 5A

Specificity of Cellular Uptake of $^{99m}Tc$-RGD-Lys-$(Arg^{11})$CCMSH

The specificity of cell binding was determined by incubating $^{99m}Tc$-RGD-Lys-$(Arg^{11})$CCMSH with or without non-radioactive peptides. After being washed once with binding media, B16/F1 cells in 24-well cell culture plates were incubated with approximately 200,000 cpm of HPLC purified $^{99m}Tc$-RGD-Lys-$(Arg^{11})$CCMSH at 25° C. for 120 min (n=4) in the presence of 0.1 µM of RGD-Lys-$(Arg^{11})$CCMSH, NDP-MSH, $(Arg^{11})$CCMSH or RGD in 0.5 ml of binding media, respectively. The reaction media were aspirated after the incubation. The cells were rinsed twice with 0.5 ml of ice-cold pH 7.4, 0.2% BSA/0.01 M PBS and lysed in 0.5 ml of 1 N NaOH for 5 min. The activities associated with cells were measured in a gamma counter. Statistical analysis was performed using the Student's t-test for unpaired data. A 95% confidence level was chosen to determine the significance of $^{99m}Tc$-RGD-Lys-$(Arg^{11})$CCMSH cellular uptake with or without peptide blockade, with $p<0.05$ being significantly different.

Example 6A

Biodistribution Studies

All the animal studies were conducted in compliance with Institutional Animal Care and Use Committee approval. The pharmacokinetics of $^{99m}$Tc-RGD-Lys-(Arg$^{11}$)CCMSH was determined in B16/F1 melanoma-bearing C57 female mice (Harlan, Indianapolis, Ind.). C57 mice were subcutaneously inoculated on the right flank with $1\times10^6$ B16/F1 cells. The weight of tumors reached approximately 0.2 g 10 days post cell inoculation. Each melanoma-bearing mouse was injected with 0.037 MBq of $^{99m}$Tc-RGD-Lys-(Arg$^{11}$)CCMSH via the tail vein. Groups of 5 mice were sacrificed at 0.5, 2, 4 and 24 h post-injection, and tumors and organs of interest were harvested, weighed and counted. Blood values were taken as 6.5% of the whole-body weight. The MC1 receptor specificity of the tumor uptake was determined at 2 h post-injection by co-injecting $^{99m}$Tc-RGD-Lys-(Arg$^{11}$)CCMSH with 10 μg (6.1 nmol) of unlabeled NDP-MSH, a linear α-MSH peptide analogue with picomolar affinity for the MC1 receptors present on murine melanoma cells. The co-injection of 3.5 μg (6.1 nmol) of RGD peptide was performed to determine the $\alpha_v\beta_3$ integrin specificity of the tumor uptake 2 h post-injection. Statistical analysis was performed using the Student's t-test for unpaired data. A 95% confidence level was chosen to determine the significance between $^{99m}$Tc-RGD-Lys-(Arg$^{11}$)CCMSH with or without peptide blockade, with p<0.05 being significantly different.

Example 7A

Imaging Melanoma with $^{99m}$Tc-RGD-Lys-(Arg$^{11}$)CCMSH

A B16/F1 melanoma-bearing C57 mouse was injected with 10.4 MBq of $^{99m}$Tc-RGD-Lys-(Arg$^{11}$)CCMSH via the tail vein. The mouse was anesthetized with 1.5% isoflurane for small animal SPECT/CT (Nano-SPECT/CT®, Bioscan) imaging 2 h post-injection. The 9-min CT imaging was immediately followed by the SPECT imaging of whole-body. The SPECT scans of 24 projections were acquired and total acquisition time was approximately 45 min. After the SPECT imaging, the mouse was euthanized with $CO_2$ inhalation. Reconstructed data from SPECT and CT were visualized and co-registered using InVivoScope (Bioscan, Washington D.C.).

Example 8A

Urinary Metabolites of $^{99m}$Tc-RGD-Lys-(Arg$^{11}$)CCMSH

Urinary metabolites of $^{99m}$Tc-RGD-Lys-(Arg$^{11}$)CCMSH were determined by injecting 3.7 MBq of $^9$"Tc-RGD-Lys-(Arg$^{11}$)CCMSH into a B16/F1 melanoma-bearing C57 mouse through the tail vein. At 2 h after dose administration, the mouse was euthanized and the urine was collected. The radioactive metabolites in the urine were analyzed by injecting aliquots of urine into HPLC. A 20-minute gradient of 16-26% acetonitrile/20 mM HCl was used for the urine analysis.

Results

Figure 1:
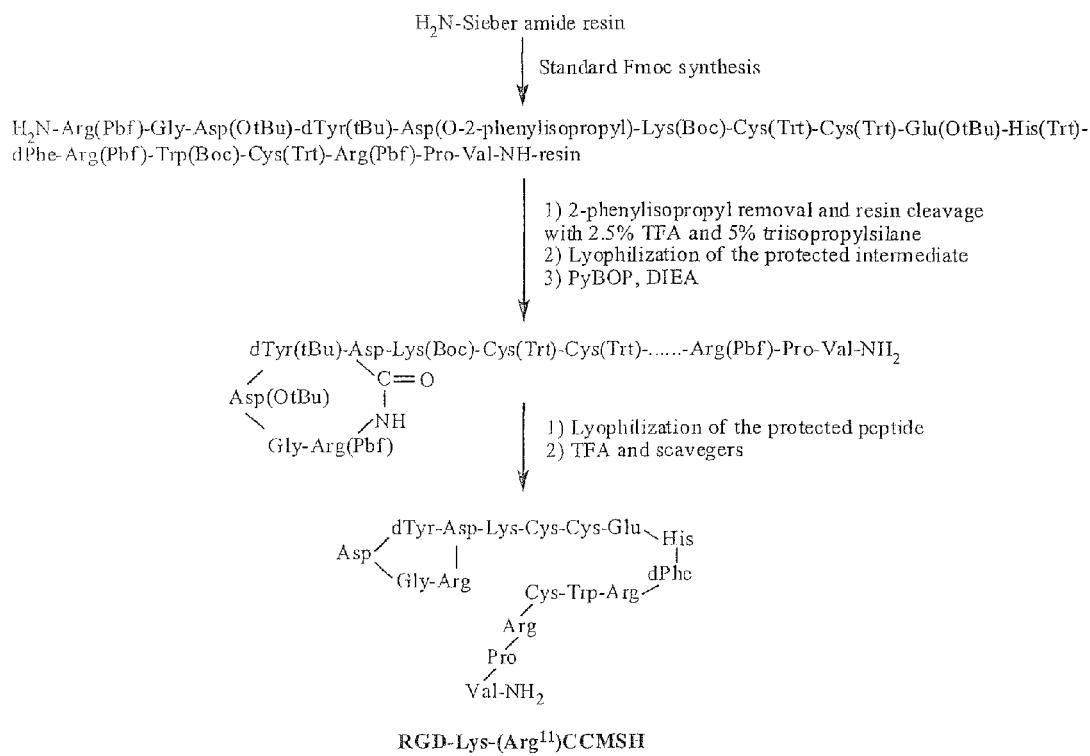
FIG. 1. Synthetic scheme for the production of RGD-Lys-(Arg$^{11}$)CCMSH.
Figure 2:
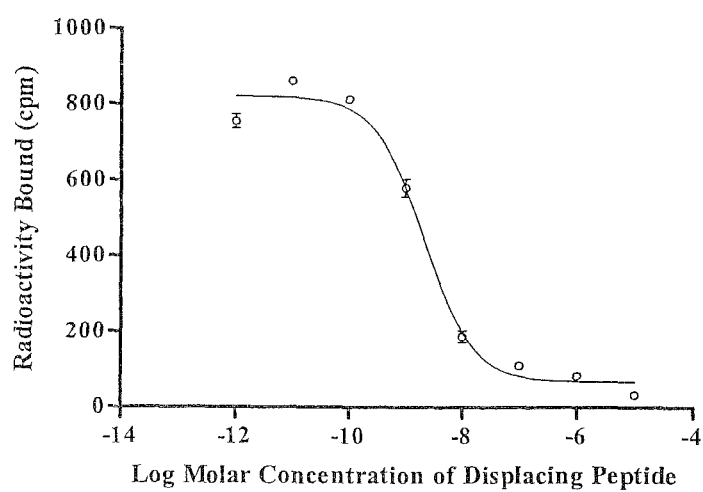
FIG. 2. The competitive binding curve of RGD-Lys-(Arg$^{11}$)CCMSH in B16/F1 murine melanoma cells. The IC$_{50}$ value of RGD-Lys-(Arg$^{11}$)CCMSH was 2.1 nM.
Figure 3:
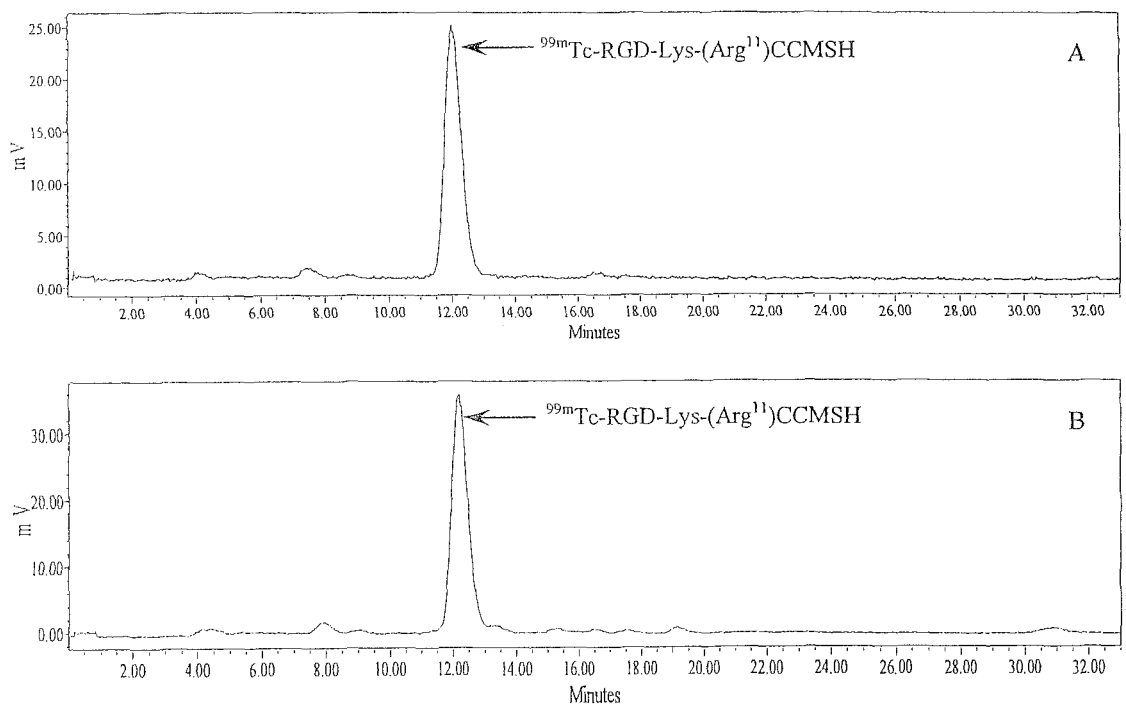
FIG. 3. HPLC profiles of radioactive $^{99m}$Tc-RGD-Lys-(Arg$^{11}$)CCMSH (A) and mouse serum stability of $^{99m}$Tc-RGD-Lys-(Arg$^{11}$)CCMSH (B) after 24 h incubation at 37° C. The retention time of $^{99m}$Tc-RGD-Lys-(Arg$^{11}$)CCMSH was 12.2 min.

RGD-Lys-(Arg$^{11}$)CCMSH was synthesized, purified by RP-HPLC and the identity of peptide was confirmed by electrospray ionization mass spectrometry. The synthetic scheme is presented in FIG. 1. The competitive binding curve of RGD-Lys-(Arg$^{11}$)CCMSH is shown in FIG. 2. The $IC_{50}$ value of RGD-Lys-(Arg$^{11}$)CCMSH was 2.1 nM in B16/F1 cells. The peptide was readily labeled with $^{99m}$Tc using a glucoheptonate transchelation reaction. The radiolabeling yield was greater than 95%. The retention time of $^{99m}$Tc-RGD-Lys-(Arg$^{11}$)CCMSH was 12.2 min. $^{99m}$Tc-RGD-Lys-(Arg$^{11}$)CCMSH was stable in mouse serum at 37° C. for 24 h. Only the $^{99m}$Tc-RGD-Lys-(Arg$^{11}$)CCMSH peptide was detected by RP-HPLC after 24 h of incubation (FIG. 3).

Figure 4:
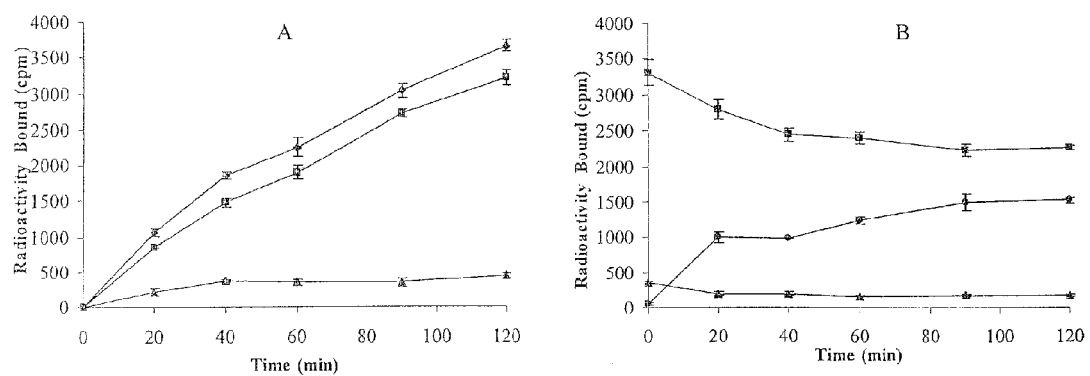
FIG. 4. Cellular internalization (A) and efflux (B) of $^{99m}$Tc-RGD-Lys-(Arg$^{11}$)CCMSH in B16/F1 murine melanoma cells at 25° C. Total bound radioactivity (♦), internalized activity (■), cell membrane activity (▲), and cell culture media activity (●) were presented as counts per minute (cpm).

Cellular internalization and efflux of $^{99m}$Tc-RGD-Lys-(Arg$^{11}$)CCMSH was evaluated in B16/F1 cells. FIG. 4 illustrates cellular internalization and efflux of $^{99m}$Tc-RGD-Lys-(Arg$^{11}$)CCMSH. $^{99m}$Tc-RGD-Lys-(Arg$^{11}$)CCMSH exhibited rapid cellular internalization and extended cellular retention. There was 76.28±1.36% of the $^{99m}$Tc-RGD-Lys-(Arg$^{11}$)CCMSH activity internalized in the B16/F1 cells 40 min post incubation. There was 85.93±1.22% of the $^{99m}$Tc-RGD-Lys-(Arg$^{11}$)CCMSH activity internalized in the cells after 2 h incubation. Cellular efflux results demonstrated that 68.57±3.77% of the $^{99m}$Tc-RGD-Lys-(Arg$^{11}$)CCMSH activity remained inside the cells 2 h after incubating cells in culture medium.

Figure 5:
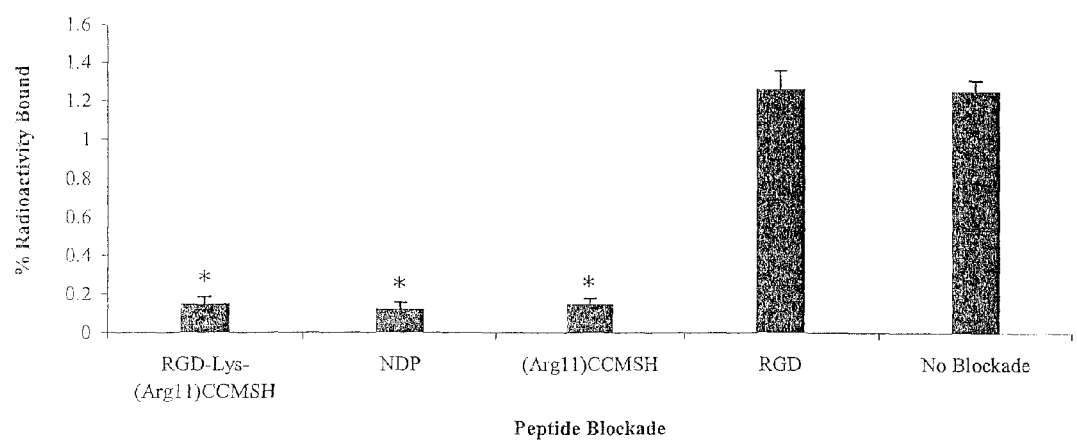
FIG. 5. Blocking studies of cellular uptake of $^{99m}$Tc-RGD-Lys-(Arg$^{11}$)CCMSH in B16/F1 murine melanoma cells. The cells were incubated with $^{99m}$Tc-RGD-Lys-(Arg$^{11}$)CCMSH in the presence of 0.1 μM of RGD-Lys-(Arg$^{11}$)—CCMSH, NDP-MSH, (Arg$^{11}$)CCMSH, RGD or no peptide blockade. *P<0.001.

Specificity of cellular uptake of $^{99m}$Tc-RGD-Lys-(Arg$^{11}$)CCMSH was examined in B16/F1 cells. The results are presented in FIG. 5. The cellular uptake of $^{99m}$Tc-RGD-Lys-(Arg$^{11}$)CCMSH was MC1 receptor-mediated rather than $\alpha_v\beta_3$ integrin-mediated. Compared to the cellular uptake of $^{99m}$Tc-RGD-Lys-(Arg$^{11}$)CCMSH without peptide blockade, the cellular uptakes of $^{99m}$Tc-RGD-Lys-(Arg$^{11}$)CCMSH decreased 88.1, 90.5 and 88.1% with 0.1 μM of RGD-Lys-(Arg$^{11}$)CCMSH, NDP-MSH and (Arg$^{11}$)CCMSH as blockades, respectively. Incubation of $^{99m}$Tc-RGD-Lys-(Arg$^{11}$)CCMSH with 0.1 μM of RGD didn't reduce the cellular uptake of $^{99m}$Tc-RGD-Lys-(Arg$^{I}$)CCMSH in B16/F1 cells.

The melanoma targeting and pharmacokinetic properties of $^{99m}$Tc-RGD-Lys-(Arg$^{11}$)CCMSH were determined in B16/F1 melanoma-bearing C57 mice. The biodistribution results of $^{99m}$Tc-RGD-Lys-(Arg$^{11}$)CCMSH are shown in Table 1. $^{99m}$Tc-RGD-Lys-(Arg$^{11}$)CCMSH exhibited rapid and high tumor uptake in melanoma-bearing mice. The tumor uptake value was 11.06±1.41% ID/g 0.5 h post-injection. $^{99m}$Tc-RGD-Lys-(Arg$^{11}$)CCMSH reached its peak tumor uptake value of 14.83±2.94% ID/g 2 h post-injection. There was 12.57±2.53% ID/g of the $^{99m}$Tc-RGD-Lys-(Arg$^{11}$)CCMSH activity remained in the tumors 4 h post-injection. The tumor uptake value of $^{99m}$Tc-RGD-Lys-(Arg$^{11}$)CCMSH gradually decreased to 7.59±2.04% ID/g 24 h post-injection. In melanoma uptake blocking studies, the tumor uptake of $^{99m}$Tc-RGD-Lys-(Arg$^{11}$)CCMSH with 10 μg (6.1 nmol) of non-radiolabeled NDP-MSH co-injection was only 12.2% of the tumor uptake without NDP-MSH co-injection at 2 h after dose administration (P<0.01), demonstrating that the tumor uptakes was specific and MC1 receptor-mediated. Compared to the tumor uptake of $^{99m}$Tc-RGD-Lys-(Arg$^{11}$)CCMSH, co-injection of $^{99m}$Tc-RGD-Lys-(Arg$^{11}$)CCMSH with 3.5 μg (6.1 nmol) of RGD decreased 29.2% of the tumor uptake value. Whole-body clearance of $^{99m}$Tc-RGD-Lys-(Arg$^{11}$)CCMSH was rapid, with approximately 62% of the injected radioactivity cleared through the urinary system by 2 h post-injection (Table 1). Normal organ uptakes of $^{99m}$Tc-RGD-Lys-(Arg$^{11}$)CCMSH were generally low (<3.2% ID/g) except for the kidneys after 2 h post-injection. High tumor/blood and tumor/muscle uptake ratios were demonstrated as early as 0.5 h post-injection (Table 1). The renal uptake of $^{99m}$Tc-RGD-Lys-(Arg$^{11}$)CCMSH reached its peak value of 69.37±5.37% ID/g 0.5 h post-injection. The renal uptake decreased to 40.26±10.83% ID/g 24 h post-injection.

Figure 6:
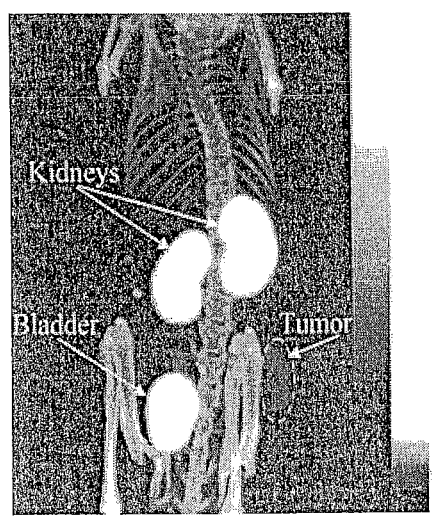
FIG. 6. Whole-body SPECT/CT image of $^{99m}$Tc-RGD-Lys-(Arg$^{11}$)CCMSH in a B16/F1 melanoma-bearing C57 mouse at 2 h post-injection.
Figure 7:
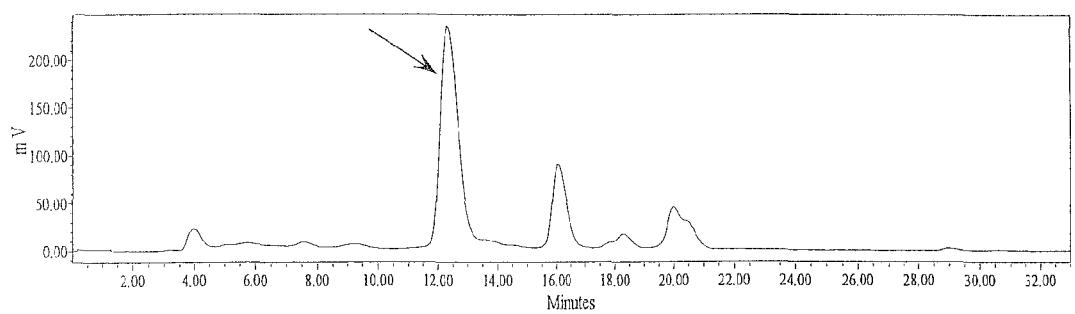
FIG. 7. HPLC profile of radioactive urine sample of a B16/F1 murine melanoma-bearing C57 mouse at 2 h post-injection of $^{99m}$Tc-RGD-Lys-(Arg$^{11}$)CCMSH. Arrow indicates the retention time of the original compound of $^{99m}$Tc-RGD-Lys-(Arg$^{11}$)CCMSH prior to the tail vein injection.

One B16/F1 melanoma-bearing C57 mouse was injected with $^{99m}$Tc-RGD-Lys-(Arg$^{11}$)CCMSH through the tail vein to visualize the tumors 2 h after dose administration. The whole-body SPECT/CT image is presented in FIG. 6. Flank melanoma tumors were visualized clearly by $^{99m}$Tc-RGD- Lys-(Arg$^{11}$)CCMSH 2 h post-injection. $^{99m}$Tc-RGD-Lys-(Arg$^{11}$)CCMSH exhibited high tumor to normal organ uptake ratios except for the kidney, which was coincident with the biodistribution results. In view of the substantial renal uptake values of $^{99m}$Tc-RGD-Lys-(Arg$^{11}$)CCMSH in the biodistribution results, the urinary metabolites of $^{99m}$Tc-ROD-Lys-(Arg$^{11}$)CCMSH were analyzed by RP-HPLC 2 h post-injection. The urinary HPLC profile of $^{99m}$Tc-ROD-Lys-(Arg$^{11}$)CCMSH is shown in FIG. 7. Approximately 68% of $^{99m}$Tc-RGD-Lys-(Arg$^{11}$)CCMSH remained intact, while 32% of $^{99m}$Tc-RGD-Lys-(Arg$^{11}$)CCMSH was transformed to two more lipophilic metabolites 2 h post-injection.

Discussion

Metastatic melanoma is very aggressive and is resistant to current available chemotherapy and immunotherapy. High mortality of malignant melanoma is associated with the occurrence of melanoma metastases. Hence, it is highly desirable to develop novel and effective therapeutic approaches to improve the therapeutic effectiveness of melanoma treatment. Peptide-targeted radionuclide therapy is a novel and effective treatment approach for melanoma. MC1 receptor-avid α-MSH peptides are employed as effective delivery vehicles to selectively and specifically target cytotoxic radiation generated from radionuclides to tumor cells, resulting in tumor cell death (28). In comparison with external beam radiation therapy and chemotherapy, peptide-targeted radionuclide therapy can specifically deliver the cytotoxic radiation to tumor cells, while sparing the normal tissues and organs. Unique metal-cyclized α-MSH peptides labeled with various therapeutic radionuclides (i.e. $^{177}$Lu, $^{188}$Re and $^{212}$Pb) exhibited very promising therapeutic effects in preclinical melanoma-bearing mouse models (15-17), demonstrating the potential of peptide-targeted radionuclide therapy for human melanoma treatment. The findings of that ROD-containing peptide could induce cell apoptosis through activating cytoplasmic procaspase-3 directly after the peptide entering the cells (22) opened the avenue of using the RGD motif as an intracellular apoptosis inducer for cancer therapy. ROD-Lys($^{111}$In-DTPA)-Tyr$^3$-Octreotate exhibited enhanced tumoricidal effects than $^{111}$In-DTPA-Tyr$^3$-octreotate due to elevated tumor cell apoptosis (23), demonstrating the feasibility of coupling the RGD motif to the receptor-targeting peptides to enhance the synergistic therapeutic effectiveness of the radiolabeled hybrid peptides. In this study, we designed and synthesized novel RGD-Lys-(Arg$^{11}$)CCMSH hybrid peptide to examine whether the unique metal-cyclized α-MSH peptide {$^{99m}$Tc-(Arg$^{11}$)CCMSH} could be used as an effective delivery vehicle to specifically transport the RGD motif into melanoma cells.

Synthetic hybrid RGD-Lys-(Arg$^{11}$)CCMSH exhibited 2.1 nM MC1 receptor binding affinity in B16/F1 cells (FIG. 2), whereas (Arg$^{11}$)CCMSH displayed 1.7 nM MC1 receptor binding affinity (8), demonstrating that the coupling of the RGD motif did maintain the nanomolar MC1 receptor binding affinity of the hybrid peptide. $^{99m}$Tc-RGD-Lys-(Arg$^{11}$)CCMSH was easily prepared using a glucoheptonate transchelation reaction and stable in mouse serum for 24 h. The coordination of $^{99m}$Tc with three cysteines presented in the RGD-Lys-(Arg$^{11}$)CCMSH simultaneously cyclized the hybrid peptide, making $^{99m}$Tc-RGD-Lys-(Arg$^{11}$)CCMSH stable against proteolytic degradation in vivo (29). As we anticipated, $^{99m}$Tc-RGD-Lys-(Arg$^{11}$)CCMSH exhibited rapid internalization and extended efflux in B16/F1 cells (FIG. 3), with approximately 76% of the $^{99m}$Tc-RGD-Lys-(Arg$^{11}$)CCMSH activity internalized 40 min post incubation and 69% of the internalized activity remained in the cells after 2 h incubation in culture medium. Efficient cellular internalization and extended retention of $^{99m}$Tc-RGD-Lys-(Arg$^{11}$)CCMSH warrant effective transportation of the RGD motif into the melanoma cells, as well as subsequent long-lasting apoptotic effect generated from the RGD motif after entering the melanoma cells. Approximately 90% of the cellular uptake of $^{991}$Tc-RGD-Lys-(Arg$^{11}$)CCMSH was blocked by RGD-Lys-(Arg$^{11}$)CCMSH, (Arg$^{11}$)CCMSH or NDP-MSH (rather than RGD), demonstrating that the cellular uptake of $^{99m}$Tc-RGD-Lys-(Arg$^{11}$)CCMSH was MC1 receptor-mediated rather than $\alpha_v\beta_3$ integrin-mediated. The MC1 receptor-mediated cellular uptake of $^{99m}$Tc-RGD-Lys-(Arg$^{11}$)CCMSH was consistent with the reported immunohistochemical results that RGD-HuMab only localized at the endothelium of B16/F10 melanoma tumor rather than B16/F10 melanoma cells (30). Nanomolar MC1 receptor binding affinity, rapid internalization and extended retention of the hybrid RGD-Lys-(Arg$^{11}$)CCMSH in melanoma cells warranted further evaluation on melanoma targeting and pharmacokinetic properties of $^{991}$Tc-RGD-Lys-(Arg$^{11}$)CCMSH in melanoma-bearing mice.

$^{99m}$Tc-RGD-Lys-(Arg$^{11}$)CCMSH exhibited rapid high B16/F1 melanoma uptake value of 11.06±1.41% ID/g 0.5 h post-injection and reached its peak tumor uptake value of 14.83±2.94% ID/g 2 h post-injection (Table 1). Meanwhile, $^{99m}$Tc-RGD-Lys-(Arg$^{11}$)CCMSH displayed prolonged retention in melanoma tumors. The tumor uptake value was 12.57±2.53% ID/g 4 h post-injection, which was 85% of the tumor uptake value 2 h post-injection. Even 24 h post-injection, the tumor uptake value was 7.59±2.04% ID/g, which was 51% of the tumor uptake value 2 h post-injection. Tumor uptake blocking studies with NDP-MSH or RGD in B16/F1 melanoma-bearing mice (Table 1) showed that 87.8% of the tumor uptake of $^{99m}$Tc-RGD-Lys-(Arg$^{11}$)CCMSH was blocked by 6.1 nmol of NDP-MSH, whereas 29.2% of the tumor uptake of $^{99m}$Tc-RGD-Lys-(Arg$^{11}$)CCMSH was blocked by 6.1 nmol of RGD, indicating that the majority of melanoma uptake of $^{99m}$Tc-RGD-Lys-(Arg$^{11}$)CCMSH was MC1 receptor-mediated. It was reported that $\alpha_v\beta_3$ integrin receptors were overexpressed in B16/F10 tumor vasculature (30). The B16/F1 melanoma tumors consist of highly vascularized dense gelatinous masses. The $\alpha_v\beta_3$ integrin-mediated tumor uptake was likely due to the presence of $\alpha_v\beta_3$ integrin receptors in the B16/F1 tumor vasculature. Interestingly, $^{99m}$Tc-RGD-Lys-(Arg$^{11}$)CCMSH showed comparable tumor uptake value as $^{99m}$Tc-(Arg$^{11}$)CCMSH 4 h post-injection and longer tumor retention than $^{99m}$Tc-(Arg$^{11}$)CCMSH 24 h post-injection in the same B16/F1 melanoma-bearing mouse model (13). The tumor uptake values of $^{99m}$Tc-RGD-Lys-(Arg$^{11}$)CCMSH were 1.1 and 2.3 times the tumor uptake values of $^{99m}$Tc-(Arg$^{11}$)CCMSH 4 and 24 h post-injection, respectively. The improved melanoma retention of $^{99m}$Tc-RGD-Lys-(Arg$^{11}$)CCMSH attributed to the introduction of the RGD motif in $^{99m}$Tc-RGD-Lys-(Arg$^{11}$)CCMSH. It was likely that the RGD motif in hybrid $^{99m}$Tc-RGD-Lys-(Arg$^{11}$)CCMSH bound to the $\alpha_v\beta_3$ integrin receptors presented on blood vessels in B16/F1 tumors, contributing the prolonged tumor retention of $^{99m}$Tc-RGD-Lys-(Arg$^{11}$)CCMSH. From the therapeutic point of view, high melanoma uptake and prolonged retention of $^{99m}$Tc-RGD-Lys-(Arg$^{11}$)CCMSH warranted long-lasting synergistic therapeutic effects of apoptosis and targeted radiation from $^{188}$Re-labeled hybrid CCMSH peptide. Flank B16/F1 melanoma tumors were clearly visualized by SPECT/CT imaging using $^{99m}$Tc-RGD-Lys-(Arg$^{11}$)CCMSH as an imaging probe 2 h post injection (FIG. 6). The SPECT image of tumor accurately matched its anatomical information from CT image. $^{99m}$Tc-RGD-Lys-(Arg$^{11}$)CCMSH displayed high tumor to normal organ uptake ratios except for the kidneys, which was coincident with the biodistribution results (Table 1).

The RGD motif was attached to the somatostatin-2 receptor-targeting Tyr³-Octreotate via Lys to yield hybrid RGD-Lys($^{111}$In-DTPA)-Tyr³-Octreotate. DTPA was attached to the amino group on the side chain of Lys for $^{111}$In labeling (24). In this study, The RGD motif was conjugated to (Arg$^{11}$)CCMSH via Lys to generate RGD-Lys-(Arg$^{11}$)CCMSH. The advantage of using Lys as a linker to connect the RGD motif with the (Arg$^{11}$)CCMSH moiety was that the amino group on the side chain of Lys could be used to attach DOTA for coordination with a variety of therapeutic radionuclides (i.e. $^{177}$Lu, $^{90}$Y and $^{212}$Pb) to generate synergistic therapeutic effects of targeted radiation from the therapeutic radionuclides and apoptosis from the RGD motif. The coupling of the RGD motif to the Tyr³-Octreotate through Lys increased the renal uptake value of RGD-Lys($^{111}$In-DTPA)-Tyr³-Octreotate compared to $^{111}$In-DOTA-Tyr³-Octreotate (24). The renal uptake value of RGD-Lys($^{111}$In-DTPA)-Tyr³-Octreotate was 3.3 times the renal uptake value of $^{111}$In-DOTA-Tyr³-Octreotate in CA20948 and AR42J tumor-bearing Lewis rats 24 h post-injection (24). Surprisingly, the renal uptake value of $^{99m}$Tc-RGD-Lys-(Arg$^{11}$)CCMSH was 12.5 times the renal uptake value of $^{99m}$Tc-(Arg$^{11}$)CCMSH in B16/F1 melanoma-bearing mice 4 h post-injection. Considering the structural difference between the $^{99m}$Tc-RGD-Lys-(Arg$^{11}$)CCMSH and $^{9m}$Tc-(Arg$^{11}$)CCMSH, the substantial increased renal uptake of $^{99m}$Tc-RGD-Lys-(Arg$^{11}$)CCMSH was due to the introduction of the RGD-Lys moiety. Further biodistribution comparison revealed that the renal uptake value of $^{99m}$Tc-RGD-Lys-(Arg$^{11}$)CCMSH was only 1.2 times the renal uptake value of $^{188}$Re-dLys-(Arg$^{11}$)CCMSH (31), indicating that the Lys between the RGD motif and the (Arg$^{11}$)CCMSH moiety played an important role in high renal uptake value of $^{99m}$Tc-RGD-Lys-(Arg$^{11}$)CCMSH. It is necessary to note that the amino group on the side chain of the Lys was available in $^{99m}$Tc-RGD-Lys-(Arg$^{11}$)CCMSH and added a positive charge to the overall charge of $^{99m}$Tc-RGD-Lys-(Arg$^{11}$)CCMSH, that might contribute to the high renal uptake value of $^{99m}$Tc-RGD-Lys-(Arg$^{11}$)CCMSH due to the electrostatic interaction between positively-charged peptide molecules and negatively-charged tubule cells. A direct way to shield the effect of positively-charged amino group on the side chain of the Lys is to conjugate DOTA to RGD-Lys-(Arg$^{11}$)CCMSH through the amino group on the side chain of the Lys. Conjugation of DOTA to the amino group on the side chain of the Lys in RGD-Lys-(Arg$^{11}$)CCMSH can reduce the overall positive charge of radiolabeled hybrid CCMSH peptide, as well as provide an excellent metal chelator for the coordination of therapeutic radionuclides such as $^{177}$Lu, $^{90}$Y and $^{212}$Pb. Furthermore, strategies of co-injection of positively-charged amino acid and structurally introduction of negatively-charged amino acid into peptide sequence will also be options to employ to decrease the renal uptakes of the radiolabeled hybrid CCMSH peptides. Co-injection of lysine or arginine has effectively reduced the renal uptakes of $^{188}$Re-labeled metal-cyclized CCMSH by 50% (8). Introduction of a negatively-charged Glu at $2^{nd}$ position of metal-cyclized CCMSH peptide decreased 72% of the renal uptake values of $^{177}$Lu- and $^{90}$Y-DOTA-Re(Arg$^{11}$)CCMSH 4 h post-injection (32, 33).

It will be attractive to determine the synergistic therapeutic effects of apoptosis and targeted radiation of $^{188}$Re-labeled α-MSH hybrid peptides for melanoma once the strategies of amino acid co-injection or structural modification of peptide sequence substantially reduce the renal uptake. Targeted radionuclide therapy with $^{188}$Re-(Arg$^{11}$)CCMSH exhibited therapeutic effects in both human and murine melanoma-bearing mice (15). Non-radioactive hybrid RGD-Lys-(Arg$^{11}$)CCMSH showed very promising cytotoxic effect in B16/F1 cells in our unpublished preliminary studies. Single treatment (3 h incubation) with 93 μmol of RGD-Lys-(Arg$^{11}$)CCMSH decreased 65% of clonogenic survival of B16/F1 cells compared to untreated control (cell culture medium) and (Arg$^{11}$)CCMSH (93 μmol) treated group 6 days post the treatment (data not shown). Combination therapy of $α_vβ_3$ integrin receptor antagonist and $^{90}$Y-DOTA-peptide ChL6 exhibited increased synergistic (apoptosis and targeted radiation) therapeutic effects in breast cancer xenografts without increased toxicity (34). RGD-Lys($^{111}$In-DTPA)-Tyr³-Octreotate displayed more profound tumoricidal effects than $^{111}$In-DTPA-Tyr³-octreotate and $^{111}$In-DTPA-RGD due to elevated tumor cell apoptosis (23), highlighting the potential enhanced synergistic therapeutic effectiveness of $^{188}$Re-labeled α-MSH hybrid peptides for melanoma in future studies.

Conclusions

Novel RGD-Lys-(Arg$^{11}$)CCMSH showed 2.1 nM MC1 receptor binding affinity. $^{99m}$Tc-RGD-Lys-(Arg$^{11}$)CCMSH exhibited MC1 receptor mediated rapid cellular internalization and extended retention. Furthermore, $^{99m}$Tc-RGD-Lys-(Arg$^{11}$)CCMSH displayed rapid high melanoma uptake and prolonged tumor retention in B16/F1 melanoma bearing mice. Favorable melanoma targeting property of $^{99m}$Tc-RGD-Lys-(Arg$^{11}$)CCMSH warranted the further evaluation of $^{188}$Re-labeled α-MSH hybrid peptides as novel MC1 receptor-targeting therapeutic peptides for melanoma treatment once the strategies of amino acid co-injection or structural modification of peptide sequence substantially reduce the renal uptake.

TABLE 1

Biodistribution of $^{99m}$Tc-RGD-Lys-(Arg$^{11}$)CCMSH in B16/F1 murine melanoma-bearing C57 mice.

| Tissue | 0.5 h | 2 h | 2 h NDP blockade | 2 h RGD blockade | 4 h | 24 h |
|---|---|---|---|---|---|---|
| | | | Percentage Injected Dose/gram (% ID/g) | | | |
| Tumor | 11.06 ± 1.41 | 14.83 ± 2.94 | 1.81 ± 0.64* | 10.50 ± 1.18* | 12.57 ± 2.53 | 7.59 ± 2.04 |
| Brain | 0.13 ± 0.03 | 0.12 ± 0.03 | 0.06 ± 0.02* | 0.03 ± 0.01* | 0.07 ± 0.04 | 0.06 ± 0.01 |
| Blood | 3.18 ± 0.51 | 0.96 ± 0.87 | 0.32 ± 0.34 | 0.53 ± 0.17 | 0.50 ± 0.27 | 0.11 ± 0.07 |
| Heart | 2.10 ± 0.41 | 0.85 ± 0.16 | 0.47 ± 0.18* | 0.37 ± 0.23* | 0.62 ± 0.31 | 0.39 ± 0.14 |
| Lung | 5.31 ± 0.53 | 1.26 ± 0.32 | 1.31 ± 0.47 | 1.12 ± 0.10 | 1.07 ± 0.42 | 0.94 ± 0.45 |
| Liver | 4.02 ± 0.42 | 3.17 ± 1.43 | 2.89 ± 0.25 | 2.27 ± 0.23 | 2.91 ± 0.80 | 1.73 ± 0.33 |
| Skin | 4.53 ± 0.88 | 1.52 ± 0.66 | 1.14 ± 0.38 | 0.81 ± 0.13 | 1.17 ± 0.61 | 0.78 ± 0.19 |
| Spleen | 2.18 ± 0.88 | 1.23 ± 0.62 | 0.75 ± 0.37 | 0.94 ± 0.30 | 1.14 ± 0.16 | 0.88 ± 0.30 |
| Stomach | 7.61 ± 1.98 | 2.57 ± 0.38 | 2.43 ± 0.80 | 2.64 ± 0.10 | 2.46 ± 1.39 | 0.91 ± 0.67 |
| Kidneys | 69.37 ± 5.37 | 67.12 ± 8.79 | 59.53 ± 9.98 | 54.24 ± 15.11 | 69.29 ± 14.34 | 40.26 ± 10.83 |

TABLE 1-continued

Biodistribution of $^{99m}$Tc-RGD-Lys-(Arg$^{11}$)CCMSH in B16/F1 murine melanoma-bearing C57 mice.

| Tissue | 0.5 h | 2 h | 2 h NDP blockade | 2 h RGD blockade | 4 h | 24 h |
|---|---|---|---|---|---|---|
| Muscle | 0.38 ± 0.17 | 0.34 ± 0.29 | 0.21 ± 0.12 | 0.15 ± 0.06 | 0.13 ± 0.07 | 0.23 ± 0.19 |
| Pancreas | 1.48 ± 1.24 | 0.72 ± 0.53 | 0.44 ± 0.37 | 0.35 ± 0.19 | 0.52 ± 0.41 | 0.25 ± 0.06 |
| Bone | 1.53 ± 0.75 | 1.05 ± 0.31 | 0.78 ± 0.65 | 0.37 ± 0.42* | 0.98 ± 0.67 | 0.71 ± 0.39 |
| Percentage Injected Dose (% ID) | | | | | | |
| Intestines | 3.27 ± 0.13 | 3.14 ± 1.20 | 1.97 ± 0.17 | 1.88 ± 0.16 | 2.95 ± 0.62 | 1.13 ± 0.18 |
| Bladder | 46.92 ± 2.54 | 62.26 ± 8.16 | 75.86 ± 1.75 | 75.09 ± 3.69 | 68.69 ± 2.06 | 78.25 ± 5.29 |
| Uptake Ratio of Tumor/Normal Tissue | | | | | | |
| Tumor/Blood | 3.48 | 15.45 | 5.66 | 19.81 | 25.14 | 69.00 |
| Tumor/Kidneys | 0.16 | 0.22 | 0.03 | 0.19 | 0.18 | 0.19 |
| Tumor/Lung | 2.08 | 11.77 | 1.38 | 9.38 | 11.75 | 8.07 |
| Tumor/Liver | 2.75 | 4.68 | 0.63 | 4.63 | 4.32 | 4.39 |
| Tumor/Muscle | 29.11 | 43.62 | 8.62 | 70.00 | 96.69 | 33.00 |

The data was presented as percent injected dose/gram or as percent injected dose (mean ± SD, n = 5)
*P < 0.05, significance comparison between $^{99m}$Tc-RGD-Lys-(Arg$^{11}$)CCMSH with or without blockade peptide.

$^{99m}$Tc-RGD-Arg-(Arg$^{11}$)CCMSH
Materials and Methods
Chemicals and Reagents Amino acid and resin were purchased from Advanced ChemTech Inc. (Louisville, Ky.) and Novabiochem (San Diego, Calif.). $^{99m}$TcO$_4^-$ was purchased from Cardinal Health (Albuquerque, N. Mex.). $^{125}$I-Tyr$^2$-[Nle$^4$, D-Phe$^7$]-α-MSH {$^{125}$I-(Tyr$^2$)-NDP MSH} was obtained from PerkinElmer, Inc. (Shelton, Conn.). Cyclo(Arg-Gly-Asp-DPhe-Val) {RGD} peptide was purchased from Enzo Life Sciences (Plymouth Meeting, Pa.) for peptide blocking studies. All other chemicals used in this study were purchased from Thermo Fischer Scientific (Waltham, Mass.) and used without further purification. B16/F1 murine melanoma cells were obtained from American Type Culture Collection (Manassas, Va.).

Example 1B

Peptide Synthesis

Intermediate scaffold of H$_2$N-Arg(Pbf)-Gly-Asp(OtBu)-DTyr(tBu)-Asp(O-2-phenylisopropyl)-Arg(Pbf)-Cys(Trt)-Cys(Trt)-Glu(OtBu)-His(Trt)-DPhe-Arg(Pbf)-Trp(Boc)-Cys(Trt)-Arg(Pbf)-Pro-Val was synthesized on Sieber amide resin using standard 9-fluorenylmethyloxycarbonyl (Fmoc) chemistry by an Advanced ChemTech multiple-peptide synthesizer (Louisville, Ky.). A small aliquot of the scaffold material was cleaved and characterized by liquid chromatography-mass spectroscopy (LC-MS). The protecting group of 2-phenylisopropyl was removed and the peptide was cleaved from the resin treating with a mixture of 2.5% of trifluoroacetic acid (TFA) and 5% of triisopropylsilane. After the precipitation with ice-cold ether and characterization by LC-MS, the protected peptide was dissolved in H$_2$O/CH$_3$CN (50:50) and lyophilized to remove the reagents such as TFA and triisopropylsilane. The protected peptide was further cyclized by coupling the carboxylic group from the Asp with the alpha amino group from the Arg at the N-terminus. The cyclization reaction was achieved by overnight reaction in DMF using benzotriazole-1-yl-oxy-tris-pyrrolidino-phosphonium-hexafluorophosphate (PyBOP) as a coupling agent in the presence of N,N-diisopropylethylamine (DIEA). After characterization by LC-MS, the protected cyclized peptide was dissolved in H$_2$O/CH$_3$CN (50:50) and lyophilized to remove the reagents such as PyBOP and DIEA. The protecting groups were totally removed by treating with a mixture of trifluoroacetic acid (TFA), thioanisole, phenol, water, ethanedithiol and triisopropylsilane (87.5:2.5:2.5:2.5:2.5:2.5) for 2 h at room temperature (25° C.). The peptide was precipitated and washed with ice-cold ether four times, purified by reverse phase-high performance liquid chromatography (RP-HPLC) and characterized by LC-MS.

Example 2B

In Vitro Competitive Binding Assay

The IC$_{50}$ value of RGD-Arg-(Arg$^{11}$)CCMSH was determined according to our previously published procedure (17). B16/F1 cells were harvested and seeded into a 24-well cell culture plate (5×10$^5$/well) and incubated at 37° C. overnight. After being washed with binding medium {Modified Eagle's medium with 25 mM N-(2-hydroxyethyl)-piperazine-N'-(2-ethanesulfonic acid), pH 7.4, 0.2% bovine serum albumin (BSA), 0.3 mM 1,10-phenathroline}, the cells were incubated at room temperature (25° C.) for 2 h with approximately 40,000 counts per minute (cpm) of $^{125}$I-(Tyr$^2$)-NDP-MSH in the presence of increasing concentrations (10$^{-12}$ to 10$^{-5}$ M) of RGD-Arg-(Arg$^{11}$)CCMSH in 0.3 mL of binding medium. The reaction medium was aspirated after the incubation. The cells were rinsed twice with 0.5 mL of ice-cold pH 7.4, 0.2% BSA/0.01 M phosphate buffered saline (PBS) and lysed in 0.5 mL of 1 N NaOH for 5 minutes. The activities associated with cells were measured in a Wallac 1480 automated gamma counter (PerkinElmer, NJ). The IC$_{50}$ value for the peptide was calculated using Prism software (GraphPad Software, La Jolla, Calif.).

Example 3B

Peptide Radiolabelling

RGD-Arg-(Arg$^{11}$)CCMSH was radiolabeled with $^{99m}$Tc via a glucoheptonate transchelation reaction using methods described previously (17). Briefly, 100 μL of 2 mg/mL SnCl$_2$ in 0.2 M glucoheptonate aqueous solution and 200 μL of fresh $^{99m}$TcO$_4^-$ solution (37-148 MBq) were added into a reaction vial and incubated at room temperature (25° C.) for 20 mM to form $^{99m}$Tc-glucoheptonate. Then, 10 μL of 1 mg/mL RGD-Arg-(Arg$^{11}$)CCMSH aqueous solution was added into the reaction vial and the pH of the reaction mixture was adjusted to 8.5 with 0.1 M NaOH. The reaction mixture was incubated at 75° C. for 40 min. The radiolabeled peptide was purified to single species by Waters RP-HPLC (Milford, Mass.) on a Grace Vydac C-18 reverse phase analytic column (Deerfield, Ill.) using a 20 min gradient of 16-26% acetonitrile in 20 mM HCl aqueous solution at a flow rate of 1 mL/min. The purified peptide sample was purged with $N_2$ gas for 20 min to remove the acetonitrile. The pH of the final solution was adjusted to 5 with 0.1 N NaOH and normal saline for animal studies. The stability of $^{99m}$Tc-RGD-Arg-(Arg$^{11}$)CCMSH was determined by incubation in mouse serum at 37° C. according to the published procedure (17) for various time periods, and monitored for degradation by RP-HPLC.

Example 4B

Cellular Internalization and Efflux of $^{99m}$Tc-RGD-Arg-(Arg$^{11}$)CCMSH

Cellular internalization and efflux of $^{99m}$Tc-RGD-Arg-(Arg$^{11}$)CCMSH was evaluated in B16/F1 cells as previously described by Yang et al (17). After being washed once with binding medium, B16/F1 cells in 24-well cell culture plates were incubated at 25° C. for 20, 40, 60, 90 and 120 min (n=3) in the presence of approximately 200,000 cpm of HPLC purified 99"Tc-RGD-Arg-(Arg$^{11}$)CCMSH. After incubation, the reaction medium was aspirated and the cells were rinsed twice with 0.5 mL of ice-cold pH 7.4, 0.2% BSA/0.01 M PBS. Cellular internalization of $^{99m}$Tc-RGD-Arg-(Arg$^{11}$)CCMSH was assessed by washing the cells with acidic buffer [40 mM sodium acetate (pH 4.5) containing 0.9% NaCl and 0.2% BSA] to remove the membrane-bound radioactivity. The remaining internalized radioactivity was obtained by lysing the cells with 0.5 mL of 1 N NaOH for 5 min. Membrane-bound and internalized $^{99m}$Tc activities were counted in a gamma counter. Cellular efflux of $^{99m}$Tc-RGD-Arg-(Arg$^{11}$)CCMSH was determined by incubating B16/F1 cells with $^{99m}$Tc-RGD-Arg-(Arg$^{11}$)CCMSH for 2 h at 25° C., removing non-specific-bound radioactivity with 2×0.5 mL of ice-cold pH 7.4, 0.2% BSA/0.01 M PBS rinse, and monitoring radioactivity released into cell culture medium. At time points of 20, 40, 60, 90 and 120 min, the radioactivities on cell surface and in cells were separately collected and counted in a gamma counter.

Example 5B

Specificity of Cellular Uptake of $^{99m}$Tc-RGD-Arg-(Arg$^{11}$)CCMSH

The specificity of cellular uptake was determined by incubating $^{99m}$Tc-RGD-Arg-(Arg$^{11}$)CCMSH with or without non-radioactive peptides. After being washed once with binding medium, B16/F1 cells in 24-well cell culture plates were incubated with approximately 200,000 cpm of HPLC purified $^{99m}$Tc-RGD-Arg-(Arg$^{11}$)CCMSH at 25° C. for 120 min (n=3) in the presence of 0.1 µM of RGD-Arg-(Arg$^{11}$)CCMSH, (Arg$^{11}$)CCMSH, RGD or no peptide blockade in 0.5 mL of binding medium, respectively. The reaction medium was aspirated after the incubation. The cells were rinsed twice with 0.5 mL of ice-cold pH 7.4, 0.2% BSA/0.01 M PBS and lysed in 0.5 mL of 1 N NaOH for 5 min. The activities associated with cells were measured in a gamma counter.

Example 6B

Biodistribution Studies

All the animal studies were conducted in compliance with Institutional Animal Care and Use Committee approval. The pharmacokinetics of $^{99m}$Tc-RGD-Arg-(Arg$^{11}$)CCMSH was determined in B16/F1 melanoma-bearing C57 female mice (Harlan, Indianapolis, Ind.). C57 mice were subcutaneously inoculated on the right flank with 1×10$^6$ B16/F1 cells. The weight of tumors reached approximately 0.2 g 10 days post cell inoculation. Each melanoma-bearing mouse was injected with 0.037 MBq of $^{99m}$Tc-RGD-Arg-(Arg$^{11}$)CCMSH via the tail vein. Groups of 5 mice were sacrificed at 0.5, 2, 4 and 24 h post-injection, and tumors and organs of interest were harvested, weighed and counted. Blood values were taken as 6.5% of the whole-body weight. The MC1 receptor specificity of the tumor uptake was determined at 2 h post-injection by co-injecting $^{99m}$Tc-RGD-Arg-(Arg$^{11}$)CCMSH with 10 µg (6.1 nmol) of unlabeled NDP-MSH. The co-injection of 3.5 µg (6.1 nmol) of RGD peptide was performed to determine the $\alpha_v\beta_3$ integrin specificity of the tumor uptake at 2 h post-injection.

The effects of L-lysine co-injection on the renal uptakes of $^{99m}$Tc-RGD-Arg-(Arg$^{11}$)CCMSH and $^{99m}$Tc-RGD-Lys-(Arg$^{11}$)CCMSH was examined in B16/F1 melanoma-bearing C57 as well. Two groups of 5 mice were injected with an aqueous mixture of 0.037 MBq of $^{99m}$Tc-RGD-Arg-(Arg$^{11}$) CCMSH and 15 mg of L-lysine or an aqueous mixture of 0.037 MBq of $^{99m}$Tc-RGD-Lys-(Arg$^{11}$)CCMSH and 15 mg of L-lysine, respectively. The mice were sacrificed at 2 h post-injection, and tumors and kidneys were harvested, weighed and counted.

Example 7B

Imaging Melanoma with $^{99m}$Tc-RGD-Arg-(Arg$^{11}$)CCMSH

A B16/F1 melanoma-bearing C57 mouse was injected with 6.1 MBq of $^{99m}$Tc-RGD-Arg-(Arg$^{11}$)CCMSH via the tail vein. The mouse was anesthetized with 1.5% isoflurane for small animal SPECT/CT (Nano-SPECT/CT®, Bioscan) imaging 2 h post-injection. The 9-min. CT imaging was immediately followed by the SPECT imaging of whole-body. The SPECT scans of 24 projections were acquired and total acquisition time was approximately 45 min. After the SPECT imaging, the mouse was euthanized with $CO_2$ inhalation. Reconstructed data from SPECT and CT were visualized and co-registered using InVivoScope (Bioscan, Washington D.C.).

Example 9B

Urinary Metabolites of $^{99m}$Tc-RGD-Arg-(Arg$^{11}$)CCMSH

Urinary metabolites of $^{99m}$Tc-RGD-Arg-(Arg$^{11}$)CCMSH were determined by injecting 3.7 MBq of $^{99m}$Tc-RGD-Arg-(Arg$^{11}$)CCMSH into a B16/F1 melanoma-bearing C57 mouse through the tail vein. At 2 h after dose administration, the mouse was euthanized and the urine was collected. The radioactive metabolites in the urine were analyzed by injecting aliquots of urine into HPLC. A 20-minute gradient of 16-26% acetonitrile/20 mM HCl was used for the urine analysis.

Example 10B

Clonogenic Cytotoxicity of RGD-Arg-(Arg)CCMSH

To determine whether the replacement of the Lys linker with Arg linker affected the clonogenic cytotoxicity of the hybrid peptide, we examined the clonogenic cytotoxic effect of RGD-Arg-(Arg$^{11}$)CCMSH in B16/F1 melanoma cells according to our published procedure (17). The B16/F1 cells were seeded in a 6-well plate (200 cells/well) and incubated at 37° C. overnight. After been washed once with culture medium (RPMI 1640 medium), the cells were incubated in the culture medium at 37° C. for 3 h in the presence of 0.1 µM of RGD-Arg-(Arg$^{11}$)CCMSH, (Arg$^{11}$)CCMSH or RGD, respectively. Control cells were only incubated in the culture medium. After the incubation, the cells were washed with PBS twice and allowed to form colonies over 6 days in the culture medium. The medium was changed every other day. After 6 days, the cells were fixed with methanol:glacial acetic acid (3:1), stained with hematoxylin and visually examined under microscope for survival. Colonies contained more than 50 cells were scored as survivors.

Statistical Methods

Statistical analysis was performed using the Student's t-test for unpaired data to determine the significant differences between the groups in the studies of specificity of cellular uptake, biodistribution and clonogenic cytotoxicity described above. Differences at the 95% confidence level (p 0.05) were considered significant.

Results

Figure 11:
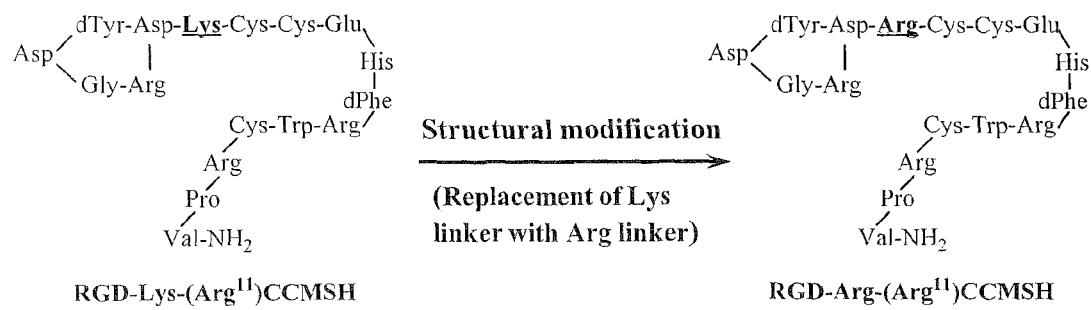
FIG. 11. Shows the schematic structures of RGD-Arg-(Arg11)CCMSH and RGD-Lys-(Arg11)CCMSH.
Figure 12:
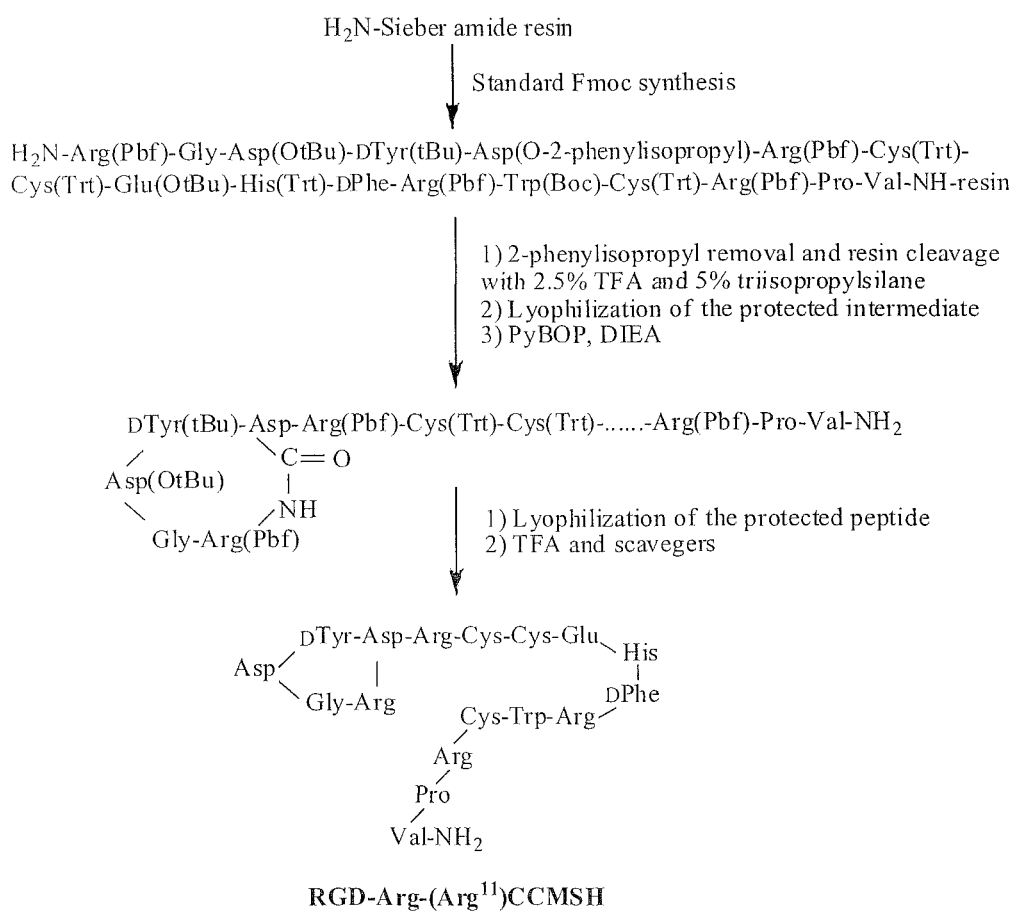
FIG. 12. Shows the synthetic scheme of RGD-Arg-(Arg11) CCMSH.
Figure 13:
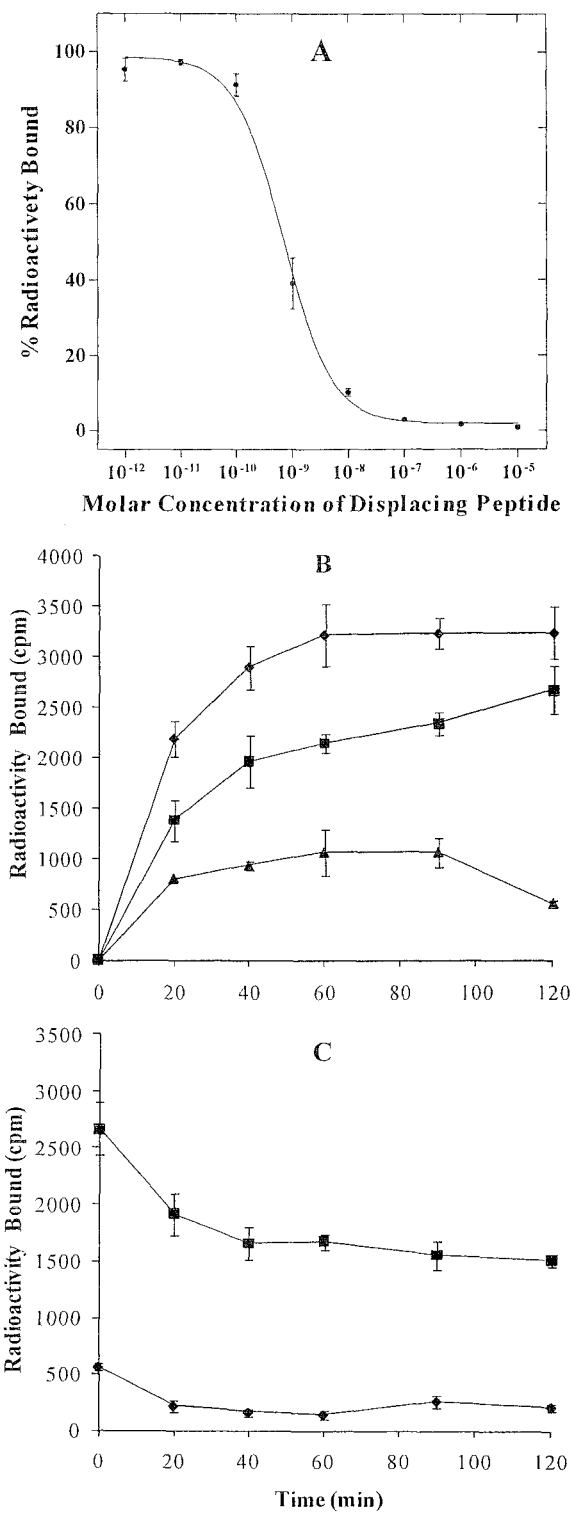
FIG. 13. Shows the competitive binding curve (A) of RGD-Arg-(Arg11)CCMSH in B16/F1 melanoma cells. The IC50 value of RGD-Arg-(Arg11) CCMSH was 0.7 nM; Cellular internalization (B) and efflux (C) of 99mTc-RGD-Arg-(Arg11)CCMSH in B16/F1 melanoma cells.Total bound radioactivity (♦), internalized activity (■) and cell membrane activity (▲) were presented as counts per minute (cpm).
Figure 14:
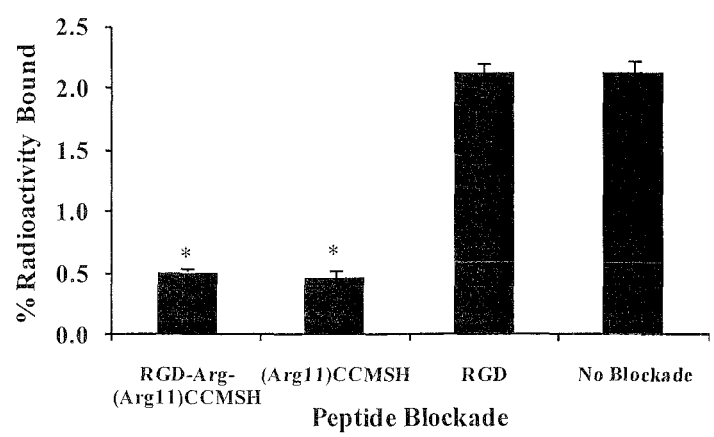
FIG. 14. Shows the blocking studies of cellular uptake of 99mTc-RGD-Arg-(Arg11)CCMSH in B16/F1 melanoma cells. The cells were incubated with 99mTc-RGD-Arg-(Arg11)CCMSH in the presence of 0.1 μM of RGD-Arg-(Arg11)-CCMSH, (Arg11)CCMSH, RGD or no peptide blockade. *p<0.05, significance comparison between the cellular uptakes of 99m Tc-RGD-Arg-(Arg11)CCMSH with or without peptide blockade.
Figure 15:
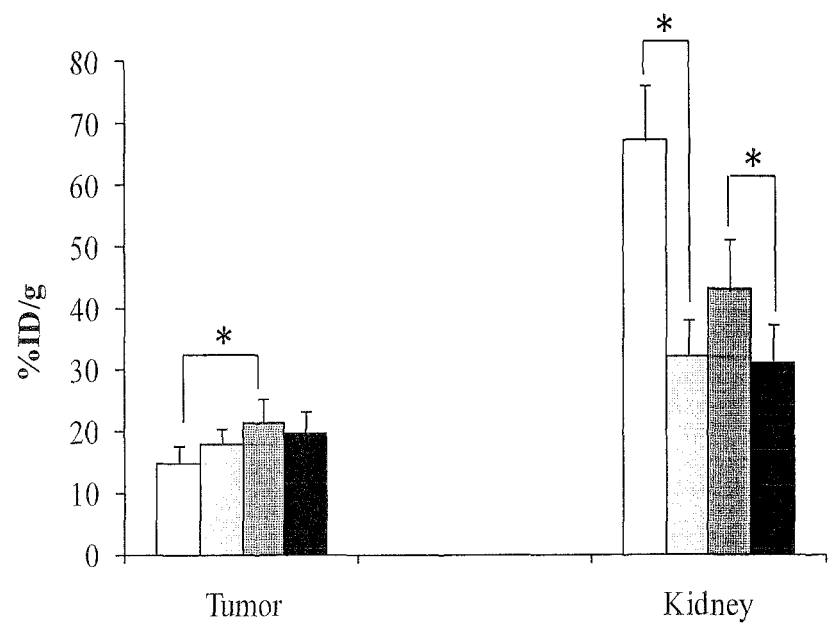
FIG. 15. Shows the Effect of L-lysine co-injection on the tumor and kidney uptakes of 99m Tc-RGD-Lys-(Arg11)CCMSH and 99m Tc-RGD-Arg-(Arg11)CCMSH at 2 h post-injection. The white ( ) and light grey ( ) columns represented the tumor and renal uptakes of 99m Tc-RGD-Lys-(Arg11) CCMSH with or without L-lysine co-injection. The heavy grey ( )and black ( ) columns represented the tumor and renal uptakes of 99m Tc-RGD-Arg-(Arg11)CCMSH with or without L-lysine co-injection. L-lysine co-injection significantly (*p<0.05) reduced the renal uptakes of 99m Tc-RGD-Arg-(Arg11)CCMSH by 27.7% and 99m Tc-RGD-Lys-(Arg11) CCMSH by 52.1% at 2 h post-injection without affecting the tumor uptakes. Meanwhile, the tumor uptake value of 99m Tc-RGD-Arg-(Arg11)CCMSH was 1.44 times (*p<0.05) the tumor uptake value of 99m Tc-RGD-Lys-(Arg11)CCMSH at 2 h post-injection.

RGD-Arg-(Arg$^{11}$)CCMSH was synthesized, purified by RP-HPLC and the identity of peptide was confirmed by electrospray ionization mass spectrometry. RGD-Arg-(Arg$^{11}$) CCMSH displayed greater than 95% purity with 30% overall synthetic yield. FIG. 11 illustrated the schematic structure of RGD-Arg-(Arg$^{11}$)CCMSH, as well as the schematic structure of RGD-Lys-(Arg$^{11}$)CCMSH for comparison. The synthetic scheme of RGD-Arg-(Arg$^{11}$)CCMSH is presented in FIG. 12. The competitive binding curve of RGD-Arg-(Arg$^{11}$) CCMSH is shown in FIG. 13. The IC$_{50}$ value of RGD-Arg-(Arg$^{11}$)CCMSH was 0.7 nM in B16/F1 cells. The peptide was readily labeled with $^{99m}$Tc using a glucoheptonate transchelation reaction with greater than 95% radiolabeling yield. $^{99m}$Tc-RGD-Arg-(Arg$^{11}$)CCMSH was completely separated from its excess non-labeled peptide by RP-HPLC. The retention times of $^{99m}$Tc-RGD-Arg-(Arg$^{11}$)CCMSH and its non-labeled RGD-Arg-(Arg$^{11}$)CCMSH were 13.2 and 12.4 min, respectively. $^{99m}$Tc-RGD-Arg-(Arg$^{11}$)CCMSH was stable in mouse serum at 37° C. for 24 h.

Cellular internalization and efflux of $^{99m}$Tc-RGD-Arg-(Arg$^{11}$)CCMSH was evaluated in B16/F1 cells. FIG. 13 illustrates cellular internalization and efflux of $^{99m}$Tc-RGD-Arg-(Arg$^{11}$)CCMSH. $^{99m}$Tc-RGD-Arg-(Arg$^{11}$)CCMSH exhibited rapid cellular internalization and extended cellular retention. There was 62.35±4.08% of the cellular uptake of $^{99m}$Tc-RGD-Arg-(Arg$^{11}$)CCMSH activity internalized in the B16/F1 cells 20 min post incubation. There was 81.36±0.96% of the cellular uptake of $^{99m}$Tc-RGD-Arg-(Arg$^{11}$)CCMSH activity internalized in the cells after 2 h incubation. Cellular efflux results demonstrated that 58.99±2.03% of the internalized $^{99m}$Tc-RGD-Arg-(Arg$^{11}$)CCMSH activity remained inside the cells 2 h after incubating the cells in culture medium.

Specificity of cellular uptake of $^{99m}$Tc-RGD-Arg-(Arg$^{11}$) CCMSH was examined in B16/F1 cells. The results are presented in FIG. 4. The cellular uptake of $^{99m}$Tc-RGD-Arg-(Arg$^{11}$)CCMSH was MC1 receptor-mediated rather than $\alpha_v\beta_3$ integrin-mediated. Compared to the cellular uptake of $^{99m}$Tc-RGD-Arg-(Arg$^{11}$)CCMSH without peptide blockade, the cellular uptakes of $^{99m}$Tc-RGD-Arg-(Arg$^{11}$)CCMSH decreased 76 and 78% with 0.1 μM of RGD-Arg-(Arg$^{11}$) CCMSH and (Arg$^{11}$)CCMSH as blockades, respectively. Incubation of $^{99m}$Tc-RGD-Arg-(Arg$^{11}$)CCMSH with 0.1 μM of RGD didn't reduce the cellular uptake of $^{99m}$Tc-RGD-Arg-(Arg$^{11}$)CCMSH in B16/F1 cells.

The melanoma targeting and pharmacokinetic properties of $^{99m}$Tc-RGD-Arg-(Arg$^{11}$)CCMSH were determined in B16/F1 melanoma-bearing C57 mice. The biodistribution results of $^{99m}$Tc-RGD-Arg-(Arg$^{11}$)CCMSH are shown in Table 2. $^{99m}$Tc-RGD-Arg-(Arg$^{11}$)CCMSH exhibited rapid and high tumor uptake in melanoma-bearing mice. The tumor uptake value was 14.09±2.42% ID/g at 0.5 h post-injection. $^{99m}$Tc-RGD-Arg-(Arg$^{11}$)CCMSH reached its peak tumor uptake value of 21.41±3.74% ID/g at 2 h post-injection. There was 16.05±2.00% ID/g of the $^{99m}$Tc-RGD-Arg-(Arg$^{11}$)CCMSH activity remained in the tumors at 4 h post-injection. The tumor uptake value of $^{99m}$Tc-RGD-Arg-(Arg$^{11}$)CCMSH gradually decreased to 6.81±3.71% ID/g at 24 h post-injection. In melanoma uptake blocking studies, the tumor uptake of $^{99m}$Tc-RGD-Arg-(Arg$^{11}$)CCMSH with 10 μg (6.1 nmol) of non-radiolabeled NDP-MSH co-injection was only 9.15% of the tumor uptake without NDP-MSH co-injection at 2 h after dose administration (P<0.01), demonstrating that the tumor uptake was specific and MC1 receptor-mediated. Compared to the tumor uptake of $^{99m}$Tc-RGD-Arg-(Arg$^{11}$)CCMSH, co-injection of $^{99m}$Tc-RGD-Arg-(Arg$^{1}$)CCMSH with 3.5 μg (6.1 nmol) of RGD decreased 21.2% of the tumor uptake value. Whole-body clearance of $^{99m}$Tc-RGD-Arg-(Arg$^{11}$)CCMSH was rapid, with approximately 68% of the injected radioactivity cleared through the urinary system by 2 h post-injection (Table 1). Normal organ uptakes of $^{99m}$Tc-RGD-Arg-(Arg$^{11}$) CCMSH were generally low (<3.6% ID/g) except for the kidneys after 2 h post-injection. High tumor/blood and tumor/muscle uptake ratios were demonstrated as early as 0.5 h post-injection (Table 2).

The renal uptake of $^{99m}$Tc-RGD-Arg-(Arg$^{11}$)CCMSH reached its peak value of 43.01±8.14% ID/g at 2 h post-injection. The renal uptake decreased to 16.16±4.01% ID/g at 24 h post-injection. The effects of L-lysine co-injection on the renal and tumor uptakes of $^{99m}$Tc-RGD-Lys-(Arg$^{11}$)CCMSH or $^{99m}$Tc-RGD-Arg-(Arg$^{11}$)CCMSH at 2 h post-injection are presented in FIG. 5. Co-injection of 15 mg of L-lysine significantly (p<0.05) reduced the renal uptake of $^{99m}$Tc-RGD-Arg-(Arg$^{11}$)CCMSH from 43.01±8.14% ID/g to 31.10±6.42% ID/g without affecting the tumor uptake, as well as significantly (p<0.05) decreased the renal uptake of $^{99m}$Tc-RGD-Lys-(Arg$^{11}$)CCMSH from 67.12±8.79% ID/g to 32.20±5.98% ID/g without affecting the tumor uptake at 2 h post-injection.

Figure 16:
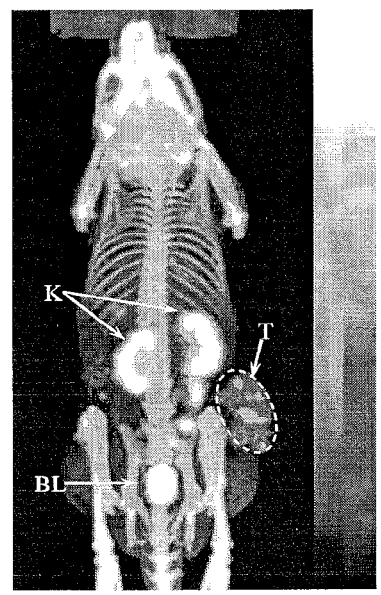
FIG. 16. Whole-body SPECT/CT image (A) of $^{99m}$Tc-RGD-Arg-(Arg$^{11}$)CCMSH in a B16/F1 melanoma-bearing C57 mouse at 2 h post-injection. Tumor (T), kidneys (K) and bladder (BL) were highlighted with arrows on the image; Radioactive HPLC profile (B) of urine sample of a B16/F1 melanoma-bearing C57 mouse at 2 h post-injection of $^{99m}$Tc-RGD-Arg-(Arg$^{11}$)CCMSH. Arrow indicates the retention time of the original compound of $^{99m}$Tc-RGD-Arg-(Arg$^{11}$) CCMSH prior to the tail vein injection.
Figure 16:
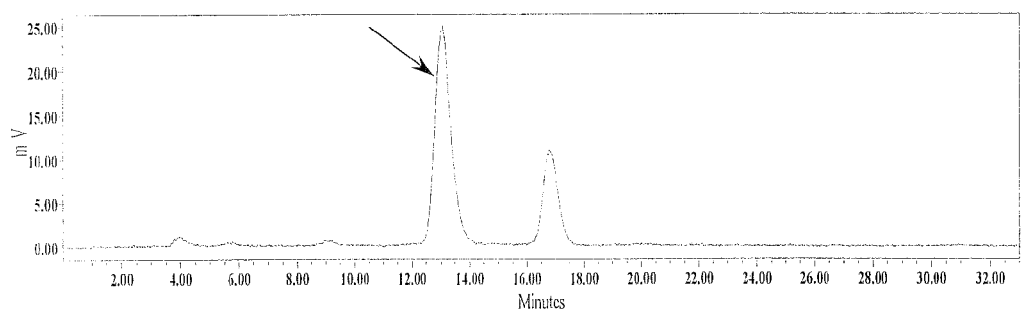

One B16/F1 melanoma-bearing C57 mouse was injected with $^{99m}$Tc-RGD-Arg-(Arg$^{11}$)CCMSH through the tail vein to visualize the tumors 2 h after dose administration. The whole-body SPECT/CT image is presented in FIG. 16. Flank melanoma tumors were visualized clearly by $^{99m}$Tc-RGD-Arg-(Arg$^{11}$)CCMSH at 2 h post-injection. The SPECT image of tumor accurately matched its anatomical information from CT image. $^{99m}$Tc-RGD-Arg-(Arg$^{11}$)CCMSH exhibited high tumor to normal organ uptake ratios except for the kidney, which was consistent with the biodistribution results. In view of the substantial renal uptake values of $^{99m}$Tc-RGD-Arg-(Arg$^{11}$)CCMSH in the biodistribution results, the urinary metabolites of $^{99m}$Tc-RGD-Arg-(Arg$^{11}$)CCMSH were analyzed by RP-HPLC 2 h post-injection. The urinary HPLC profile of $^{99m}$Tc-RGD-Arg-(Arg$^{11}$)CCMSH is shown in FIG. 6. Approximately 73% of $^{99m}$Tc-RGD-Arg-(Arg$^{11}$)CCMSH remained intact, while 27% of $^{99m}$Tc-RGD-Arg-(Arg$^{11}$)CC-MSH was transformed to one more lipophilic metabolite 2 h post-injection.

Figure 17:
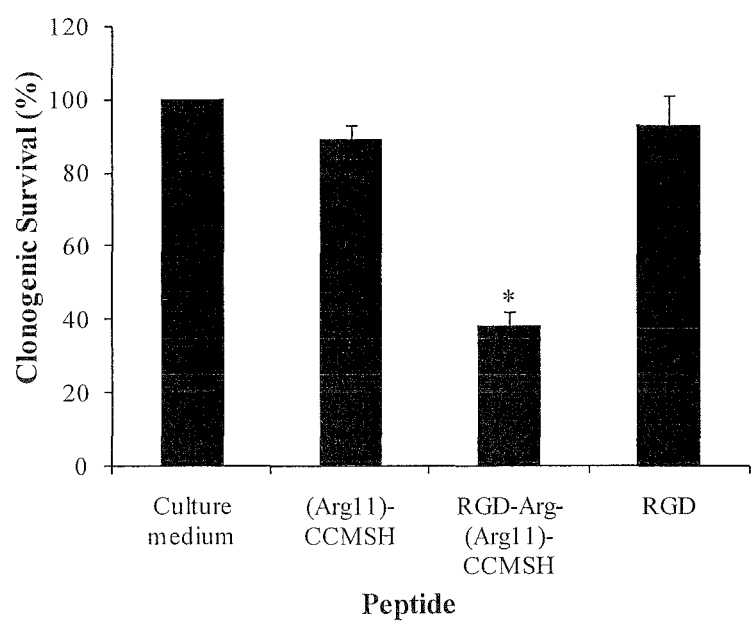
FIG. 17. Shows the clonogenic cytotoxic effect of RGD-Arg-(Arg$^{11}$)CCMSH in B16/F1 melanoma cells. The cells were visually examined under microscope for survival. Colonies contained more than 50 cells were scored as survivors. *p<0.05, significance comparison between RGD-Arg-(Arg$^{11}$)CCMSH treated cells and untreated cells (culture medium).

Clonogenic cytotoxic effect of RGD-Arg-(Arg$^{11}$)CCMSH hybrid peptide was examined in B16/F1 melanoma cells. The results are presented in FIG. 17. The clonogenic survival percentages of peptide-treated groups were normalized taking the clonogenic survival percentage of untreated group (in culture medium) as 100%. RGD-Arg-(Arg$^{11}$)CCMSH exhibited remarkable cytotoxic effect in B16/F1 melanoma cells, with 62% decrease (p<0.05) in clonogenic survival compared to that of the untreated group. In comparison with untreated cells, incubation with (Arg$^{11}$)CCMSH and RGD peptides reduced 11% and 7% of clonogenic survival, respectively. However, the differences were not significant (p>0.05).

Discussion

Malignant melanoma is the most lethal form of skin cancer with an increasing incidence. It was predicted that 68,720 cases would be newly diagnosed and 8,650 fatalities would occur in the year 2009 (18). High mortality of malignant melanoma is associated with the occurrence of aggressive melanoma metastases. Unfortunately, no curative treatment exists for metastatic melanoma. Clearly, novel and effective treatments are urgently needed to fulfill the desperate need for melanoma treatment. Recently, we have developed a novel RGD-Lys-(Arg$^{11}$)CCMSH hybrid peptide to target MC1 receptors for melanoma treatment (17). The coupling of the RGD motif (apoptosis inducer) did maintain the nanomolar MC1 receptor binding affinity of RGD-Lys-(Arg$^{11}$)CCMSH hybrid peptide (17). The remarkable clonogenic cytotoxicity of RGD-Lys-(Arg$^{11}$)CCMSH in B16/F1 melanoma cells (17) highlighted the potential of $^{188}$Re-RGD-Lys-(Arg$^{11}$)CCMSH as a novel therapeutic peptide for melanoma treatment. However, the relative high non-specific renal uptake of $^{99m}$Tc-RGD-Lys-(Arg$^{11}$)CCMSH (68.29±14.34% ID/g at 4 post-injection) needs to be reduced to facilitate the further evaluation of $^{188}$Re-labeled α-MSH hybrid peptides for melanoma treatment in melanoma mouse model.

Single amino acid change in the peptide sequence had a profound effect in reducing the non-specific renal uptake of the radiolabeled metal-cyclized α-MSH peptide (8). For instance, the replacement of Lys with Arg at the 11$^{th}$ position of $^{188}$Re-(Arg$^{11}$)CCMSH dramatically reduced its renal uptake by 50% (p<0.05) in B16/F1 melanoma-bearing C57 mice (8). We demonstrated in our previous work (17) that the Lys linker between the RGD motif and the (Arg$^{11}$)CCMSH moiety played an important role in the high non-specific renal uptake of $^{99m}$Tc-RGD-Lys-(Arg$^{11}$)CCMSH. Therefore, we replaced the Lys linker with Arg linker to determine whether such single amino acid change could substantially decrease the renal uptake of $^{99m}$Tc-RGD-Lys-(Arg$^{11}$)CCMSH in this study.

The replacement of Lys linker with Arg linker did maintain the nanomolar MC1 receptor binding affinity of the hybrid peptide. New RGD-Arg-(Arg$^{11}$)CCMSH hybrid peptide displayed 0.7 nM MC1 receptor binding affinity in B16/F1 cells (FIG. 13), whereas RGD-Lys-(Arg$^{11}$)CCMSH exhibited 2.1 nM MC1 receptor binding affinity (17). $^{99m}$Tc-RGD-Arg-(Arg$^{1}$)CCMSH could be readily prepared and was stable in mouse serum for 24 h. Rapid cellular internalization and extended retention of $^{99m}$Tc-RGD-Arg-(Arg$^{11}$)CCMSH (FIG. 13) warranted effective transportation of the RGD motif into the melanoma cells. Approximately 76-78% of the cellular uptake of $^{99m}$Tc-RGD-Arg-(Arg$^{11}$)CCMSH was blocked by RGD-Arg-(Arg$^{1}$)CCMSH or (Arg$^{11}$)CCMSH (rather than RGD), demonstrating that the cellular uptake of $^{99m}$Tc-RGD-Arg-(Arg$^{11}$)CCMSH was MC1 receptor-mediated rather than $α_vβ_3$ integrin-mediated. Favorable in vitro results warranted the evaluation of $^{99m}$Tc-RGD-Arg-(Arg$^{11}$)CCMSH in B16/F1 melanoma-bearing C57 mice.

$^{99m}$Tc-RGD-Arg-(Arg$^{11}$)CCMSH exhibited rapid high B16/F1 melanoma uptake (21.41±3.74% ID/g at 2 h post-injection) and prolonged retention in melanoma tumors (16.05±2.00% ID/g at 4 h post-injection). The tumor uptake value at 4 h post-injection was 75% of the tumor uptake value at 2 h post-injection. Even 24 h post-injection, the tumor uptake value was 6.81±3.71% ID/g. Remarkably, $^{99m}$Tc-RGD-Arg-(Arg$^{11}$)CCMSH displayed significantly (p<0.05) higher tumor uptakes than those of $^{99m}$Tc-RGD-Lys-(Arg$^{11}$)CCMSH at 0.5, 2 and 4 h post-injection. The tumor uptake values of $^{99m}$Tc-RGD-Arg-(Arg$^{11}$)CCMSH were 1.27, 1.44 and 1.28 times the tumor uptake values of $^{99m}$Tc-RGD-Lys-(Arg$^{11}$)CCMSH at 0.5, 2 and 4 h post-injection, respectively. The improved melanoma uptake of $^{99m}$Tc-RGD-Arg-(Arg$^{11}$)CCMSH was likely due to its higher MC1 receptor binding affinity compared to $^{99m}$Tc-RGD-Lys-(Arg$^{11}$)CCMSH. From the therapeutic perspective, high melanoma uptake and prolonged retention of $^{99m}$Tc-RGD-Arg-(Arg$^{11}$)CCMSH facilitated potential long-lasting synergistic therapeutic effects of apoptosis and targeted radiation from its $^{188}$Re-labeled RGD-Arg-(Arg$^{11}$)CCMSH. Tumor uptake blocking studies with NDP-MSH or RGD in B16/F1 melanoma-bearing mice (Table 2) showed that 90.9% of the tumor uptake of $^{99m}$Tc-RGD-Arg-(Arg$^{11}$)CCMSH was blocked by 6.1 nmol of NDP-MSH, whereas 21.2% of the tumor uptake of $^{99m}$Tc-RGD-Arg-(Arg$^{11}$)CCMSH was blocked by 6.1 nmol of RGD, indicating that the majority of melanoma uptake of $^{99m}$Tc-RGD-Arg-(Arg$^{11}$)CCMSH was MC1 receptor-mediated.

The replacement of Lys linker with Arg linker significantly (p<0.05) reduced the non-specific renal uptake of $^{99m}$Tc-RGD-Arg-(Arg$^{11}$)CCMSH. The renal uptake values of $^{99m}$Tc-RGD-Arg-(Arg$^{11}$)CCMSH were 53.65%, 64.08%, 52.89% and 40.14% of the renal uptake values of $^{99m}$Tc-RGD-Lys-(Arg$^{11}$)CCMSH at 0.5, 2, 4 and 24 h post-injection, respectively. Considering the structural difference between $^{99m}$Tc-RGD-Arg-(Arg$^{11}$)CCMSH and $^{99m}$Tc-RGD-Lys-(Arg$^{11}$)CCMSH, the reduced non-specific renal uptake of $^{99m}$Tc-RGD-Arg-(Arg$^{11}$)CCMSH was likely associated with the side chain of the Arg linker. The decreased renal uptake and improved tumor uptake of $^{99m}$Tc-RGD-Arg-(Arg$^{11}$)CCMSH increased the tumor/kidney uptake ratios of $^{99m}$Tc-RGD-Arg-(Arg$^{11}$)CCMSH. The tumor/kidney uptake ratios of $^{99m}$Tc-RGD-Arg-(Arg$^{11}$)CCMSH were 2.38, 2.27, 2.44 and 2.21 times the tumor/kidney uptake ratios of $^{99m}$Tc-RGD-Lys-(Arg$^{11}$)CCMSH at 0.5, 2, 4 and 24 h post-injection, respectively.

The strategy of infusing basic amino acid such as L-lysine has been successfully employed to decrease the renal uptakes of radiolabeled metal-cyclized α-MSH peptides by shielding the electrostatic interaction between positively-charged peptides and negatively-charged surface of tubule cells (15, 19, 20). Hence, 15 mg of L-lysine was co-injected with either $^{99m}$Tc-RGD-Lys-(Arg$^{11}$)CCMSH or $^{99m}$Tc-RGD-Arg-(Arg$^{11}$)CCMSH at 2 h post-injection to determine whether the non-specific renal uptakes of $^{99m}$Tc-RGD-Lys-(Arg$^{11}$)CCMSH and $^{99m}$Tc-RGD-Arg-(Arg$^{11}$)CCMSH were associated with the electrostatic interaction between the peptide and kidney cells. Co-injection of L-lysine reduced the renal uptake of $^{99m}$Tc-RGD-Lys-(Arg$^{11}$)CCMSH by 52.1% (p<0.05) and decreased the renal uptake of $^{99m}$Tc-RGD-Arg-(Arg$^{11}$)CCMSH by 27.7% (p<0.05) without affecting the tumor uptakes, demonstrating that the electrostatic interaction played an important role in the non-specific renal uptakes of $^{99m}$Tc-RGD-Lys-(Arg$^{11}$)CCMSH and $^{99m}$Tc-RGD-Arg-(Arg$^{11}$)CCMSH. The effect of L-lysine co-injection in reducing the renal uptake of $^{99m}$Tc-RGD-Arg-(Arg$^{11}$)CCMSH demonstrated it as another effective approach to further decrease the renal uptake if needed.

Flank B16/F1 melanoma tumors were clearly visualized by SPECT/CT imaging using $^{99m}$Tc-RGD-Arg-(Arg$^{11}$)CCMSH as an imaging probe 2 h post injection (FIG. 16), demonstrating the feasibility of using $^{99m}$Tc-RGD-Arg-(Arg$^{11}$)CCMSH SPECT imaging to identify the MC1 receptor expressions on human melanoma and to select the right patients for effective $^{188}$Re-RGD-Arg-(Arg$^{11}$)CCMSH treatments. The combination of using the matched-pair $^{99m}$Tc-RGD-Arg-(Arg$^{11}$)CCMSH and $^{188}$Re-RGD-Arg-(Arg$^{11}$)CCMSH could potentially enhance the success of $^{188}$Re-RGD-Arg-(Arg$^{11}$)CCMSH treatment. Imaging patients with $^{99m}$Tc-RGD-Arg-(Arg$^{11}$)CCMSH prior to the therapy would not only help the physicians to choose the right patients for effective treatments, but also allow the physicians to determine patient-specific dosimetries. Accurate patient-specific dosimetries would guide the physicians to determine the safe and efficacious doses for the patients. Furthermore, the follow-up imaging with $^{99m}$Tc-RGD-Arg-(Arg$^{11}$)CCMSH during the therapy duration could monitor the response to the treatment, as well as provide the physicians critical information to modify the therapy regimens accordingly.

The clonogenic cytotoxicity of RGD-Arg-(Arg$^{11}$)CCMSH hybrid peptide was examined in B16/F1 melanoma cells to confirm that the replacement of the Lys linker with Arg linker did not affect the cytotoxicity of RGD-Arg-(Arg$^{11}$)CCMSH. RGD-Arg-(Arg$^{11}$)CCMSH exhibited similar promising cytotoxic effect as RGD-Lys-(Arg$^{11}$)CCMSH in B16/F1 cells in this report (FIG. 7). Single treatment (3 h incubation) with 100 nM of RGD-Arg-(Arg$^{11}$)CCMSH decreased 62% of the clonogenic survival of B16/F1 cells compared to untreated control cells (in culture medium) 6 days post the treatment (FIG. 7). Neither treatment with 100 nM of (Arg$^{11}$)CCMSH nor 100 nM of RGD peptide reduced the clonogenic survival of B16/F1 cells significantly (p>0.05), demonstrating that the cytotoxic effect of RGD-Arg-(Arg$^{11}$)CCMSH hybrid peptide was due to the apoptotic effect of the RGD motif coupled to the hybrid peptide. The remarkable clonogenic cytotoxic effect of RGD-Arg-(Arg$^{11}$)CCMSH warranted the further evaluation of $^{188}$Re-labeled RGD-Arg-(Arg$^{11}$)CCMSH for melanoma treatment.

Conclusion

The replacement of the Lys linker with Arg linker exhibited a profound effect in reducing the non-specific renal uptake of $^{99m}$Tc-RGD-Arg-(Arg$^{11}$)CCMSH, as well as increasing the tumor uptake of $^{99m}$Tc-RGD-Arg-(Arg$^{11}$)CCMSH. Co-injection of L-lysine was effective in decreasing the renal uptakes of $^{99m}$Tc-RGD-Arg-(Arg$^{11}$)CCMSH and $^{99m}$Tc-RGD-Arg-(Arg$^{11}$)CCMSH. Compared to $^{99m}$Tc-RGD-Arg-(Arg$^{11}$)CCMSH, improved melanoma uptake and reduced renal uptake of $^{99m}$Tc-RGD-Arg-(Arg$^{11}$)CCMSH warranted the further evaluation of $^{188}$Re-labeled RGD-Arg-(Arg$^{11}$)CCMSH as a novel MC1 receptor-targeting therapeutic peptide for melanoma treatment in the future.

| Tissue | 0.5 h | 2 h | 4 h | 24 h | 2 h NDP Blockade | 2 h RGD Blockade |
|---|---|---|---|---|---|---|
| | | Percent injected dose/gram (% ID/g) | | | | |
| Tumor | 14.09 ± 2.42 | 21.41 ± 3.74 | 16.05 ± 2.00 | 6.81 ± 3.71 | 1.96 ± 0.71* | 16.88 ± 2.69* |
| Brain | 0.16 ± 0.02 | 0.06 ± 0.02 | 0.04 ± 0.03 | 0.06 ± 0.02 | 0.06 ± 0.01 | 0.04 ± 0.01* |

TABLE 2

Biodistribution of $^{99m}$Tc-RGD-Arg-(Arg$^{11}$)CCMSH in B16/F1 melanoma-bearing C57 mice.

| | | | | | | |
|---|---|---|---|---|---|---|
| Blood | 3.64 ± 0.69 | 0.55 ± 0.47 | 0.71 ± 0.41 | 0.24 ± 0.14 | 0.47 ± 0.29 | 0.04 ± 0.01* |
| Heart | 2.36 ± 0.37 | 0.73 ± 0.27 | 0.53 ± 0.19 | 0.34 ± 0.07 | 0.61 ± 0.21 | 0.55 ± 0.22 |
| Lung | 7.55 ± 1.29 | 2.05 ± 0.52 | 1.01 ± 0.41 | 0.76 ± 0.14 | 1.42 ± 0.31* | 1.21 ± 0.50* |
| Liver | 4.21 ± 1.04 | 3.58 ± 1.08 | 4.93 ± 0.38 | 1.89 ± 0.36 | 2.87 ± 0.34 | 2.30 ± 0.22* |
| Skin | 4.55 ± 1.01 | 1.29 ± 0.32 | 0.82 ± 0.22 | 0.75 ± 0.13 | 1.26 ± 0.14 | 0.95 ± 0.38 |
| Spleen | 2.73 ± 0.80 | 1.17 ± 0.57 | 1.75 ± 0.55 | 1.45 ± 0.37 | 1.53 ± 0.12 | 0.67 ± 0.38 |
| Stomach | 4.30 ± 1.78 | 2.75 ± 1.71 | 3.44 ± 0.83 | 0.47 ± 0.17 | 2.40 ± 0.49 | 2.03 ± 1.39 |
| Kidneys | 37.22 ± 4.72 | 43.01 ± 8.14 | 36.65 ± 11.68 | 16.16 ± 4.01 | 34.79 ± 8.46 | 38.48 ± 7.45 |
| Muscle | 1.79 ± 1.14 | 0.21 ± 0.12 | 0.32 ± 0.25 | 0.25 ± 0.05 | 0.50 ± 0.12* | 0.28 ± 0.20 |
| Pancreas | 1.02 ± 0.36 | 0.36 ± 0.20 | 0.37 ± 0.12 | 0.19 ± 0.09 | 0.37 ± 0.22 | 0.32 ± 0.17 |
| Bone | 2.01 ± 0.19 | 0.57 ± 0.15 | 0.97 ± 0.22 | 0.90 ± 0.39 | 0.98 ± 0.39 | 0.52 ± 0.42 |
| | | Percent injected dose (% ID) | | | | |
| Intestines | 3.19 ± 0.22 | 2.57 ± 0.58 | 2.62 ± 0.57 | 1.01 ± 0.11 | 2.34 ± 0.52 | 1.79 ± 0.58 |
| Urine | 43.10 ± 5.62 | 67.81 ± 6.28 | 75.13 ± 3.61 | 88.33 ± 1.64 | 76.85 ± 3.01 | 71.79 ± 5.07 |
| | | Uptake ratio of tumor/normal tissue | | | | |
| Tumor/Blood | 3.87 | 38.93 | 22.61 | 28.38 | 4.17 | 422.00 |
| Tumor/Kidneys | 0.38 | 0.50 | 0.44 | 0.42 | 0.06 | 0.44 |
| Tumor/Lung | 1.87 | 10.44 | 15.89 | 8.96 | 1.38 | 13.95 |
| Tumor/Liver | 3.35 | 5.98 | 3.26 | 3.60 | 0.68 | 7.34 |
| Tumor/Muscle | 7.87 | 101.95 | 50.16 | 27.24 | 3.92 | 60.29 |

The data was presented as percent injected dose/gram or as percent injected dose (mean ± SD, n = 5).

*p < 0.05, significance comparison between $^{99m}$Tc-RGD-Arg-(Arg$^{11}$)CCMSH with or without peptide blockade at 2 h post-injection.

REFERENCES (GROUP A)

1. Jemal A, Siegel R, Ward E, et al. Cancer statistics, 2008. *CA Cancer J. Clin.* 2008; 58:71-96.
2. Marghood A A, Slade J, Salopek T G, Kopf A W, Bart R S, Rigel D S. Basal cell and squamous cell carcinomas are important risk factors for cutaneous malignant melanoma. *Cancer.* 1995; 75:707-714.
3. Balch C M, Soong S J, Gershenwald J E, et al. Prognostic factors analysis of 17,600 melanoma patients: validation of the American joint committee on cancer melanoma staging system. *J Clin Oncol.* 2001; 19:3622-3634.
4. Anderson C M, Buzaid A C. Systematic treatments for advanced cutaneous melanoma. *Oncology.* 1995; 9:1149-1158.
5. Tatro J B, Reichlin S. Specific receptors for alpha-melanocyte-stimulating hormone are widely distributed in tissues of rodents. *Endocrinology.* 1987; 121:1900-1907.
6. Siegrist W, Solca F, Stutz S, Giuffre L, Carrel S, Girard J, Eberle A N. Characterization of receptors for alpha-melanocyte-stimulating hormone on human melanoma cells. *Cancer Res.* 1989; 49:6352-6358.
7. Chen J, Cheng Z, Hoffman T J, Jurisson S S, Quinn T P. Melanoma-targeting properties of $^{99m}$Technetium-labeled cyclic α-melanocyte-stimulating hormone peptide analogues. *Cancer Res.* 2000; 60:5649-5658.
8. Miao Y, Owen N K, Whitener D, Gallazzi F, Hoffman T J, Quinn T P. In vivo evaluation of $^{88}$Re-labeled alpha-melanocyte stimulating hormone peptide analogs for melanoma therapy. *Int Cancer.* 2002; 101:480-487.
9. Miao Y, Whitener D, Feng W, Owen N K, Chen J, Quinn T P. Evaluation of the human melanoma targeting properties of radiolabeled alpha-Melanocyte stimulating hormone peptide analogues. *Bioconjug Chem.* 2003; 14:1177-1184.
10. Giblin M F, Wang N N, Hoffman T J, Jurisson S S, Quinn T P. Design and characterization of α-melanotropin peptide analogs cyclized through rhenium and technetium metal coordination. *Proc Natl Acad Sci USA.* 1998; 95:12814-12818.
11. Froidevaux S, Calame-Christe M, Tanner H, Sumanovski L, Eberle A N. A novel DOTA-α-melanocyte-stimulating hormone analog for metastatic melanoma diagnosis. *J Nucl Med.* 2002; 43:1699-1706.
12. Froidevaux S, Calame-Christe M, Schuhmacher J, et al. A Gallium-labeled DOTA-α-melanocyte-stimulating hormone analog for PET imaging of melanoma metastases. *J Nucl Med.* 2004; 45:116-123.
13. Miao Y, Benwell K, Quinn TP. $^{99m}$Tc and $^{111}$In labeled alpha-melanocyte stimulating hormone peptides as imaging probes for primary and pulmonary metastatic melanoma detection. *J Nucl Med.* 2007; 48:73-80.
14. Miao Y, Figueroa S D, Fisher D R, et al. $^{203}$Pb-labeled alpha-melanocyte stimulating hormone peptide as an imaging probe for melanoma detection. *J Nucl Med.* 2008; 49:823-829.
15. Miao Y, Owen N K, Fisher D R, Hoffman T J, Quinn T P. Therapeutic efficacy of a $^{188}$Re labeled α-melanocyte stimulating hormone peptide analog in murine and human melanoma-bearing mouse models. *J Nucl Med.* 2005; 46:121-129.
16. Miao Y, Hylarides M, Fisher D R, et al. Melanoma therapy via peptide-targeted α-radiation. *Clin Cancer Res.* 2005; 11:5616-5621.
17. Miao Y, Shelton T, Quinn T P. Therapeutic efficacy of a $^{177}$Lu labeled DOTA conjugated α-melanocyte stimulating hormone peptide in a murine melanoma-bearing mouse model. *Cancer Biother Radiopharm.* 2007; 22:333-341.
18. Brooks P C, Clark R A, Cheresh D A. Requirement of vascular integrin $α_vβ_3$ for angiogenesis. *Science.* 1994; 264:569-571.
19. Hood J D, Cheresh D A. Role of integrins in cell invasion and migration. *Nat Rev Cancer.* 2002; 2:91-100.
20. Brooks P C, Montgomery A M, Rosenfeld M, et al. Integrin $α_vβ_3$ antagonists promote tumor regression by inducing apoptosis of angiogenic blood vessels. *Cell.* 1994; 79:1157-1164.
21. Mitjans F, Meyer T, Fittschen C, et al. In vivo therapy of malignant melanoma by means of antagonists of $α_v$ integrins. *Int J Cancer.* 2000; 87:716-723.
22. Buckley C D, Pilling D, Henriquez N V, et al. RGD peptides induce apoptosis by direct caspase-3 activation. *Nature.* 1999; 397:534-539.
23. Capello A, Krenning E P, Bernard B F, Breeman W A P, Van Hagen M P, De Jong M. Increased cell death after therapy with an Arg-Gly-Asp-linked somatostatin analog. *J Nucl Med.* 2004; 45:1716-1720.
24. Bernard B F, Capello A, Van Hagen M P, et al. Radiolabeled RGD-DTPA-Tyr$^3$-Octreotate for receptor-targeted radionuclide therapy. *Cancer Biother Radiopharm.* 2004; 19:173-180.
25. Hofland U, Capello A, Krenning E P, De Jong M, Van Hagen M P. Induction of apoptosis with hybrids of Arg-Gly-Asp molecules and peptides and antimitotic effects of hybrids of cytostatic drugs and peptides. *J Nucl Med.* 2005; 46:191 S-198S.
26. Capello A, Krenning E P, Bernard B F, Breeman W A P, Erion J L, De Jong M. Anticancer activity of targeted proapoptotic peptides. *J Nucl Med.* 2006; 47:122-129.
27. Miao Y, Gallazzi F, Guo H, Quinn T P. $^{111}$In-labeled lactam bridge-cyclized alpha-melanocyte stimulating hormone peptide analogues for melanoma imaging. *Bioconjug Chem.* 2008; 19:539-547.
28. Heppeler A, Froidevaux S, Eberle A N, Maecke H R. Receptor targeting for tumor localization and therapy with radiopeptides. *Curr Med. Chem.* 2000; 7:971-994.
29. Fung S, Hruby V J. Design of cyclic and other templates for potent and selective peptide α-MSH analogues. *Curr Opinion in Chem. Biol.* 2005; 9:352-358.
30. Schraa A J, Kok R J, Moorlag H E, et al. Targeting of RGD-modified proteins to tumor vasculature: a pharmacokinetic and cellular distribution study. *Int J Cancer.* 2002; 102:469-475.
31. Miao Y, Owen N K, Whitener D, Gallazzi F, Hoffman T J, Quinn T P. Optimizing the tumor to kidney uptake ratio of $^{188}$Re labeled alpha-melanocyte stimulating hormone peptide analogs through chemical modification. *Technetium, Rhenium and Other Metals in Chemistry and Nuclear Medicine* 6, Nicolini M., Mazzi U. Eds., Servizi Grafici Editoriali: Padova, Italy. 2002:567-570 pp.
32. Miao Y, Hoffman T J, Quinn. T P. Tumor targeting properties of $^{90}$Y and $^{177}$Lu labeled alpha-melanocyte stimulating hormone peptide analogues in a murine melanoma model. Nucl Med Biol. 2005; 32:485-493.
33. Miao Y, Fisher D R, Quinn T P. Reducing renal uptake of $^{90}$Y and $^{177}$Lu labeled alpha-melanocyte stimulating hormone peptide analogues. *Nucl Med. Biol.* 2006; 33:723-733.
34. Burke P A, DeNardo A J, Miers L A, Lamborn K R, Matzku S, DeNardo G L. Cilengitide targeting of $α_vβ_3$ integrin receptor synergizes with radioimmunotherapy to increase efficacy and apoptosis in breast cancer xenografts. *Cancer Res.* 2002; 62:4263-4272.

REFERENCES (GROUP B)

35. Marghood A. A., Slade J., Salopek T. G., Kopf A. W., Bart R. S., and Rigel D. S. (1995) Basal cell and squamous cell carcinomas are important risk factors for cutaneous malignant melanoma. *Cancer.* 75, 707-714.
36. Balch C. M., Soong S. J., Gershenwald J. E., Thompson J. F., Reintgen D. S., Cascinelli N., Urist M., McMasters K. M., Ross M. I., Kirkwood J. M., Atkins M. B., Thompson J. A., Coit D. G., Byrd D., Desmond R., Zhang Y., Liu P. Y., Lyman G. H., and Morabito A. (2001) Prognostic factors analysis of 17,600 melanoma patients: validation of the American joint committee on cancer melanoma staging system. *J. Clin. Oncol.* 19, 3622-3634.
37. Anderson C. M., Buzaid A. C., and Legha S. S. (1995) Systematic treatments for advanced cutaneous melanoma. *Oncology.* 9, 1149-1158.
38. Giblin M. F., Wang N. N., Hoffman T. J., Jurisson S. S., and Quinn T. P. (1998) Design and characterization of α-melanotropin peptide analogs cyclized through rhenium and technetium metal coordination. *Proc. Natl. Acad. Sci. U.S.A.* 95, 12814-12818.
39. Froidevaux S., Calame-Christe M., Tanner H., Sumanovski L., and Eberle A. N. (2002) A novel DOTA-α-melanocyte-stimulating hormone analog for metastatic melanoma diagnosis. *J. Nucl. Med.* 43, 1699-1706.
40. Froidevaux S., Calame-Christe M., Schuhmacher J., Tanner H., Saffrich R., Henze M., and Eberle A. N. (2004) A Gallium-labeled DOTA-α-melanocyte-stimulating hormone analog for PET imaging of melanoma metastases. *J. Nucl. Med.* 45, 116-123.
41. Miao Y., Benwell K., and Quinn T. P. (2007) $^{99m}$Tc and $^{111}$In labeled alpha-melanocyte stimulating hormone peptides as imaging probes for primary and pulmonary metastatic melanoma detection. *J. Nucl. Med.* 48, 73-80.
42. Miao Y., Figueroa S. D., Fisher D. R., Moore H. A., Testa R. F., Hoffman T. J., and Quinn T. P. (2008) $^{203}$Pb-labeled alpha-melanocyte stimulating hormone peptide as an imaging probe for melanoma detection. *J. Nucl. Med.* 49, 823-829.
43. Miao Y., Owen N. K., Fisher D. R., Hoffman T. J., and Quinn T. P. (2005) Therapeutic efficacy of a $^{188}$Re labeled α-melanocyte stimulating hormone peptide analog in murine and human melanoma-bearing mouse models. *J. Nucl. Med.* 46, 121-129.
44. Miao Y., Hylarides M., Fisher D. R., Shelton T., Moore H., Wester D. W., Fritzberg A. R., Winkelmann C. T., Hoffman T. J., and Quinn T. P. (2005) Melanoma therapy via peptide-targeted α-radiation. *Clin. Cancer Res.* 11, 5616-5621.
45. Miao Y., Shelton T., and Quinn T. P. (2007) Therapeutic efficacy of a $^{177}$Lu labeled DOTA conjugated α-melanocyte stimulating hormone peptide in a murine melanoma-bearing mouse model. *Cancer Biother. Radiopharm.* 22, 333-341.
46. Tatro J. B., and Reichlin S. (1987) Specific receptors for alpha-melanocyte-stimulating hormone are widely distributed in tissues of rodents. *Endocrinology.* 121, 1900-1907.
47. Siegrist W., Solca F., Stutz S., Giuffre L., Carrel S., Girard J., and Eberle A. N. (1989) Characterization of receptors for alpha-melanocyte-stimulating hormone on human melanoma cells. *Cancer Res.* 49, 6352-6358.
48. Chen J., Cheng Z., Hoffman T. J., Jurisson S. S., and Quinn T. P. (2000) Melanoma-targeting properties of $^{99m}$Technetium-labeled cyclic α-melanocyte-stimulating hormone peptide analogues. *Cancer Res.* 60, 5649-5658.
49. Miao Y., Owen N. K., Whitener D., Gallazzi F., Hoffman T. J., and Quinn T. P. (2002) In vivo evaluation of $^{188}$Re-labeled alpha-melanocyte stimulating hormone peptide analogs for melanoma therapy. *Int. J. Cancer.* 101, 480-487.
50. Miao Y., Whitener D., Feng W., Owen N. K., Chen J., and Quinn T. P. (2003) Evaluation of the human melanoma targeting properties of radiolabeled alpha-Melanocyte stimulating hormone peptide analogues. *Bioconjug. Chem.* 14, 1177-1184.
51. Yang J., Guo H., Gallazzi F., Padilla R. S., Berwick M., and Miao Y. (2009) Evaluation of a novel RGD-conjugated alpha-melanocyte stimulating hormone hybrid peptide for potential melanoma therapy. *Bioconjug. Chem.* 20, 1634-1642.
52. Jemal A., Siegel R., Ward E., Hao Y., Xu J., and Thun M. J. (2009) Cancer statistics, 2009. *CA. Cancer J. Clin.* 59, 225-249.
53. Wei L., Butcher C., Miao Y., Gallazzi F., Quinn T. P., Welch M. J., and Lewis J. S. (2007) Synthesis and Biological Evaluation of Cu-64 labeled Rhenium-Cyclized α-MSH Peptide Analog Using a Cross-Bridged Cyclam Chelator. *J. Nucl. Med.* 48, 64-72.
54. Miao Y., Fisher D. R., and Quinn T. P. (2006) Reducing renal uptake of $^{90}$Y and $^{177}$Lu labeled alpha-melanocyte stimulating hormone peptide analogues. *Nucl. Med. Biol.* 33, 723-733.

The invention claimed is:

1. A compound according to the chemical structure:

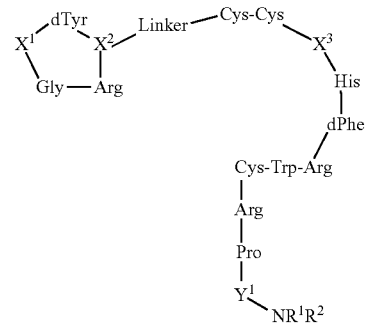

Where each of $X^1$, $X^2$ and $X^3$ is independently aspartic acid or glutamic acid;

$Y^1$ is valine, leucine or isoleucine;

$R^1$ and $R^2$ are each independently H, a $C_1$-$C_3$ alkyl group or a $C_1$ to $C_{20}$ acyl group; and Linker is absent, a positively charged amino acid residue selected from the group consisting of lysine and arginine, a negatively charged amino acid residue selected from the group consisting of aspartic acid and glutamic acid, a neutral amino acid residue selected from the group consisting of glycine, alanine valine, leucine, isoleucine, norleucine, methionine, phenylalanine, serine, thereonine, tyrosine and an amino acid according to the chemical structure:

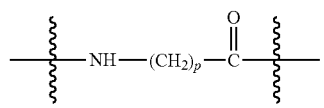

where p is an integer from 0 to 20, an oligopeptide, or a polyethylene glycol containing group according to the chemical structure:

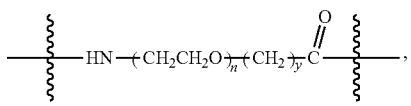

where n is 1 to 20; and
y is 1 to 4, or a pharmaceutically acceptable salt thereof, wherein said compound is optionally complexed with at least one radioisotope.

2. The compound according to claim 1 wherein $X^1$, $X^2$ or $X^3$ is aspartic acid.

3. The compound according to claim 1 wherein said linker is an amino acid residue selected from the group consisting of lysine, arginine, beta-alanine (p is 1), amino-butyric acid (Aba, p is 3), 5-aminovaleric acid (5Ava, p is 4), 6-aminohexanoic acid (6Ahx, p is 5), aspartic acid and glutamic acid, an oligopeptide containing from 2-5 amino acid residues in length wherein said amino acid residues are selected from the group consisting of lysine, arginine, beta-alanine, amino-butyric acid, 5-aminovaleric acid, 6-laminohexanoic acid, aspartic acid, glutamic acid and mixtures thereof, or a polyethylene glycol containing group comprising from 1 to 10 ethylene glycol units.

4. The compound according to claim 1 complexed with a radioisotope wherein said radioisotope is polycationic.

5. The compound according to claim 1 wherein said compound is complexed with $^{99m}$Tc or $^{99m}$Tc=O.

6. The compound according to claim 1 wherein $X^1$ and $X^2$ are aspartic acid.

7. The compound according to claim 1 wherein each of $X^1$, $X^2$ and $X^3$ is aspartic acid.

8. The compound according to claim 1, wherein Y is valine.

9. The compound according to claim 1 wherein said linker is an amino acid residue selected from the group consisting of lysine, arginine, beta-alanine (p is 1), amino-butyric acid (Aba, p is 3), 5-aminovaleric acid (5Ava, p is 4), 6-aminohexanoic acid (6Ahx, p is 5), aspartic acid or glutamic acid.

10. The compound according to claim 1 wherein said linker is beta-alanine, lysine or arginine.

11. The compound according to claim 1 wherein said linker is beta-alanine or lysine.

12. The compound according to claim 1 wherein said radioisotope is selected from the group consisting of $^{86}$Y, $^{90}$Y, $^{111}$In, $^{177}$Lu, $^{225}$Ac, $^{212}$Bi, $^{213}$Bi, $^{66}$Ga, $^{68}$Ga, $^{64}$Cu, $^{67}$Cu, $^{71}$As, $^{72}$As, $^{76}$As, $^{77}$As, $^{65}$Zn, $^{48}$V, $^{203}$Pb, $^{209}$Pb, $^{212}$Pb, $^{166}$Ho, $^{149}$Pm, $^{153}$Sm, $^{201}$Tl, $^{188}$Re, $^{186}$Re, $^{99m}$Tc, and $^{99m}$Tc=O.

13. The compound according to claim 1 wherein said radioisotope is selected from the group consisting of $^{111}$In, $^{86}$Y, $^{66}$Ga, $^{67}$Ga, $^{68}$Ga, $^{203}$Pb, $^{64}$Cu, $^{99m}$TC, $^{99m}$Tc=O, $^{90}$Y, $^{177}$Lu, $^{186}$Re, $^{188}$Re, $^{212}$Bi, $^{212}$Pb, $^{213}$Bi, $^{149}$Pm, $^{166}$Ho and $^{153}$Sm.

14. The compound according to claim 1 wherein said radioisotope is selected from the group consisting of $^{66}$Ga, $^{68}$Ga, $^{64}$Cu, $^{86}$Y.

15. The compound according to claim 1 wherein said radioisotope is selected from the group consisting of $^{111}$In, $^{67}$Ga, $^{99m}$Tc, $^{99m}$Tc=O and $^{203}$Pb.

16. The compound according to claim 1 wherein said radioisotope is selected from the group consisting of $^{90}$Y, $^{177}$La, $^{186}$Re, $^{188}$Re, $^{212}$Bi, $^{212}$Pb, $^{213}$Bi, $^{149}$Pm, $^{166}$Ho and $^{153}$Sm.

17. The compound according to claim 1 wherein said radioisotope is selected from the group consisting of $^{111}$In, $^{86}$Y, $^{66}$Ga, $^{67}$Ga, $^{68}$Ga, $^{203}$Pb, $^{64}$Cu, $^{99m}$TC and $^{99m}$TC=O.

18. A pharmaceutical composition comprising an effective amount of a compound according to claim 1 complexed with a radioisotope in combination with a pharmaceutically acceptable carrier, additive or excipient.

19. The composition according to claim 18 in parenteral dosage form.

20. The composition according to claim 18 in intravenous dosage form.

21. The composition according to claim 18 in topical dosage form.

22. The composition according to claim 18 in oral dosage form.

23. The composition according to claim 18 wherein said compound is combined with at least one agent selected from the group consisting of dacarbazine (DTIC), interleukin-2 (IL-2) and α-interferon.

24. A composition according to claim 18 further in combination with an effective amount of L-lysine.

25. A method of diagnosing the existence or absence of melanoma in a patient at risk for melanomoa comprising administering to said patient a composition according to claim 18; imaging said patient to determine if tissue in said patient exhibits elevated expression of MSH receptors compared to a standard; and diagnosing said patient as having melanoma if said tissue evidences elevated expression of MSH receptors in comparison to said standard.

26. The method according to claim 25 wherein said melanoma is metastatic melanoma.

27. The method according to claim 25 wherein said imaging is conducted using single photon emission computed tomography (SPECT) or positron emission tomography (PET).

28. The method according to claim 27 wherein said imaging is conducted using SPECT.

29. The method according to claim 27 wherein said imaging is conducted using PET.

30. A method of treating melanoma in a patient in need of therapy comprising administering to said patient an effective amount a composition according claim 18.

31. The method according to claim 30 wherein said compound is coadministered with an effective amount of at least one agent selected from the group consisting of dacarbazine (DTIC), interleukin-2 (IL-2) and α-interferon.

32. A method of monitoring therapy of a patient in treatment of melanoma, said method comprising administering to a patient undergoing melanoma treatment an imaging effective amount of a composition according to claim 18, imaging said patient to determine if tissue in said patient exhibits elevated expression of MSH receptors compared to a standard;
and comparing the results of said imaging step with said standard.

33. The method according to claim 32 wherein said standard is from said patient before treatment.

34. The method according to claim 32 wherein said standard is from a patient without melanoma.

35. The method according to claim 32 wherein said standard is from a patient in remission from melanoma.

36. The method according to claim 32 wherein said melanoma is metastatic melanoma.

37. The method according to claim 25 wherein said compound is co-administered with an effective amount of L-lysine.

38. A compound according to the chemical structure:

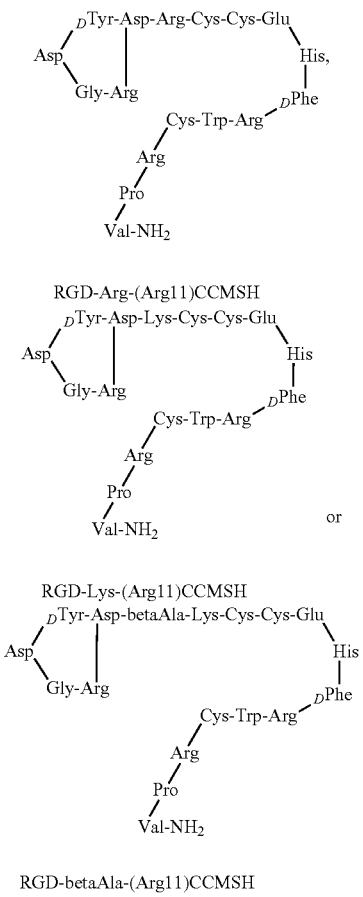

RGD-Arg-(Arg11)CCMSH

RGD-Lys-(Arg11)CCMSH

RGD-betaAla-(Arg11)CCMSH or a pharmaceutically acceptable salt thereof, optionally complexed with at least one radioisotope.

39. The compound of claim 38 which is RGD-betaAla-(Arg11) CCMSH or a pharmaceutically acceptable salt thereof.

40. The compound of claim 38 which is RGD-Lys-(Arg11) CCMSH or RGD-Arg-(Arg$^{11}$)CCMSH or a pharmaceutically acceptable salt thereof.

41. A pharmaceutical composition comprising an effective amount of a compound according to claim 38 complexed with a radioisotope in combination with a pharmaceutically acceptable carrier, additive or excipient.

42. A pharmaceutical composition comprising an effective amount of a compound according to claim 39 complexed with a radioisotope in combination with a pharmaceutically acceptable carrier, additive or excipient.

43. A pharmaceutical composition comprising an effective amount of a compound according to claim 40 complexed with a radioisotope in combination with a pharmaceutically acceptable carrier, additive or excipient.

44. The composition according to claim 41 wherein said radioisotope is selected from the group consisting of $^{111}$In, $^{86}$Y, $^{66}$Ga, $^{67}$Ga, $^{68}$Ga, $^{203}$Pb, $^{64}$Cu, $^{99m}$TC and $^{99m}$Tc=O.

45. The composition according to claim 42 wherein said radioisotope is selected from the group consisting of $^{111}$In, $^{86}$Y $^{66}$Ga, $^{67}$Ga, $^{68}$Ga, $^{203}$Pb, $^{64}$Cu, $^{99m}$Tc and $^{99m}$Tc=O.

46. The composition according to claim 43 wherein said radioisotope is selected from the group consisting of $^{111}$In, $^{86}$Y $^{66}$Ga, $^{67}$Ga, $^{68}$Ga, $^{203}$Pb $^{64}$Cu $^{99mTc\ and\ 99m}$Tc=O.

47. A method of diagnosing the existence or absence of melanoma in a patient at risk for melanoma comprising administering to said patient a composition according to claim 41; imaging said patient to determine if tissue in said patient exhibits elevated expression of MSH receptors compared to a standard; and diagnosing said patient as having melanoma if said tissue evidences elevated expression of MSH receptors in comparison to said standard.

48. A method of diagnosing the existence or absence of melanoma in a patient at risk for melanoma comprising administering to said patient a composition according to claim 42; imaging said patient to determine if tissue in said patient exhibits elevated expression of MSH receptors compared to a standard; and diagnosing said patient as having melanoma if said tissue evidences elevated expression of MSH receptors in comparison to said standard.

49. A method of diagnosing the existence or absence of melanoma in a patient at risk for melanoma comprising administering to said patient a composition according to claim 43; imaging said patient to determine if tissue in said patient exhibits elevated expression of MSH receptors compared to a standard; and diagnosing said patient as having melanoma if said tissue evidences elevated expression of MSH receptors in comparison to said standard.

50. A method of monitoring therapy of a patient in treatment of melanoma, said method comprising administering to a patient undergoing melanoma treatment an imaging effective amount of a composition according to claim 41, imaging said patient to determine if tissue in said patient exhibits elevated expression of MSH receptors compared to a standard; and
    comparing the results of said imaging step with said standard.

51. A method of monitoring therapy of a patient in treatment of melanoma, said method comprising administering to a patient undergoing melanoma treatment an imaging effective amount of a composition according to claim 42, imaging said patient to determine if tissue in said patient exhibits elevated expression of MSH receptors compared to a standard; and
    comparing the results of said imaging step with said standard.

52. A method of monitoring therapy of a patient in treatment of melanoma, said method comprising administering to a patient undergoing melanoma treatment an imaging effective amount of a composition according to claim 43, imaging said patient to determine if tissue in said patient exhibits elevated expression of MSH receptors compared to a standard; and comparing the results of said imaging step with said standard.

* * * * *